United States Patent
Kim et al.

(10) Patent No.: US 12,433,157 B2
(45) Date of Patent: Sep. 30, 2025

(54) LIGHT-EMITTING DEVICE AND ELECTRONIC APPARATUS INCLUDING THE SAME

(71) Applicant: Samsung Display Co., Ltd., Yongin-si (KR)

(72) Inventors: Seulong Kim, Yongin-si (KR); Hajin Song, Yongin-si (KR); Yangjin Cho, Yongin-si (KR); Jaehoon Hwang, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 820 days.

(21) Appl. No.: 17/684,574

(22) Filed: Mar. 2, 2022

(65) Prior Publication Data
US 2022/0293863 A1    Sep. 15, 2022

(30) Foreign Application Priority Data
Mar. 3, 2021  (KR) .......... 10-2021-0028350

(51) Int. Cl.
*H10K 85/60* (2023.01)
*C07D 403/04* (2006.01)
(Continued)

(52) U.S. Cl.
CPC ......... *H10K 85/654* (2023.02); *C07D 403/04* (2013.01); *C07D 403/14* (2013.01);
(Continued)

(58) Field of Classification Search
CPC ............. H10K 85/654; H10K 2101/10; H10K 2101/30; H10K 2101/90; H10K 50/12; H10K 50/125
See application file for complete search history.

(56) References Cited

U.S. PATENT DOCUMENTS 7,990,058 B2 * 8/2011 Cok ............... H10K 59/38
                                                            313/506
2020/0079735 A1    3/2020  Ma et al.
(Continued)

FOREIGN PATENT DOCUMENTS

KR    10-2020-0030480    3/2020
KR    10-2100620         5/2020
(Continued)

*Primary Examiner* — Vu A Nguyen
(74) *Attorney, Agent, or Firm* — Lerner David LLP

(57) ABSTRACT

Provided are a light-emitting device and an electronic apparatus including the same. The light-emitting device includes a first electrode, a second electrode facing the first electrode, and an interlayer disposed between the first electrode and the second electrode. The interlayer includes an emission layer, the emission layer includes a host, a first dopant, and a second dopant, the host, the first dopant, and the second dopant are different from each other, the host includes a compound represented by Formula 1 below, and the light-emitting device satisfies Relationship Equation 1:

[Formula 1]

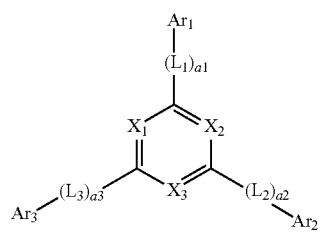

$S_1(H) \geq S_1(D2) \geq T_1(H) \geq T_1(D1) \geq T_1(D2)$    [Relationship Equation 1]

(Continued)

Formula 1 and Relationship Equation 1 are as described in the specification.

20 Claims, 3 Drawing Sheets

(51) Int. Cl.
- *C07D 403/14* (2006.01)
- *C09K 11/06* (2006.01)
- *H10K 50/11* (2023.01)
- *H10K 101/00* (2023.01)
- *H10K 101/10* (2023.01)
- *H10K 101/30* (2023.01)

(52) U.S. Cl.
CPC ............ C09K 11/06 (2013.01); H10K 85/615 (2023.02); H10K 85/6572 (2023.02); *C09K 2211/1018* (2013.01); *H10K 50/11* (2023.02); *H10K 2101/10* (2023.02); *H10K 2101/30* (2023.02); *H10K 2101/90* (2023.02)

(56) References Cited

U.S. PATENT DOCUMENTS

2020/0308209 A1\* 10/2020 Yoon ................ H10K 50/12
2021/0119148 A1   4/2021 Lee et al.

FOREIGN PATENT DOCUMENTS

| KR | 10-2140018 | 7/2020 |
| KR | 10-2020-0115890 | 10/2020 |

\* cited by examiner

| 150 |
| 130 |
| 110 |

LIGHT-EMITTING DEVICE AND ELECTRONIC APPARATUS INCLUDING THE SAME

CROSS-REFERENCE TO RELATED APPLICATION(S)

This application claims priority to and benefits of Korean Patent Application No. 10-2021-0028350 under 35 U.S.C. § 119, filed on Mar. 3, 2021 in the Korean Intellectual Property Office, the entire contents of which are incorporated herein by reference.

BACKGROUND

1. Technical Field

Embodiments relate to a light-emitting device and an electronic apparatus including the same.

2. Description of the Related Art

Self-emissive devices among light-emitting devices have wide viewing angles, high contrast ratios, short response times, as well as excellent characteristics in terms of brightness, driving voltage, and response speed.

Light-emitting devices may include a first electrode located on a substrate, and a hole transport region, an emission layer, an electron transport region, and a second electrode sequentially stacked on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transition from an excited state to a ground state to thereby generate light.

It is to be understood that this background of the technology section is, in part, intended to provide useful background for understanding the technology. However, this background of the technology section may also include ideas, concepts, or recognitions that were not part of what was known or appreciated by those skilled in the pertinent art prior to a corresponding effective filing date of the subject matter disclosed herein.

SUMMARY

Embodiments provide a light-emitting device having high emission efficiency and lifespan properties and an apparatus including the same.

Additional aspects will be set forth in part in the description, which follows and, in part, will be apparent from the description, or may be learned by practice of the embodiments of the disclosure.

According to embodiments, a light-emitting device may include a first electrode, a second electrode facing the first electrode, and an interlayer disposed between the first electrode and the second electrode, wherein the interlayer may include an emission layer, the emission layer may include a host, a first dopant, and a second dopant, the host, the first dopant, and the second dopant may be different from each other, the host may include a compound represented by Formula 1, and the light-emitting device may satisfy Relationship Equation 1.

[Formula 1]

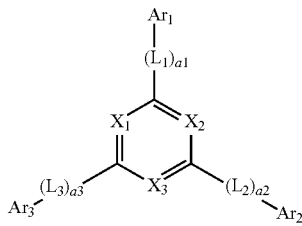

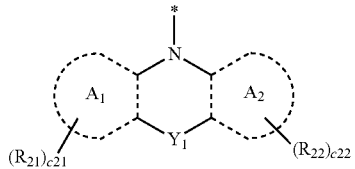

In Formula 1, $X_1$, $X_2$, and $X_3$ may each independently be $C(R_1)$ or N, and at least one of $X_1$ to $X_3$ may be N, $Ar_1$ and $Ar_2$ may each independently be a group represented by Formula 2 or a π electron-rich $C_3$-$C_{60}$ cyclic group unsubstituted or substituted with at least one $R_{10a}$, $Ar_3$ may be a group represented by Formula 2, $L_1$ to $L_3$ may each independently be a single bond, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, and a1 to a3 may each independently be an integer from 0 to 5, In Formula 2, $Y_1$ may be a single bond, O, S, $N(Z_{11})$, $C(Z_{11})(i_{12})$, or $Si(Z_{11})(Z_{12})$, $A_1$ and $A_2$ may each independently be a π electron-rich $C_3$-$C_{60}$ cyclic group unsubstituted or substituted with at least one $R_{10a}$, $R_1$, $R_{21}$, $R_{22}$, $Z_{11}$, and $Z_{12}$ may each independently be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, or —$P(=O)(Q_1)(Q_2)$, and c21 and c22 may each independently be an integer from 0 to 10, $R_{10a}$ may be deuterium (-D), —F, —Cl, —Br, —I, a hydroxyl group, a cyano group, or a nitro group, a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si$(Q_{11})(Q_{12})(Q_{13})$, —$N(Q_{11})(Q_{12})$, —$B(Q_{11})(Q_{12})$, —C(=O)(Q$_{11}$), —S(=O)$_2$(Q$_{11}$), —P(=O)(Q$_{11}$)(Q$_{12}$), or any combination thereof, a C$_3$-C$_{60}$ carbocyclic group, a C$_1$-C$_{60}$ heterocyclic group, a C$_6$-C$_{60}$ aryloxy group, or a C$_6$-C$_{60}$ arylthio group, each unsubstituted or substituted with deuterium, —F, —Cl, —Br, —I, a hydroxyl group, a cyano group, a nitro group, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{60}$ carbocyclic group, a C$_1$-C$_{60}$ heterocyclic group, a C$_6$-C$_{60}$ aryloxy group, a C$_6$-C$_{60}$ arylthio group, —Si(Q$_{21}$)(Q$_{22}$)(Q$_{23}$), —N(Q$_{21}$)(Q$_{22}$), —B(Q$_{21}$)(Q$_{22}$), —C(=O)(Q$_{21}$), —S(=O)$_2$(Q$_{21}$), —P(=O)(Q$_{21}$)(Q$_{22}$), or any combination thereof, or —Si(Q$_{31}$)(Q$_{32}$)(Q$_{33}$), —N(Q$_{31}$)(Q$_{32}$), —B(Q$_{31}$)(Q$_{32}$), —C(=O)(Q$_{31}$), —S(=O)$_2$(Q$_{31}$), or —P(=O)(Q$_{31}$)(Q$_{32}$), wherein Q$_1$ to Q$_3$, Q$_{11}$ to Q$_{13}$, Q$_{21}$ to Q$_{23}$, and Q$_{31}$ to Q$_{33}$ may each independently be hydrogen, deuterium, —F, —Cl, —Br, —I, a hydroxyl group, a cyano group, a nitro group, a C$_1$-C$_{60}$ alkyl group, a C$_2$-C$_{60}$ alkenyl group, a C$_2$-C$_{60}$ alkynyl group, a C$_1$-C$_{60}$ alkoxy group, or a C$_3$-C$_{60}$ carbocyclic group or a C$_1$-C$_{60}$ heterocyclic group, each unsubstituted or substituted with deuterium, —F, a cyano group, a C$_1$-C$_{60}$ alkyl group, a C$_1$-C$_{60}$ alkoxy group, a phenyl group, a biphenyl group, or any combination thereof, two groups of Q$_1$ to Q$_3$ may optionally be linked to each other to form a C$_4$-C$_{60}$ carbocyclic group unsubstituted or substituted with at least one R$_{10a}$ or a C$_1$-C$_{60}$ heterocyclic group unsubstituted or substituted with at least one R$_{10a}$, two groups of Q$_{11}$ to Q$_{13}$ may optionally be linked to each other to form a C$_4$-C$_{60}$ carbocyclic group unsubstituted or substituted with at least one R$_{10a}$ or a C$_1$-C$_{60}$ heterocyclic group unsubstituted or substituted with at least one R$_{10a}$, two groups of Q$_{31}$ to Q$_{33}$ may each optionally be linked to each other to form a C$_4$-C$_{60}$ carbocyclic group unsubstituted or substituted with at least one R$_{10a}$ or a C$_1$-C$_{60}$ heterocyclic group unsubstituted or substituted with at least one R$_{10a}$, and

* indicates a binding site to a neighboring atom.

$$S_1(H) \geq S_1(D2) \geq T_1(H) \geq T_1(D1) \geq T_1(D2) \quad \text{[Relationship Equation 1]}$$

In Relationship Equation 1, S$_1$(H) may be a singlet energy level (eV) of the compound represented by Formula 1 when the host includes only a compound represented by Formula 1, or a singlet energy level (eV) of an exciplex when the host includes, as a first host, the compound represented by Formula 1 and further includes a second host different from the first host, and when the first host and the second host form an exciplex, or a lower value among the singlet energy level (eV) of the first host and the singlet energy level (eV) of the second host when the host includes, as a first host, the compound represented by Formula 1 and further includes a second host different from the first host, and when the first host and the second host do not form an exciplex, S$_1$(D2) may be a singlet energy level (eV) of the second dopant, T$_1$(H) may be a triplet energy level (eV) of the compound represented by Formula 1 when the host includes only a compound represented by Formula 1, or a triplet energy level (eV) of an exciplex when the host includes, as a first host, the compound represented by Formula 1 and further includes a second host different from the first host, and when the first host and the second host form an exciplex, or a lower value among the triplet energy level (eV) of the first host and the triplet energy level (eV) of the second host when the host includes, as a first host, the compound represented by Formula 1 and further includes a second host different from the first host and when the first host, and the second host do not form an exciplex, T$_1$(D1) may be a triplet energy level (eV) of the first dopant, and T$_1$(D2) may be a triplet energy level (eV) of the second dopant.

In an embodiment, X$_1$ to X$_3$ in Formula 1 may each be N.

In an embodiment, the π electron-rich C$_3$-C$_{60}$ cyclic group may be a first ring, or a condensed ring in which two or more first rings are condensed with each other, and the first ring may be a benzene group, a naphthalene group, a cyclopentadiene group, a pyrrole group, a furan group, a thiophene group, or a silole group.

In an embodiment, Ar$_1$ in Formula 1 may be a group represented by one of Formulae 3-1 to 3-20, which are explained below.

In an embodiment, Ar$_2$ in Formula 1 may be a group represented by Formula 2, a benzene group, a heptalene group, an indene group, a naphthalene group, an azulene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, a furan group, a thiophene group, an isoindole group, an indole group, a benzofuran group, a benzothiophene group, a benzosilole group, a naphthopyrrole group, a naphthofuran group, a naphthothiophene group, a naphthosilole group, a benzocarbazole group, a dibenzocarbazole group, a dibenzofuran group, a dibenzothiophene group, a carbazole group, a dibenzosilole group, an indenocarbazole group, an indolocarbazole group, a benzofurocarbazole group, a benzothienocarbazole group, a benzosilolocarbazole group, a triindolobenzene group, a pyrrolophenanthrene group, a furanophenanthrene group, a thienophenanthrene group, a benzonaphthofuran group, a benzonaphthothiophene group, an indolophenanthrene group, a benzofuranophenanthrene group, or a benzothienophenanthrene group.

In an embodiment, L$_1$ in Formula 1 may be a single bond or a group represented by one of Formulae 4-1 to 4-17, which are explained below.

In an embodiment, L$_3$ in Formula 1 may be a single bond.

In an embodiment, Ar$_1$ and Ar$_2$ in Formula 1 may each independently be a benzene group unsubstituted or substituted with at least one R$_{10a}$ or a naphthalene group unsubstituted or substituted with at least one R$_{10a}$, and L$_1$ to L$_3$ in Formula 1 may each independently be a single bond, a benzene group unsubstituted or substituted with at least one R$_{10a}$, or a naphthalene group unsubstituted or substituted with at least one R$_{10a}$.

In an embodiment, the host may include a first host and a second host, the first host may be a compound represented by Formula 1, and the first dopant and second dopant may be different from each other.

In an embodiment, the second host may be a compound represented by Formula 301-1 or a compound represented by Formula 301-2, which are explained below.

In an embodiment, the first host and the second host may form an exciplex.

In an embodiment, the second dopant may be a boron-containing compound.

In an embodiment, the first dopant and the second dopant may each be an emitter.

In an embodiment, the first dopant may be a phosphorescence emitter, the second dopant may be a fluorescence emitter, the emission layer may simultaneously emit phosphorescence emitted from the first dopant and fluorescence emitted from the second dopant.

In an embodiment, the first dopant may be a green emitter or a red emitter, and the second dopant may be a blue emitter, a green emitter, or a red emitter.

In an embodiment, in the emission layer, an amount of the first dopant may be greater than an amount of the second dopant.

In an embodiment, the light-emitting device satisfies at least one of Relationship Equation 2-1 and Relationship Equation 2-2, which are explained below.

According to embodiments, an electronic apparatus may include the light-emitting device.

In an embodiment, the electronic apparatus may further include a thin-film transistor. The thin-film transistor may include a source electrode and a drain electrode, and the first electrode of the light-emitting device may be electrically connected to at least one of the source electrode and the drain electrode of the thin-film transistor.

In an embodiment, the electronic apparatus may further include a color filter, a color conversion layer, a touch screen layer, a polarizing layer, or any combination thereof.

BRIEF DESCRIPTION OF THE DRAWINGS

The above and other aspects, features, and advantages of certain embodiments of the disclosure will be more apparent from the following description taken in conjunction with the accompanying drawings, in which:

Figure 1:
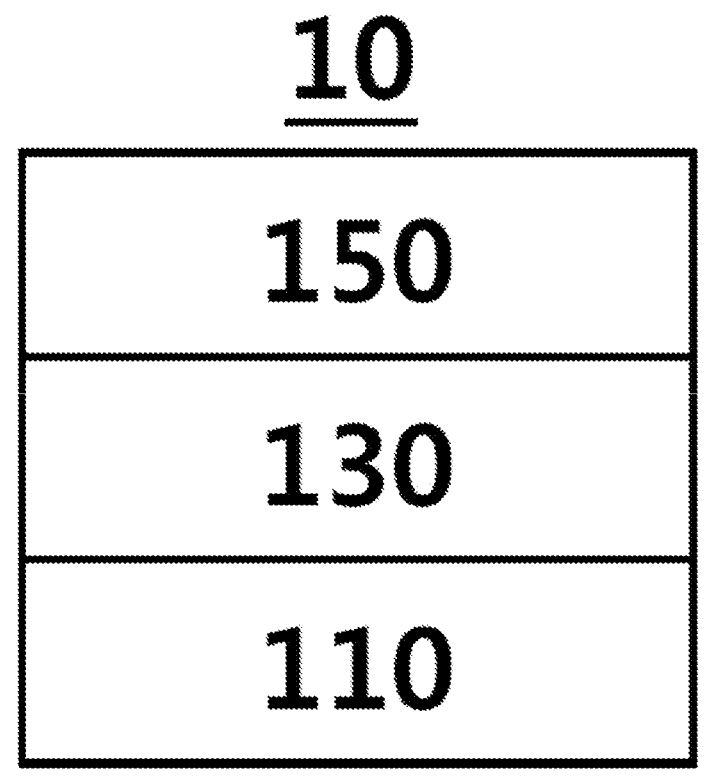

FIG. 1 is a schematic cross-sectional view of a light-emitting device according to an embodiment;

DETAILED DESCRIPTION OF THE EMBODIMENTS

Figure 2:
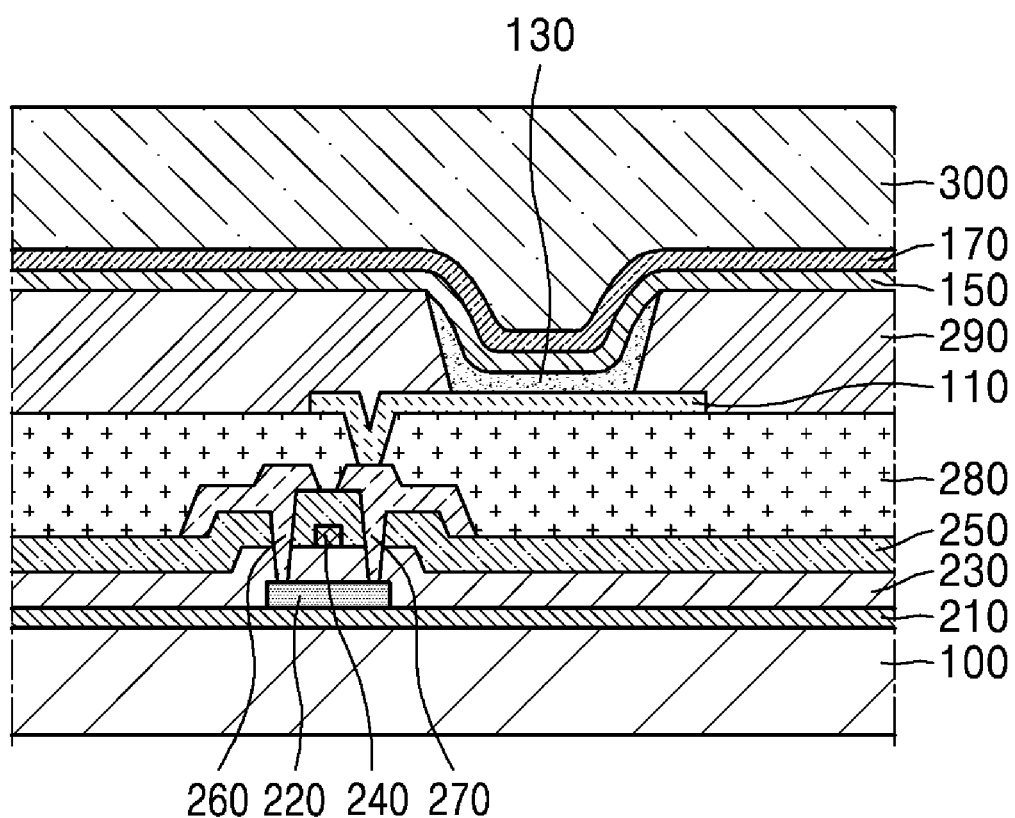
FIG. 2 is a schematic cross-sectional view of the structure of an electronic apparatus according to an embodiment.

The disclosure will now be described more fully hereinafter with reference to the accompanying drawings, in which embodiments are shown. This disclosure may, however, be embodied in different forms and should not be construed as limited to the embodiments set forth herein. Rather, these embodiments are provided so that this disclosure will be thorough and complete, and will fully convey the scope of the disclosure to those skilled in the art.

In the drawings, the sizes, thicknesses, ratios, and dimensions of the elements may be exaggerated for ease of description and for clarity. Like numbers refer to like elements throughout.

In the description, it will be understood that when an element (or region, layer, part, etc.) is referred to as being "on", "connected to", or "coupled to" another element, it can be directly on, connected to, or coupled to the other element, or one or more intervening elements may be present therebetween. In a similar sense, when an element (or region, layer, part, etc.) is described as "covering" another element, it can directly cover the other element, or one or more intervening elements may be present therebetween.

In the description, when an element is "directly on," "directly connected to," or "directly coupled to" another element, there are no intervening elements present. For example, "directly on" may mean that two layers or two elements are disposed without an additional element such as an adhesion element therebetween.

As used herein, the expressions used in the singular such as "a," "an," and "the," are intended to include the plural forms as well, unless the context clearly indicates otherwise.

As used herein, the term "and/or" includes any and all combinations of one or more of the associated listed items. For example, "A and/or B" may be understood to mean "A, B, or A and B." The terms "and" and "or" may be used in the conjunctive or disjunctive sense and may be understood to be equivalent to "and/or".

The term "at least one of" is intended to include the meaning of "at least one selected from" for the purpose of its meaning and interpretation. For example, "at least one of A and B" may be understood to mean "A, B, or A and B." When preceding a list of elements, the term, "at least one of," modifies the entire list of elements and does not modify the individual elements of the list.

It will be understood that, although the terms first, second, etc. may be used herein to describe various elements, these elements should not be limited by these terms. These terms are only used to distinguish one element from another element. Thus, a first element could be termed a second element without departing from the teachings of the disclosure. Similarly, a second element could be termed a first element, without departing from the scope of the disclosure.

The spatially relative terms "below", "beneath", "lower", "above", "upper", or the like, may be used herein for ease of description to describe the relations between one element or component and another element or component as illustrated in the drawings. It will be understood that the spatially relative terms are intended to encompass different orientations of the device in use or operation, in addition to the orientation depicted in the drawings. For example, in the case where a device illustrated in the drawing is turned over, the device positioned "below" or "beneath" another device may be placed "above" another device. Accordingly, the illustrative term "below" may include both the lower and upper positions. The device may also be oriented in other directions and thus the spatially relative terms may be interpreted differently depending on the orientations.

The terms "about" or "approximately" as used herein is inclusive of the stated value and means within an acceptable range of deviation for the recited value as determined by one of ordinary skill in the art, considering the measurement in question and the error associated with measurement of the recited quantity (i.e., the limitations of the measurement system). For example, "about" may mean within one or more standard deviations, or within ±20%, ±10%, or ±5% of the stated value.

It should be understood that the terms "comprises," "comprising," "includes," "including," "have," "having," "contains," "containing," and the like are intended to specify the presence of stated features, integers, steps, operations, elements, components, or combinations thereof in the disclosure, but do not preclude the presence or addition of one or more other features, integers, steps, operations, elements, components, or combinations thereof.

Unless otherwise defined or implied herein, all terms (including technical and scientific terms) used have the same meaning as commonly understood by those skilled in the art to which this disclosure pertains. It will be further understood that terms, such as those defined in commonly used dictionaries, should be interpreted as having a meaning that is consistent with their meaning in the context of the relevant art and should not be interpreted in an ideal or excessively formal sense unless clearly defined in the specification.

The light-emitting device may include a first electrode, a second electrode facing the first electrode, and an interlayer disposed between the first electrode and the second electrode, wherein the interlayer may include an emission layer, the emission layer may include a host, a first dopant, and a second dopant, the host, the first dopant, and the second dopant may be different from each other, the host may include a compound represented by Formula 1, and the light-emitting device may satisfy Relationship Equation 1 in the specification.

The host may include a compound represented by Formula 1 below:

[Formula 1]

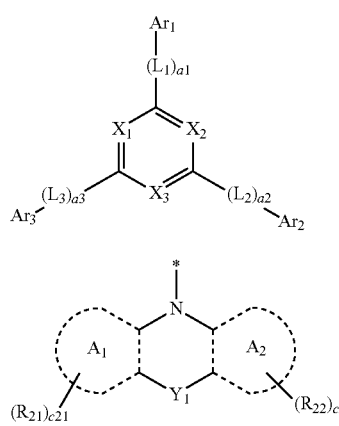

In Formula 1, $X_1$, $X_2$, and $X_3$ may each independently be $C(R_1)$ or N, and at least one of $X_1$ to $X_3$ may be N. The detailed description of $R_1$ is the same as described in the specification.

In an embodiment, $X_1$ to $X_3$ in Formula 1 may each be N.

$Ar_1$ and $Ar_2$ in Formula 1 may each independently be a group represented by Formula 2 or a π electron-rich $C_3$-$C_{60}$ cyclic group unsubstituted or substituted with at least one $R_{10a}$. The detailed descriptions of a group represented by Formula 2 and $R_{10a}$ are the same as described in the specification.

In an embodiment, the π electron-rich $C_3$-$C_{60}$ cyclic group may be a first ring, or a condensed ring in which two or more first rings are condensed with each other, and the first ring may be a benzene group, a naphthalene group, a cyclopentadiene group, a pyrrole group, a furan group, a thiophene group, or a silole group.

In an embodiment, $Ar_1$ in Formula 1 may be a group represented by one of Formulae 3-1 to 3-20:

3-1
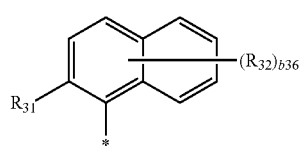

3-2
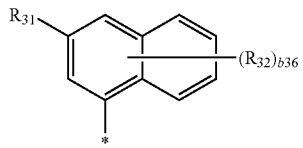

3-3
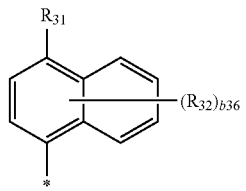

3-4
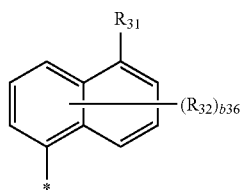

3-5
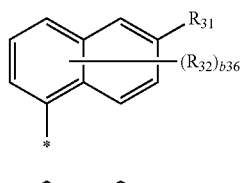

3-6
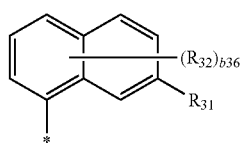

3-7
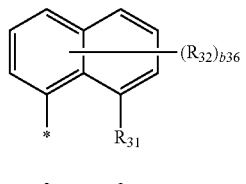

3-8
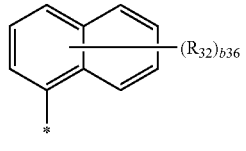

3-9
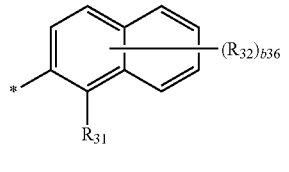

3-10
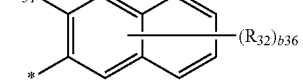

3-11
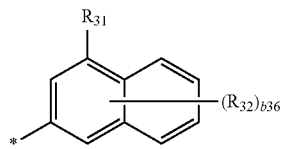

-continued

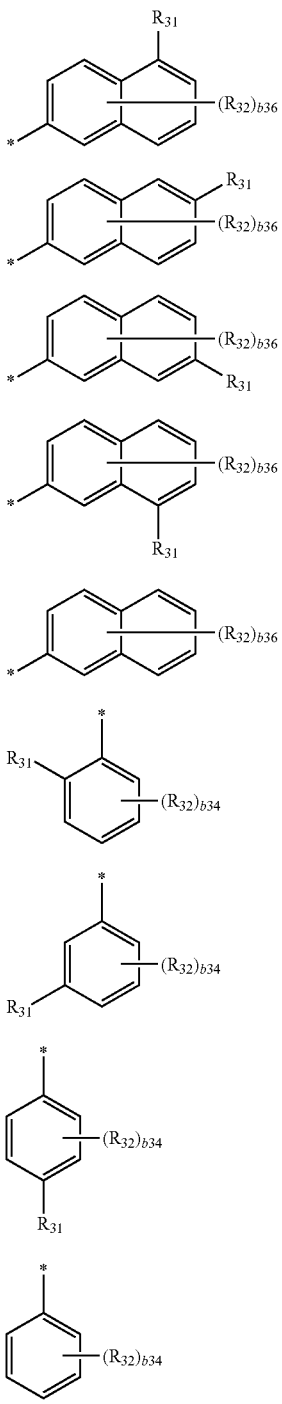

3-12

3-13

3-14

3-15

3-16

3-17

3-18

3-19

3-20

In Formulae 3-1 to 3-20, $R_{31}$ and $R_{32}$ may each independently be the same as described in connection with $R_1$, wherein $R_{31}$ may not be hydrogen.

In an embodiment, $R_{31}$ and $R_{32}$ in Formulae 3-1 to 3-20 may each independently be: hydrogen, deuterium, a hydroxyl group, or a nitro group;

a $C_1$-$C_{20}$ alkyl group, a $C_2$-$C_{20}$ alkenyl group, a $C_2$-$C_{20}$ alkynyl group or $C_1$-$C_{20}$ alkoxy group, each unsubstituted or substituted with deuterium, —$CD_3$, —$CD_2H$, —$CDH_2$, a hydroxyl group, a phenyl group, a naphthyl group, —$Si(Q_{31})(Q_{32})(Q_{33})$, —$N(Q_{31})(Q_{32})$, or any combination thereof;

a phenyl group, a naphthyl group, or a carbazolyl group, each unsubstituted or substituted with deuterium, —$CD_3$, —$CD_2H$, —$CDH_2$, a hydroxyl group, a nitro group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, a carbazolyl group, —$Si(Q_{31})(Q_{32})(Q_{33})$, —$N(Q_{31})(Q_{32})$, —$B(Q_{31})(Q_{32})$, or any combination thereof, or —$Si(Q_1)(Q_2)(Q_3)$, —$N(Q_1)(Q_2)$, or —$B(Q_1)(Q_2)$, and wherein $R_{31}$ may not be hydrogen. Qi to $Q_3$ and $Q_{31}$ to $Q_{33}$ are each the same as described in the specification.

In Formulae 3-1 to 3-20, b36 may be an integer from 0 to 6.

In Formulae 3-1 to 3-20, b34 may be an integer from 0 to 4.

In an embodiment, $Ar_2$ in Formula 1 may be a group represented by Formula 2, a benzene group, a heptalene group, an indene group, a naphthalene group, an azulene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, a furan group, a thiophene group, an isoindole group, an indole group, a benzofuran group, a benzothiophene group, a benzosilole group, a naphthopyrrole group, a naphthofuran group, a naphthothiophene group, a naphthosilole group, a benzocarbazole group, a dibenzocarbazole group, a dibenzofuran group, a dibenzothiophene group, a carbazole group, a dibenzosilole group, an indenocarbazole group, an indolocarbazole group, a benzofurocarbazole group, a benzothienocarbazole group, a benzosilolocarbazole group, a triindolobenzene group, a pyrrolophenanthrene group, a furanophenanthrene group, a thienophenanthrene group, a benzonaphthofuran group, a benzonaphthothiophene group, an indolophenanthrene group, a benzofuranophenanthrene group, or a benzothienophenanthrene group. The detailed description of $R_{10a}$ is the same as described in the specification.

In embodiments, $Ar_2$ in Formula 1 may be a group represented by Formula 2; or a benzene group, a naphthalene group, an anthracene group, a phenanthrene group, or a carbazole group, each unsubstituted or substituted with at least one $R_{10a}$. The detailed description of $R_{10a}$ is the same as described in the specification.

In Formula 1, $Ar_3$ may be a group represented by Formula 2. The detailed description of Formula 2 is the same as described in the specification.

In Formula 1, $L_1$ to $L_3$ may each independently be a single bond, a $C_3$-$C_{60}$ carbocyclic group unsubstituted or substituted with at least one $R_{10a}$, or a $C_1$-$C_6$ heterocyclic group unsubstituted or substituted with at least one $R_{10a}$. The detailed description of $R_{10a}$ is the same as described in the specification.

In an embodiment, $Ar_1$ and $Ar_2$ in Formula 1 may each independently be a benzene group unsubstituted or substituted with at least one $R_{10a}$ or a naphthalene group unsubstituted or substituted with at least one $R_{10a}$, and $L_1$ to $L_3$ in Formula 1 may each independently be a single bond, a benzene group unsubstituted or substituted with at least one $R_{10a}$, or a naphthalene group unsubstituted or substituted with at least one $R_{10a}$. The detailed description of $R_{10a}$ is the same as described in the specification.

In an embodiment, $L_1$ in Formula 1 may be a single bond or a group represented by one of Formulae 4-1 to 4-17:

4-1
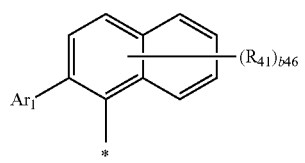

4-2
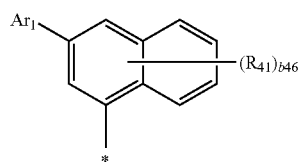

4-3
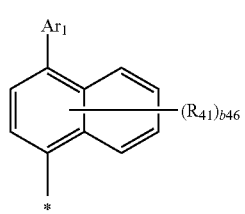

4-4
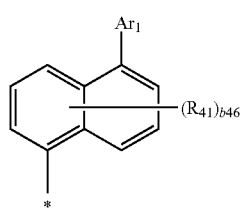

4-5
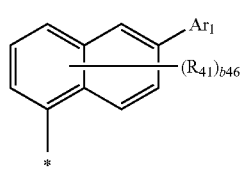

4-6
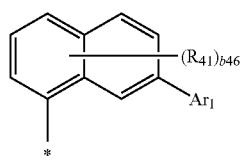

4-7
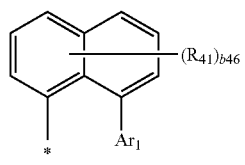

4-8
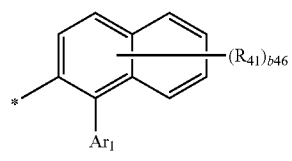

-continued 4-9
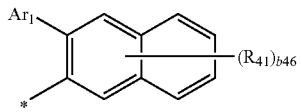

4-10
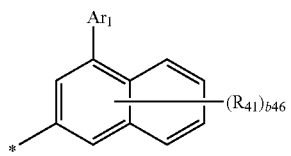

4-11
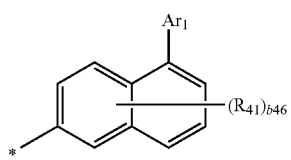

4-12
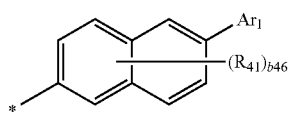

4-13

4-14
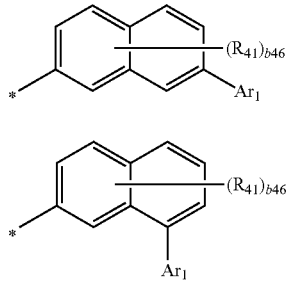

4-15
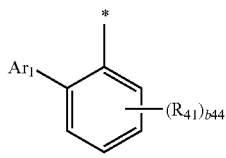

4-16
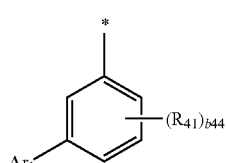

4-17
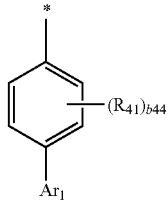

In Formulae 4-1 to 4-17, $Ar_1$ is the same as described in the specification, and $R_{41}$ is the same as described in connection with $R_1$.

In Formulae 4-1 to 4-17, b46 may be an integer from 0 to 6.

In Formulae 4-1 to 4-17, b44 may be an integer from 0 to 4.

In one embodiment, $L_3$ in Formula 1 may be a single bond, but embodiments are not limited thereto.

In Formula 1, a1 to a3 may each independently be an integer from 0 to 5.

In an embodiment, a1 to a3 in Formula 1 may each be 0, 1, or 2.

In an embodiment, a3 in Formula 1 may be 0.

$Q_1$ to $Q_3$, $Q_{11}$ to $Q_{13}$, $Q_{21}$ to $Q_{23}$, and $Q_{31}$ to $Q_{33}$ as used herein may each independently be: hydrogen; deuterium; —F; —Cl; —Br; —I; a hydroxyl group; a cyano group; a nitro group; $C_1$-$C_{60}$ alkyl group; $C_2$-$C_{60}$ alkenyl group; $C_2$-$C_{60}$ alkynyl group; $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

In Formulas 1 and 2, two groups of $Q_1$ to $Q_3$ may optionally be linked to each other to form a $C_4$-$C_{60}$ carbocyclic group unsubstituted or substituted with at least one $R_{10a}$ or a $C_1$-$C_{60}$ heterocyclic group unsubstituted or substituted with at least one $R_{10a}$, two groups of $Q_{11}$ to $Q_{13}$ may optionally be linked to each other to form a $C_4$-$C_{60}$ carbocyclic group unsubstituted or substituted with at least one $R_{10a}$ or a $C_1$-$C_{60}$ heterocyclic group unsubstituted or substituted with at least one $R_{10a}$, and two groups of $Q_{31}$ to $Q_{33}$ may optionally be linked to each other to form a $C_4$-$C_{60}$ carbocyclic group unsubstituted or substituted with at least one $R_{10a}$ or a $C_1$-$C_{60}$ heterocyclic group unsubstituted or substituted with at least one $R_{10a}$, and

* indicates a binding site to a neighboring atom.

[Formula 2]

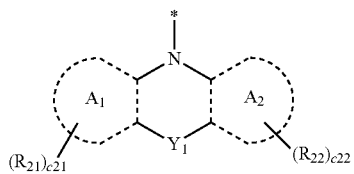

2

In Formula 2, $Y_1$ may be a single bond, O, S, $N(Z_{11})$, $C(Z_{11})(Z_{12})$, or $Si(Z_{11})(Z_{12})$. The detailed description of $Z_1$ and $Z_{12}$ are each the same as described in the specification.

In an embodiment, $Y_1$ in Formula 2 may be a single bond, but embodiments of the disclosure are not limited thereto.

In Formula 2, $A_1$ and $A_2$ may each independently be a π electron-rich $C_3$-$C_{60}$ cyclic group unsubstituted or substituted with at least one $R_{10a}$. The π electron-rich $C_3$-$C_6$ cyclic group is the same as described in the specification.

In an embodiment, $A_1$ and $A_2$ in Formula 2 may each independently be a benzene group, a naphthalene group, an anthracene group, or a phenanthrene group, each unsubstituted or substituted with at least one $R_{10a}$. The detailed description of $R_{10a}$ is the same as described in the specification.

In Formulae 1 and 2, $R_1$, $R_{21}$, $R_{22}$, $Z_{11}$, and $Z_{12}$ may each independently be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$). $Q_1$ to $Q_3$ and $Q_{31}$ to $Q_{33}$ are each the same as described in the specification.

In an embodiment, $R_1$, $R_{21}$, $R_{22}$, $Z_{11}$, and $Z_{12}$ in Formulae 1 and 2 may each independently be: hydrogen, deuterium, a hydroxyl group, or a nitro group;
a $C_1$-$C_{20}$ alkyl group, a $C_2$-$C_{20}$ alkenyl group, a $C_2$-$C_{20}$ alkynyl group, or a $C_1$-$C_{20}$ alkoxy group, each unsubstituted or substituted with deuterium, —CD$_3$, —CD$_2$H, —CDH$_2$, a hydroxyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, —Si($Q_{31}$)($Q_{32}$)($Q_{33}$), —N($Q_{31}$)($Q_{32}$), —B($Q_{31}$)($Q_{32}$), or any combination thereof;
a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an isoindolyl group, an indolyl group, an indazolyl group, a purinyl group, a cinnolinyl group, a carbazolyl group, a benzofuranyl group, a dibenzofuranyl group, a dibenzothiophenyl group, a benzocarbazolyl group, or a dibenzocarbazolyl group, each unsubstituted or substituted with deuterium, —CD$_3$, —CD$_2$H, —CDH$_2$, a hydroxyl group, a nitro group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an isoindolyl group, an indolyl group, an indazolyl group, a purinyl group, a cinnolinyl group, a carbazolyl group, a benzofuranyl group, a dibenzofuranyl group, a dibenzothiophenyl group, a benzocarbazolyl group, a dibenzocarbazolyl group, —Si($Q_{31}$)($Q_{32}$)($Q_{33}$), —N($Q_{31}$)($Q_{32}$), —B($Q_{31}$)($Q_{32}$), or any combination thereof, or
—Si($Q_1$)($Q_2$)($Q_3$), —N($Q_1$)($Q_2$), or —B($Q_1$)($Q_2$). $Q_1$ to $Q_3$ and $Q_{31}$ to $Q_{33}$ are each the same as described in the specification.

In embodiments, $R_1$, $R_{21}$, $R_{22}$, $Z_{11}$, and $Z_{12}$ in Formulae 1 and 2 may each independently be: hydrogen, deuterium, a hydroxyl group, or a nitro group;
a $C_1$-$C_{20}$ alkyl group unsubstituted or substituted with deuterium, —CD$_3$, —CD$_2$H, —CDH$_2$, a hydroxyl group, a phenyl group, a naphthyl group, —Si($Q_{31}$)($Q_{32}$)($Q_{33}$), —N($Q_{31}$)($Q_{32}$), —B($Q_{31}$)($Q_{32}$), or any combination thereof, a phenyl group, a naphthyl group, or a carbazolyl group, each unsubstituted or substituted with deuterium, —CD$_3$, —CD$_2$H, —CDH$_2$, a hydroxyl group, a nitro group, a C$_1$-C$_{20}$ alkyl group, a C$_2$-C$_{20}$ alkenyl group, a C$_2$-C$_{20}$ alkynyl group, a C$_1$-C$_{20}$ alkoxy group, a phenyl group, a naphthyl group, a carbazolyl group, —Si(Q$_{31}$)(Q$_{32}$)(Q$_{33}$), —N(Q$_{31}$)(Q$_{32}$), —B(Q$_{31}$)(Q$_{32}$), or any combination thereof, or —Si(Q$_1$)(Q$_2$)(Q$_3$), —N(Q$_1$)(Q$_2$), or —B(Q$_1$)(Q$_2$). Q$_1$ to Q$_3$ and Q$_{31}$ to Q$_{33}$ are each the same as described in the specification.

In Formula 2, c21 and c22 may each independently be an integer from 0 to 10.

In an embodiment, the compound represented by Formula 1 may be selected from Compounds 1 to 12:

1

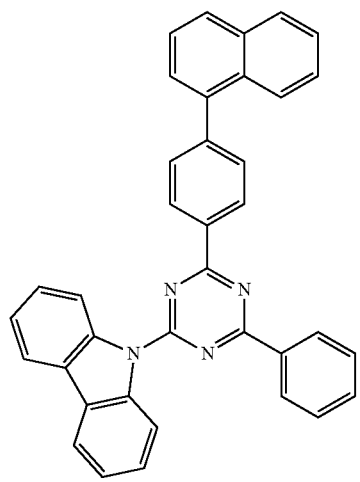

2

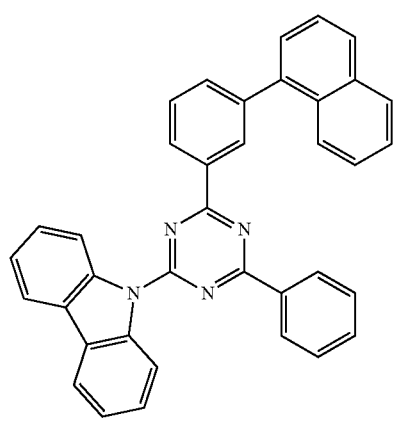

3

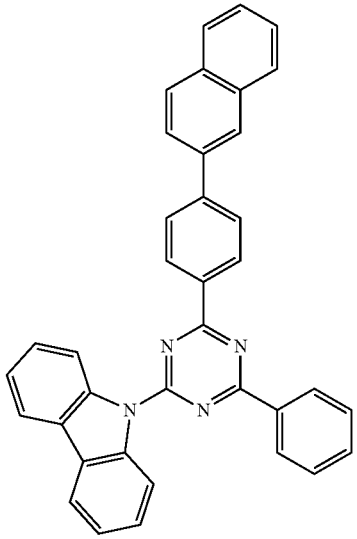

4

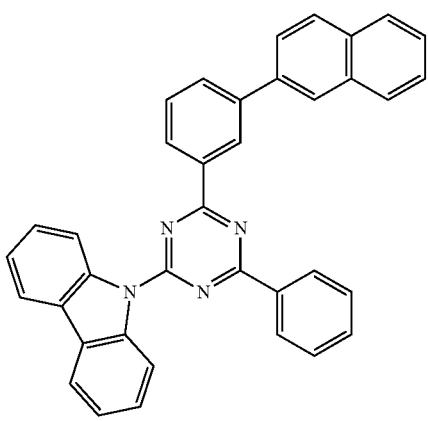

5

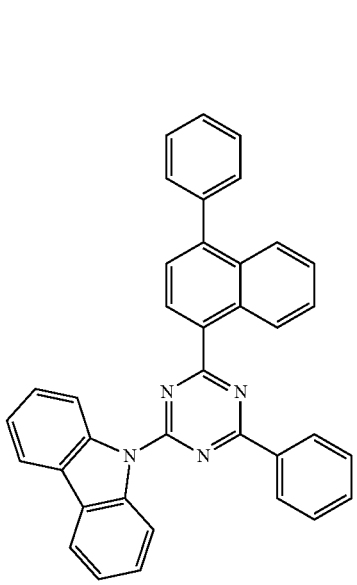

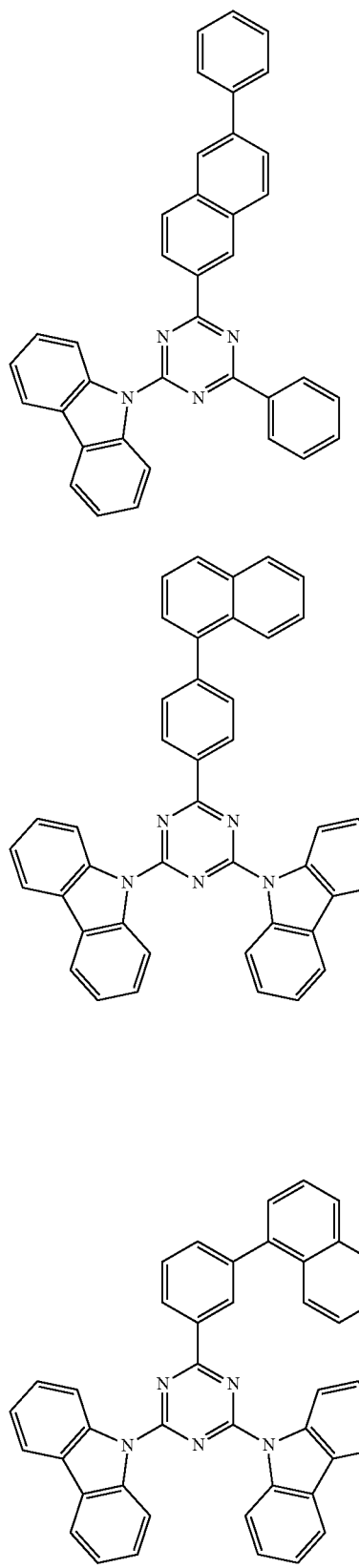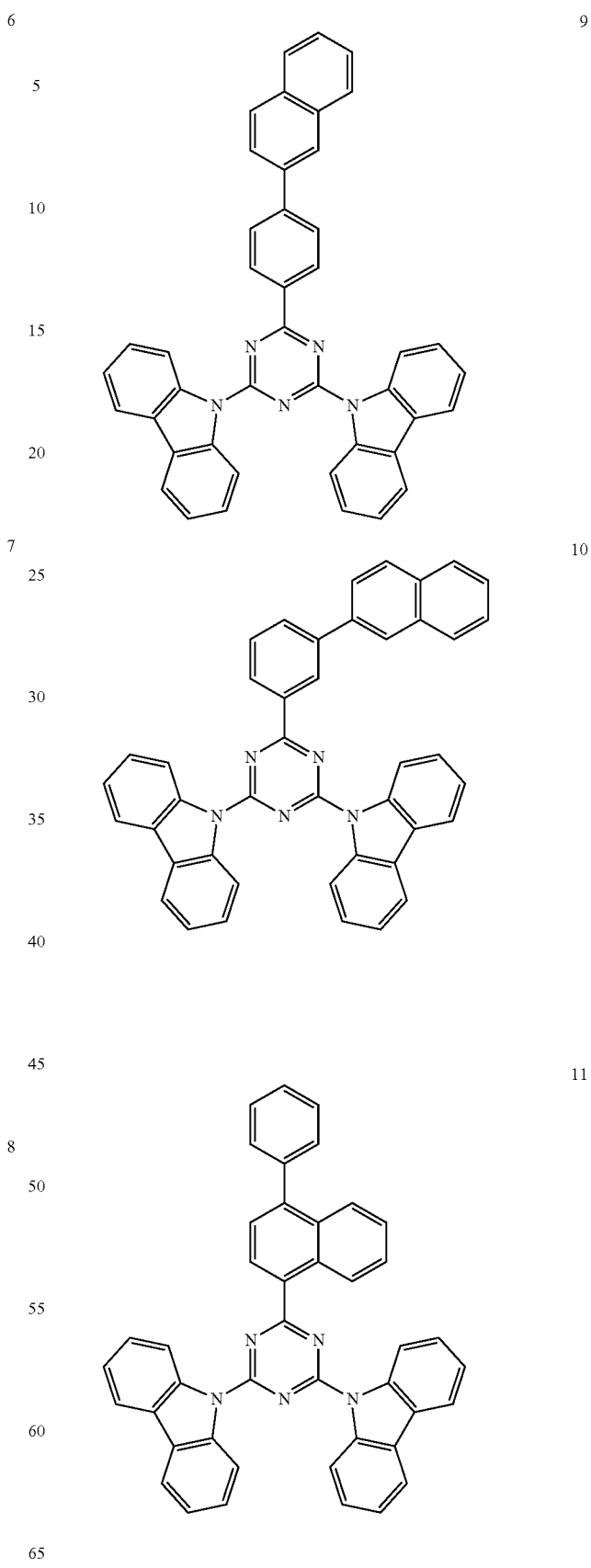

-continued

12

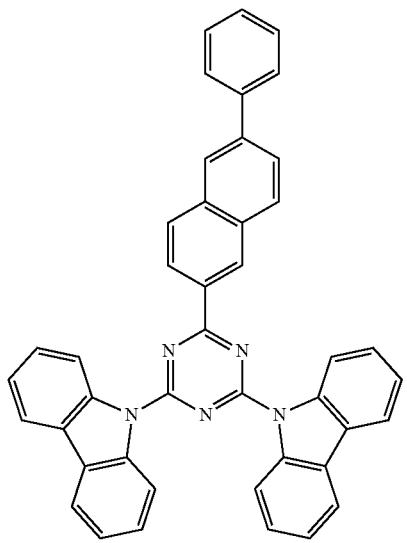

In an embodiment, the host in the light-emitting device may include a first host and a second host, the first host may be a compound represented by Formula 1, and the first host and the second host may be different from each other.

In embodiments, the second host may be a compound represented by Formula 301-1 or a compound represented by Formula 301-2.

group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si$(Q_{301})(Q_{302})(Q_{303})$, —N$(Q_{301})(Q_{302})$, —B$(Q_{301})(Q_{302})$, —C(=O)$(Q_{301})$, —S(=O)$_2$$(Q_{301})$, or —P(=O)$(Q_{301})(Q_{302})$, xb22 and xb23 may each independently be 0, 1, or 2, and $Q_{301}$ to $Q_{303}$ are independently each the same as described in connection with Qi.

In an embodiment, the first host and the second host may form an exciplex.

In another embodiment, the first host and the second host may not form an exciplex.

Synthesis methods of the compounds represented by Formula 1 may be recognizable by one of ordinary skill in the art by referring to Synthesis Examples and/or Examples provided below.

In the light-emitting device, the detailed descriptions of the first dopant and the second dopant are the same as described in connection with a phosphorescent dopant, a fluorescent dopant, and a delayed fluorescence material to be described later.

In an embodiment, the first dopant in the light-emitting device is the same as described in connection with the phosphorescence dopant.

[Formula 301-1]

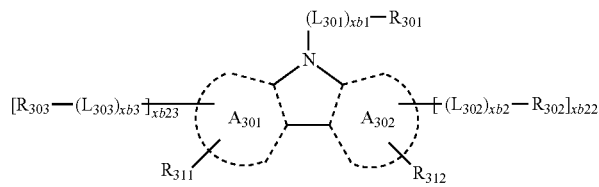

[Formula 301-2]

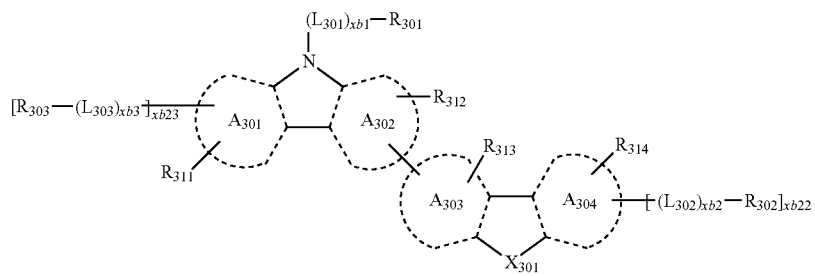

In Formulae 301-1 and 301-2,
ring $A_{301}$ to ring $A_{304}$ and $L_{301}$ to $L_{304}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$,
xb1 to xb4 may each independently be an integer from 0 to 5,
$X_{301}$ may be O, S, N-[$(L_{304})_{xb4}$-$R_{304}$], C$(R_{304})(R_{305})$, or Si$(R_{304})(R_{305})$,
$R_{301}$ to $R_{305}$ and $R_{311}$ to $R_{314}$ may each independently be hydrogen, deuterium, —F, —Cl, —Br, —I, a hydroxyl group, a cyano group, a nitro group, a $C_1$-$C_{60}$ alkyl In embodiments, the first dopant in the light-emitting device may be an iridium (Ir)-containing compound, but embodiments of the disclosure are not limited thereto.

In an embodiment, the second dopant in the light-emitting device is the same as described in connection with the delayed fluorescence material.

In embodiments, the second dopant in the light-emitting device may be a boron-containing compound, but embodiments of the disclosure are not limited thereto.

In an embodiment, the first dopant and the second dopant in the light-emitting device may each be an emitter.

In an embodiment, the first dopant in the light-emitting device may be a phosphorescence emitter, the second dopant may be a fluorescence emitter, and the emission layer may simultaneously emit phosphorescence emitted from the first dopant and fluorescence emitted from the second dopant.

In an embodiment, the second dopant in light-emitting device may be a prompt fluorescence emitter or a delayed fluorescence emitter.

In an embodiment, in the light-emitting device, the first dopant may be a green emitter or a red emitter, and the second dopant may be a blue emitter, a green emitter, or a red emitter.

In an embodiment, in the light-emitting device, the first dopant may be a green emitter, and the second dopant may be a blue emitter; the first dopant may be a green emitter, and the second dopant may be a green emitter; the first dopant may be a green emitter, and the second dopant may be a red emitter; the first dopant may be a red emitter, and the second dopant may be a blue emitter; the first dopant may be a red emitter, and the second dopant may be a green emitter; or the first dopant may be a red emitter, and the second dopant may be a red emitter.

In an embodiment, in the emission layer of the light-emitting device, an amount of the first dopant may be greater than an amount of the second dopant.

For example, in the light-emitting device, an amount of the first dopant may be in a range of about 2 parts by weight to about 10 parts by weight based on the total weight of 100 parts by weight of the emission layer.

For example, in the light-emitting device, an amount of the second dopant may be in a range of about 0.01 parts by weight to about 2 parts by weight based on the total weight of 100 parts by weight of the emission layer.

The light-emitting device may satisfy Relationship Equation 1:

$$S_1(H) \geq S_1(D2) \geq T_1(H) \geq T_1(D1) \geq T_1(D2) \quad \text{[Relationship Equation 1]}$$

In Relationship Equation 1, $S_1(H)$ may be: a singlet energy level (eV) of the compound represented by Formula 1 when the host includes only a compound represented by Formula 1; or a singlet energy level (eV) of an exciplex when the host includes, as a first host, the compound represented by Formula 1 and further includes a second host different from the first host, and when the first host and the second host form an exciplex; or a lower value among the singlet energy level (eV) of the first host and the singlet energy level (eV) of the second host when the host includes, as a first host, the compound represented by Formula 1 and further includes a second host different from the first host, and when the first host and the second host do not form an exciplex.

In Relationship Equation 1, $S_1(D2)$ may be a singlet energy level (eV) of the second dopant.

In Relationship Equation 1, $T_1(H)$ may be: a triplet energy level (eV) of the compound represented by Formula 1 when the host includes only the compound represented by Formula 1; or a triplet energy level (eV) of an exciplex when the host includes, as a first host, the compound represented by Formula 1 and further includes a second host different from the first host, and when the first host and the second host form an exciplex; or a lower value among the triplet energy level (eV) of the first host and the triplet energy level (eV) of the second host when the host includes, as a first host, the compound represented by Formula 1 and further includes a second host different from the first host and when the first host and the second host do not form an exciplex.

In Relationship Equation 1, $T_1(D1)$ may be a triplet energy level (eV) of the first dopant.

In Relationship Equation 1, $T_1(D2)$ may be a triplet energy level (eV) of the second dopant.

In an embodiment, the light-emitting device may satisfy at least one of Relationship Equation 2-1 and Relationship Equation 2-2:

$$LUMO(H)+0.1 \text{ eV} \leq LUMO(D1) \quad \text{[Relationship Equation 2-1]}$$

$$LUMO(H)+0.1 \text{ eV} \leq LUMO(D2) \quad \text{[Relationship Equation 2-2]}$$

In Relationship Equations 2-1 and 2-2,

LUMO(H) may be: a lowest unoccupied molecular orbital (LUMO) energy level (eV) of the compound represented by Formula 1 when the host includes only a compound represented by Formula 1; or a LUMO energy level (eV) of an exciplex when the host includes, as a first host, the compound represented by Formula 1 and further includes a second host different from the first host, and when the first host and the second host form an exciplex; or a lower value among the LUMO energy level (eV) of the first host and the LUMO energy level (eV) of the second host when the host includes, as a first host, the compound represented by Formula 1 and further includes a second host different from the first host, and when the first host and the second host do not form an exciplex, LUMO(D1) may be a LUMO energy level (eV) of the first dopant, and LUMO(D2) may be a LUMO energy level (eV) of the second dopant.

In embodiments, the singlet, triplet, and LUMO energy levels of the first dopant and the second dopant may be evaluated by using a density functional (DFT) method.

The host in the light-emitting device may include a compound represented by Formula 1, and thus, the triplet energy level and charge balance of the host may be controlled, resulting in an improvement of the emission efficiency of the light-emitting device. Because the light-emitting device satisfies Relationship Equation 1, the triplet-triplet annihilation (TTA) and the triplet exciton-polaron annihilation (TPA) may decrease, and the concentration of the triplet state in the emission layer may decrease, thereby improving emission efficiency and stability. Thus, the light-emitting device, for example, an organic light-emitting device, may have a high emission efficiency and a long lifespan.

In embodiments, the first electrode of the light-emitting device may be an anode, the second electrode of the light-emitting device may be a cathode, and the interlayer may further include a hole transport region located between the first electrode and the emission layer and an electron transport region located between the emission layer and the second electrode.

The hole transport region may include a hole injection layer, a hole transport layer, an emission auxiliary layer, an electron blocking layer, or any combination thereof.

The electron transport region may include a buffer layer, a hole blocking layer, an electron control layer, an electron transport layer, an electron injection layer, or any combination thereof.

In embodiments, the light-emitting device may include a capping layer located outside the first electrode or outside the second electrode.

For example, the light-emitting device may further include at least one of a first capping layer located outside the first electrode and a second capping layer located outside the second electrode, and the compound represented by Formula 1 may be included in at least one of the first capping layer and the second capping layer. More details for the first capping layer and/or second capping layer are the same as described in the specification.

In an embodiment, the light-emitting device may include a first capping layer located outside the first electrode and including the compound represented by Formula 1; or a second capping layer located outside the second electrode and including the compound represented by Formula 1; or the first capping layer and the second capping layer.

The wording "(an interlayer and/or capping layer) includes a compound represented by Formula 1" as used herein may be understood as "(an interlayer and/or capping layer) may include one kind of compound represented by Formula 1 or two different kinds of compounds, each represented by Formula 1."

For example, the interlayer and/or capping layer may include, as the compound represented by Formula 1, Compound 1 only. In this regard, Compound 1 may exist in the emission layer of the light-emitting device. In embodiments, the interlayer may include, as the compound represented by Formula 1, Compounds 1 and 2. In this regard, Compound 1 and Compound 2 may exist in an identical layer (for example, Compound 1 and Compound 2 may all exist in an emission layer), or different layers (for example, Compound 1 may exist in an emission layer and Compound 2 may exist in an electron transport region).

The term "interlayer" as used herein refers to a single layer and/or multiple layers located between a first electrode and a second electrode of a light-emitting device.

Another aspect provides an electronic apparatus which may include the light-emitting device. The electronic apparatus may further include a thin-film transistor. In embodiments, the electronic apparatus may further include a thin-film transistor including a source electrode and a drain electrode, and the first electrode of the light-emitting device may be electrically connected to at least one of the source electrode and the drain electrode of the thin-film transistor. In an embodiment, the electronic apparatus may further include a color filter, a color conversion layer, a touch screen layer, a polarizing layer, or any combination thereof. More details on the electronic apparatus are the same as described in the specification.

[Description of FIG. 1]

FIG. 1 is a schematic cross-sectional view of a light-emitting device 10 according to an embodiment. The light-emitting device 10 includes a first electrode 110, an interlayer 130, and a second electrode 150.

Hereinafter, the structure of the light-emitting device 10 according to an embodiment and a method of manufacturing the light-emitting device 10 will be described in connection with FIG. 1.

[First Electrode 110]

In FIG. 1, a substrate may be further included under the first electrode 110 or above the second electrode 150. The substrate may be a glass substrate or a plastic substrate. In embodiments, the substrate may be a flexible substrate, and may include plastics with excellent heat resistance and durability, such as polyimide, polyethylene terephthalate (PET), polycarbonate, polyethylene napthalate, polyarylate (PAR), polyetherimide, or any combination thereof.

The first electrode 110 may be formed by, for example, depositing or sputtering a material for forming the first electrode 110 on the substrate. When the first electrode 110 is an anode, a material for forming the first electrode 110 may be a high work function material that facilitates injection of holes.

The first electrode 110 may be a reflective electrode, a semi-transmissive electrode, or a transmissive electrode. When the first electrode 110 is a transmissive electrode, a material for forming the first electrode 110 may include indium tin oxide (ITO), indium zinc oxide (IZO), tin oxide (SnO$_2$), zinc oxide (ZnO), or any combinations thereof. In embodiments, when the first electrode 110 is a semi-transmissive electrode or a reflective electrode, magnesium (Mg), silver (Ag), aluminum (Al), aluminum-lithium (Al—Li), calcium (Ca), magnesium-indium (Mg—In), magnesium-silver (Mg—Ag), or any combinations thereof may be used as a material for forming a first electrode 110.

The first electrode 110 may have a structure consisting of a single layer or a structure including multiple layers. For example, the first electrode 110 may have a three-layered structure of ITO/Ag/ITO.

[Interlayer 130]

The interlayer 130 may be disposed on the first electrode 110. The interlayer 130 may include an emission layer.

The interlayer 130 may further include a hole transport region between the first electrode 110 and the emission layer and an electron transport region between the emission layer and the second electrode 150.

The interlayer 130 may further include, in addition to various organic materials, metal-containing compounds such as organometallic compounds, inorganic materials such as quantum dots, and the like.

In embodiments, the interlayer 130 may include two or more light-emitting units sequentially stacked between the first electrode 110 and the second electrode 150 and a charge generation layer between the two or more emitting units. When the interlayer 130 includes the two or more emitting units and a charge generation layer as described above, the light-emitting device 10 may be a tandem light-emitting device.

[Hole Transport Region in Interlayer 130]

The hole transport region may have a structure consisting of a layer consisting of a single material, a structure consisting of a layer consisting of different materials, or a multi-layered structure including layers including different materials.

The hole transport region may include a hole injection layer, a hole transport layer, an emission auxiliary layer, an electron blocking layer, or any combination thereof.

For example, the hole transport region may have a multi-layered structure including a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein, in each structure, layers may be stacked from the first electrode 110 in its respective stated order.

The hole transport region may include a compound represented by Formula 201, a compound represented by Formula 202, or any combination thereof:

[Formula 201]

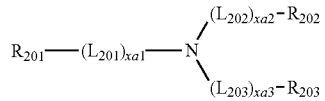

[Formula 202]

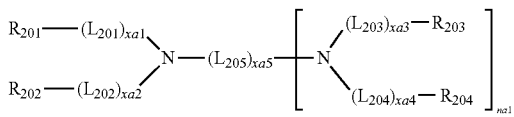 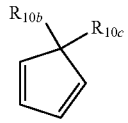

In Formulae 201 and 202,
$L_{201}$ to $L_{204}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$,
$L_{205}$ may be *—O—*', *—S—*', *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$,
xa1 to xa4 may each independently be an integer from 0 to 5,
xa5 may be an integer from 1 to 10,
$R_{201}$ to $R_{204}$ and $Q_{201}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$,
$R_{201}$ and $R_{202}$ may optionally be linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group (for example, a carbazole group or the like) unsubstituted or substituted with at least one $R_{10a}$ (for example, Compound HT16),
$R_{203}$ and $R_{204}$ may optionally be linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$, and
na1 may be an integer from 1 to 4.
In embodiments, each of Formulae 201 and 202 may include at least one of groups represented by Formulae CY201 to CY217.

CY201

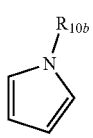

CY202

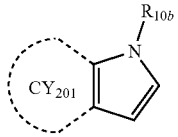

CY203

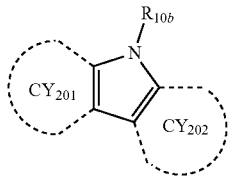

CY204

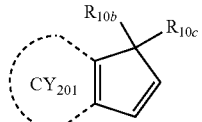

CY205

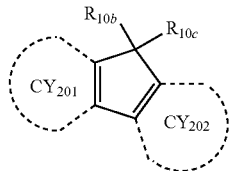

CY206

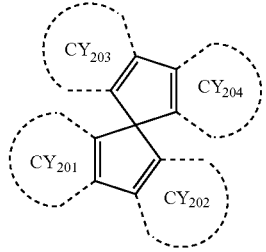

CY207

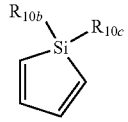

CY208

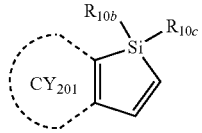

CY209

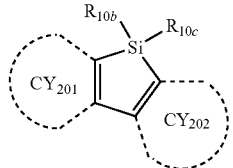

CY210

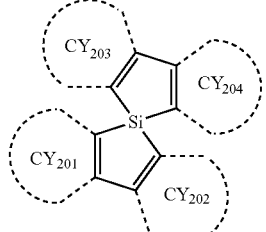

CY211

CY212

-continued

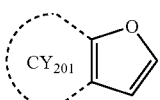
CY213

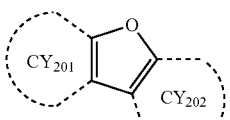
CY214

CY215

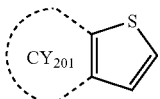
CY216

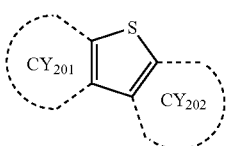
CY217

In Formulae CY201 to CY217, $R_{10b}$ and $R_{10c}$ may each independently be the same as described in connection with $R_{10a}$, ring CY201 to ring CY204 may each independently be a $C_3$-$C_{20}$ carbocyclic group or a $C_1$-$C_{20}$ heterocyclic group, and at least one hydrogen in Formulae CY201 to CY217 may be unsubstituted or substituted with $R_{10a}$.

In an embodiment, ring CY201 to ring CY204 in Formulae CY201 to CY217 may each independently be a benzene group, a naphthalene group, a phenanthrene group, or an anthracene group.

In embodiments, each of Formulae 201 and 202 may include at least one of groups represented by Formulae CY201 to CY203.

In embodiments, Formula 201 may include at least one of groups represented by Formulae CY201 to CY203 and at least one of groups represented by Formulae CY204 to CY217.

In embodiments, xa1 in Formula 201 may be 1, $R_{201}$ may be a group represented by one of Formulae CY201 to CY203, xa2 may be 0, and $R_{202}$ may be a group represented by one of Formulae CY204 to CY217.

In embodiments, each of Formulae 201 and 202 may not include a group represented by one of Formulae CY201 to CY203.

In embodiments, each of Formulae 201 and 202 may not include a group represented by one of Formulae CY201 to CY203, and may include at least one of groups represented by Formulae CY204 to CY217.

In embodiments, each of Formulae 201 and 202 may not include a group represented by one of Formulae CY201 to CY217.

In an embodiment, the hole transport region may include one of Compounds HT1 to HT46, m-MTDATA, TDATA, 2-TNATA, NPB(NPD), —NPB, TPD, Spiro-TPD, Spiro-NPB, methylated NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), or any combination thereof:

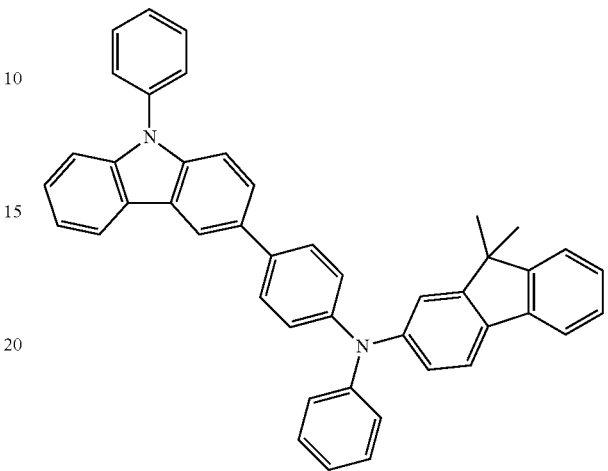
HT1

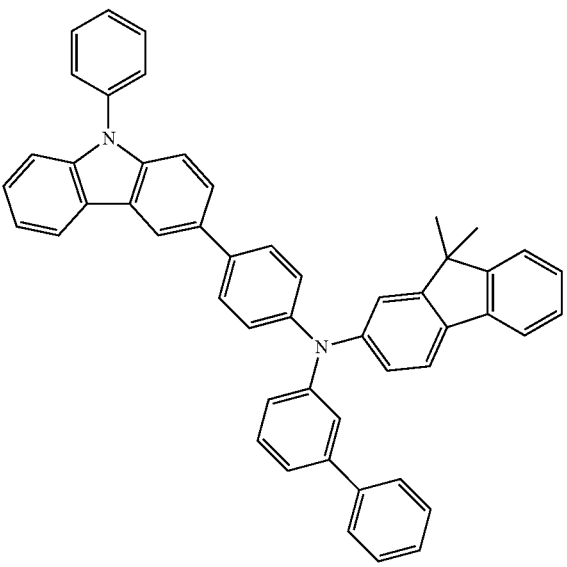
HT2

HT3
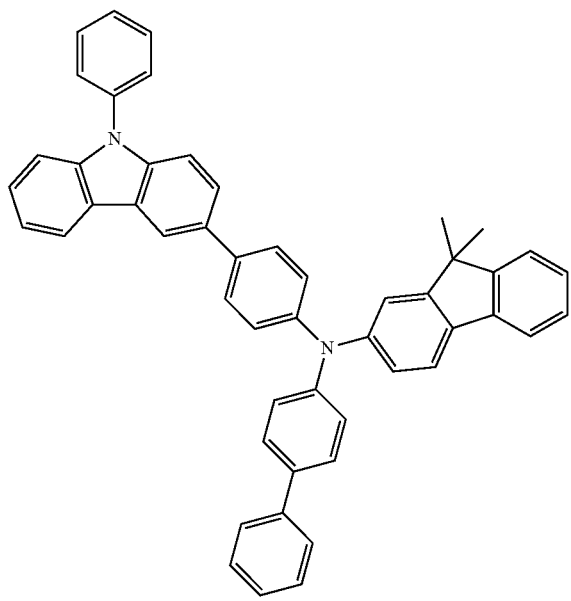
HT5
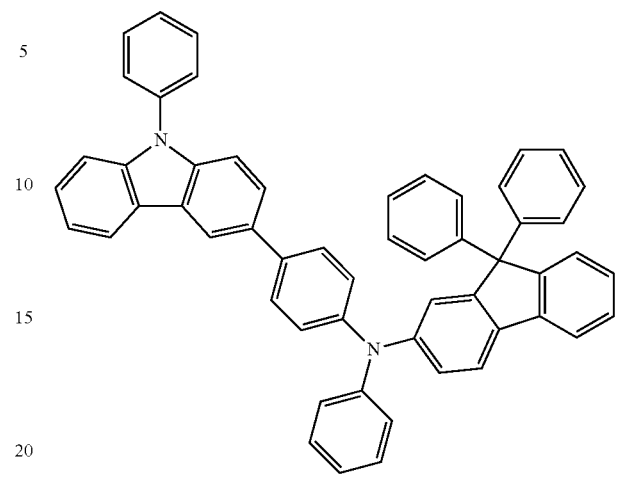
HT4
HT6
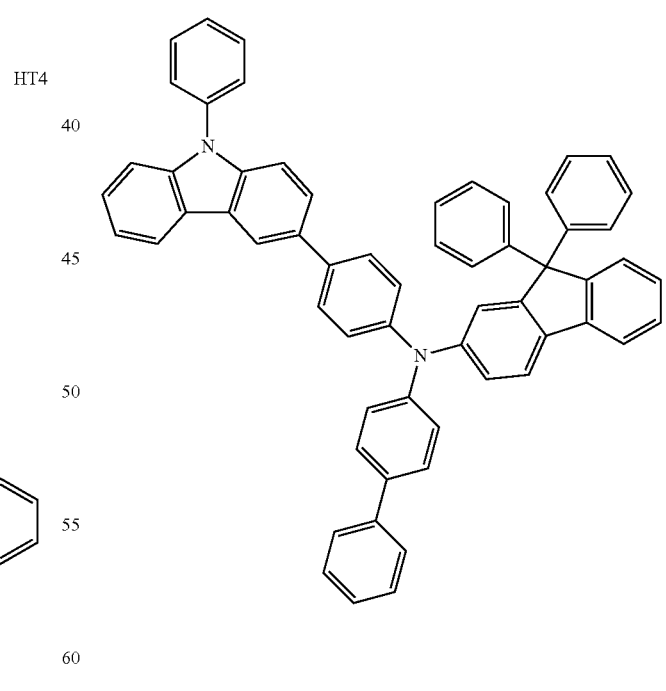

HT7
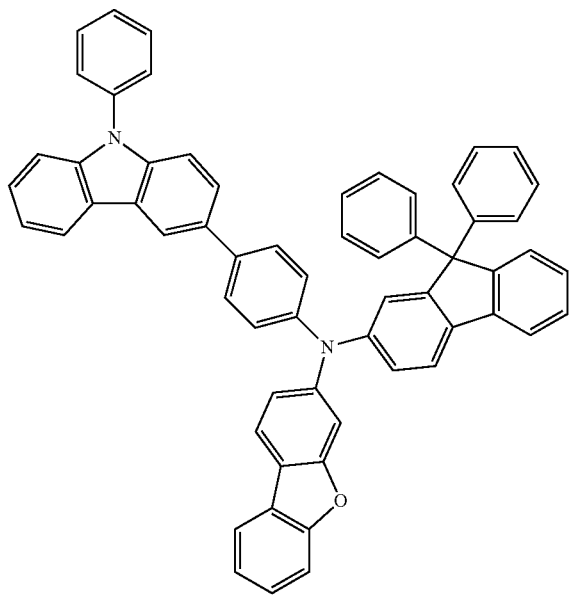
HT9
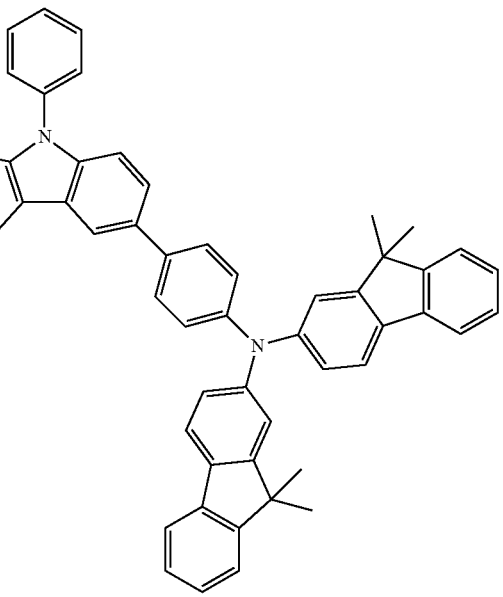
HT8
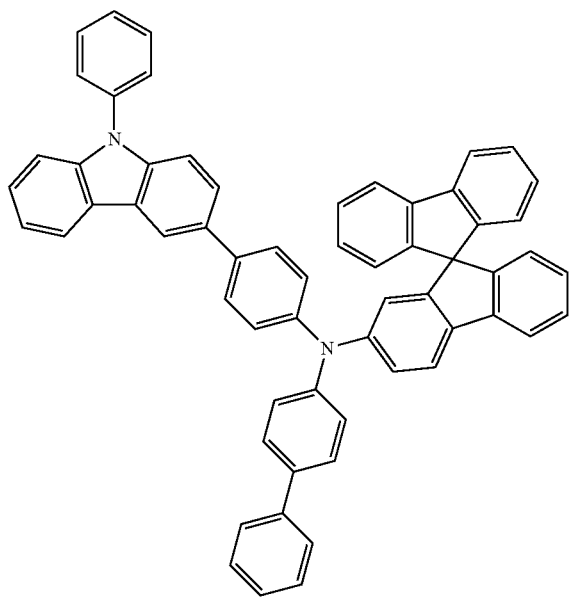
HT10
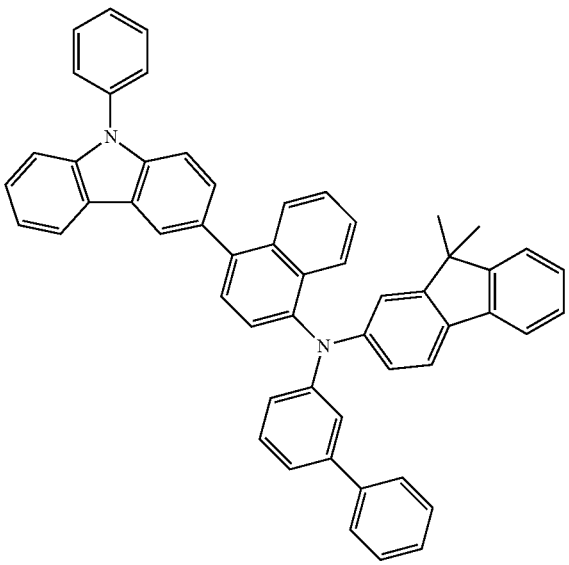

HT11
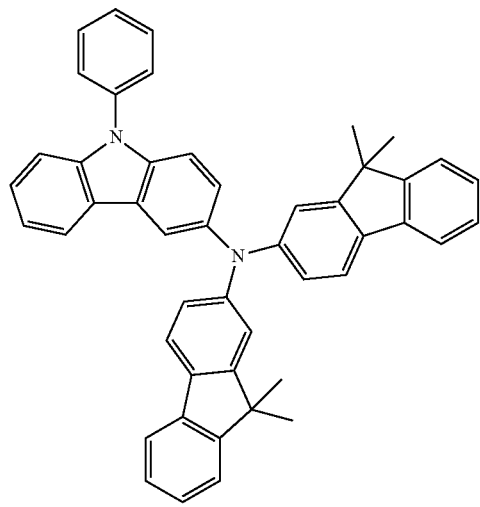
HT14
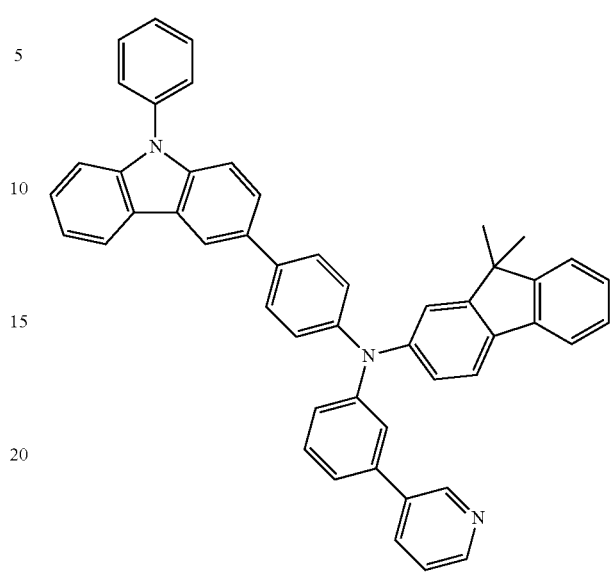
HT12
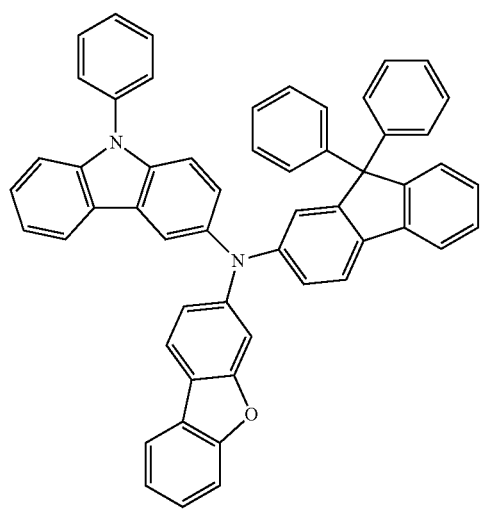
HT15
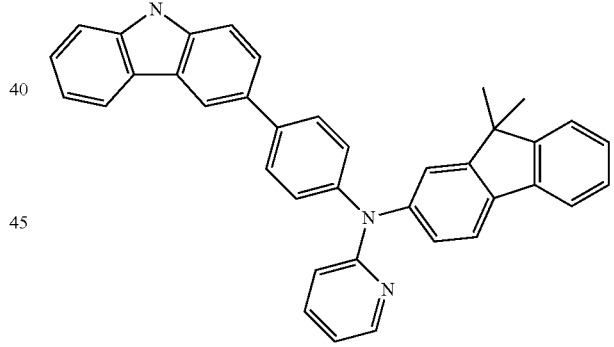
HT13
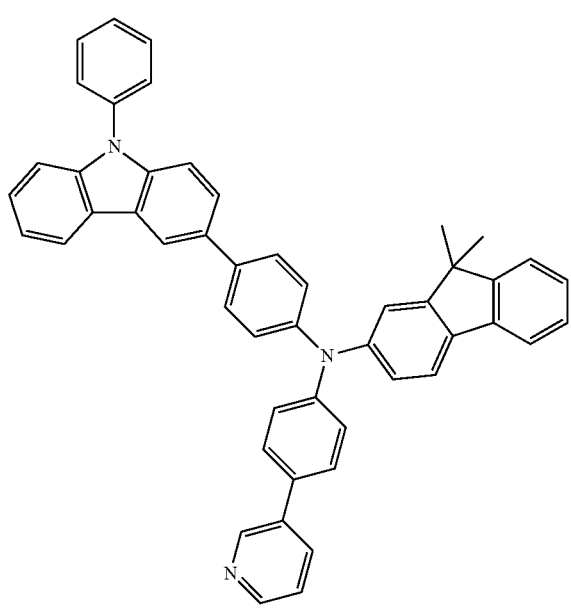
HT16
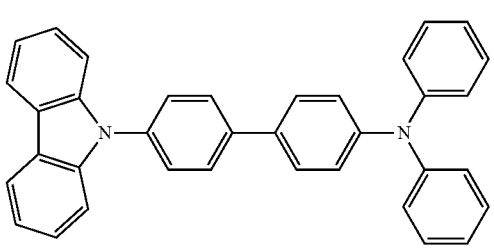

HT17
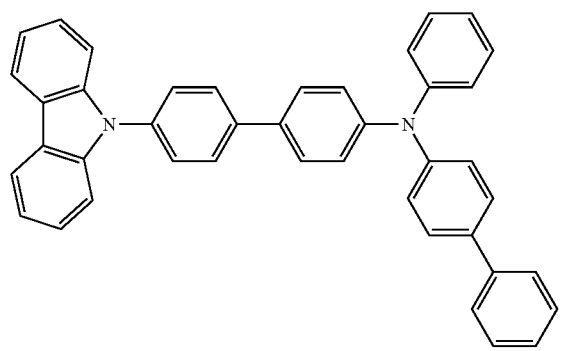
HT18
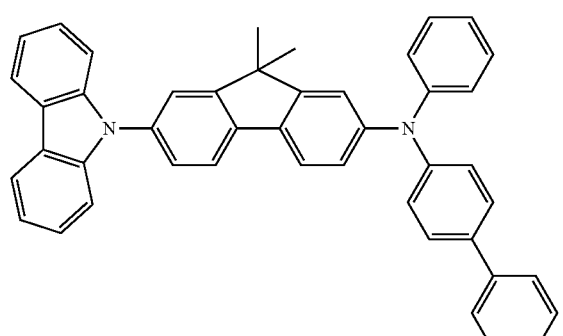
HT19
HT20
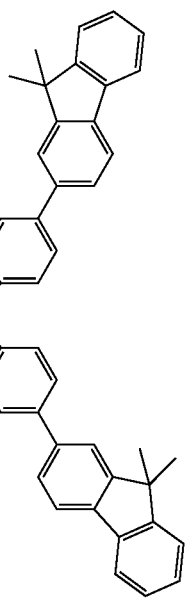
HT21
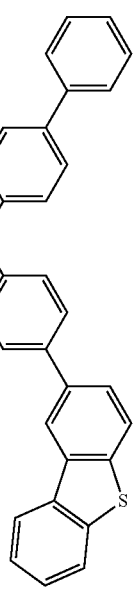
HT22
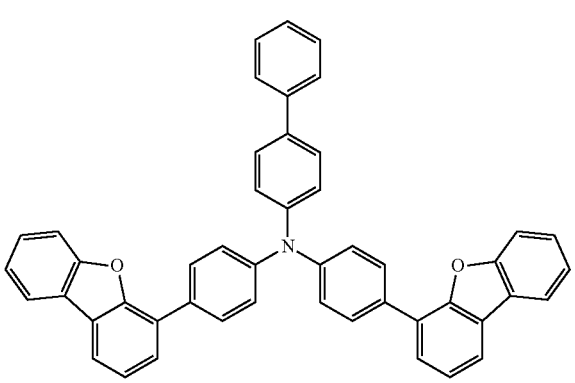

HT23
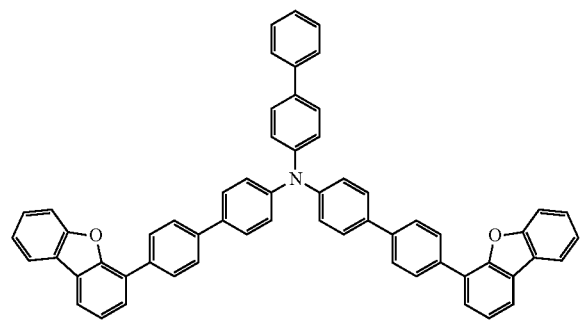
HT24
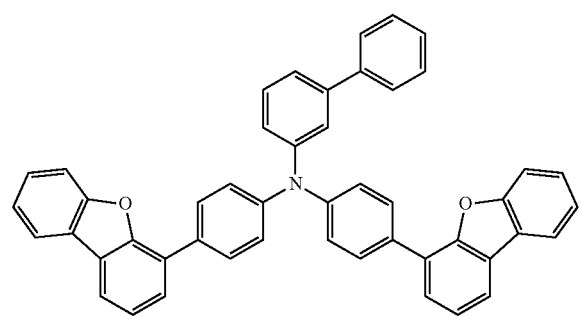
HT25
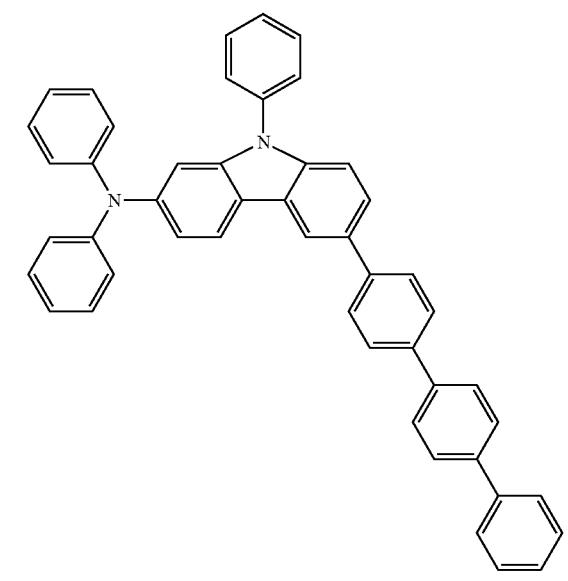
HT26
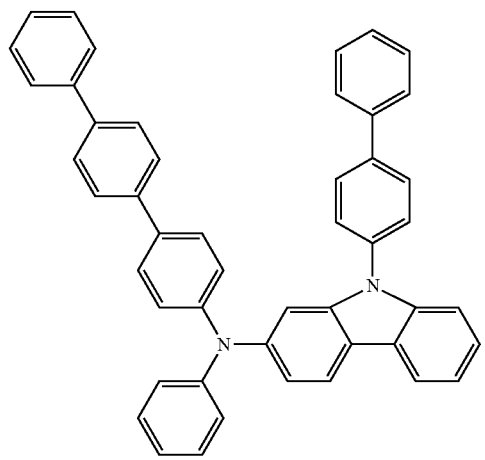
HT27
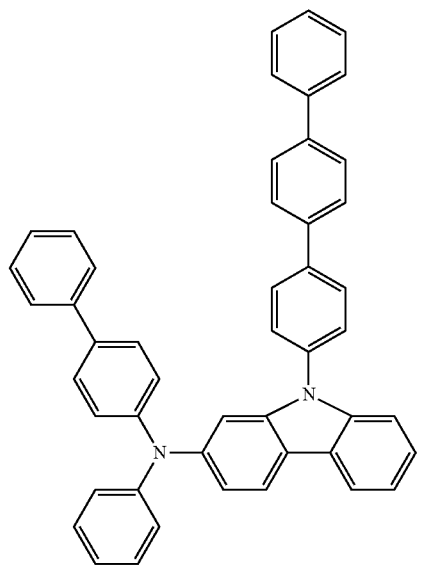
HT28
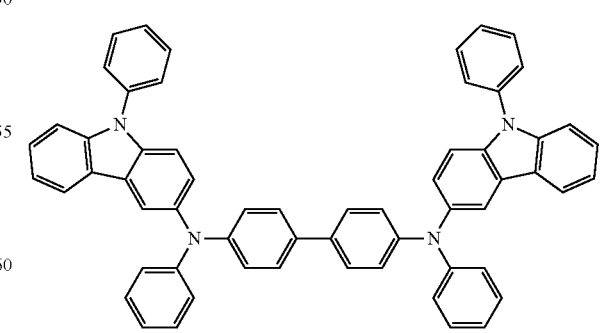

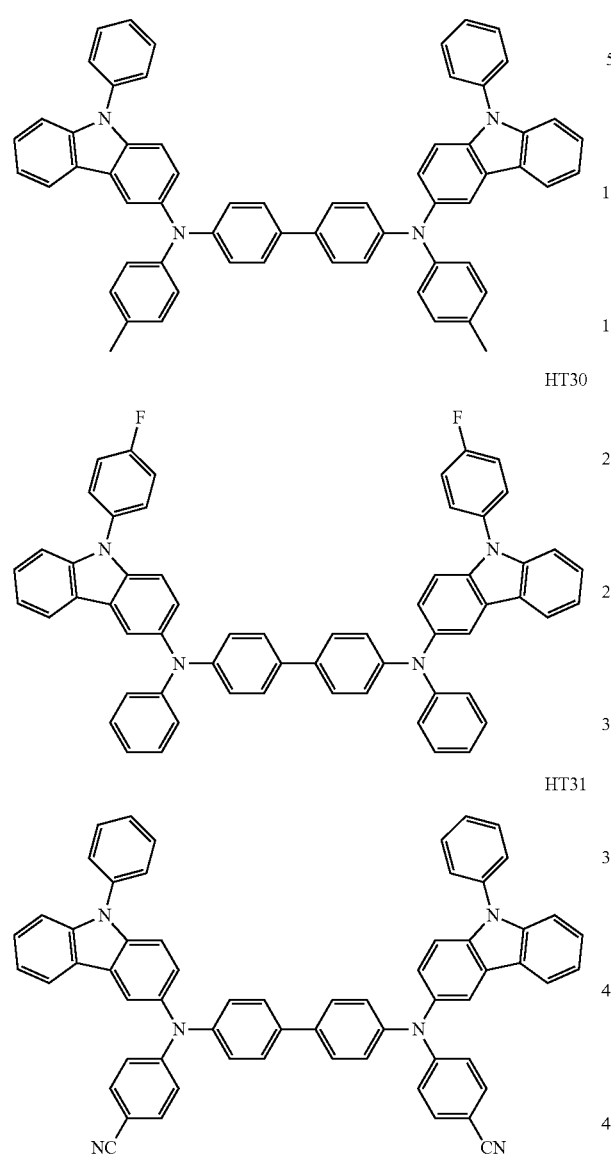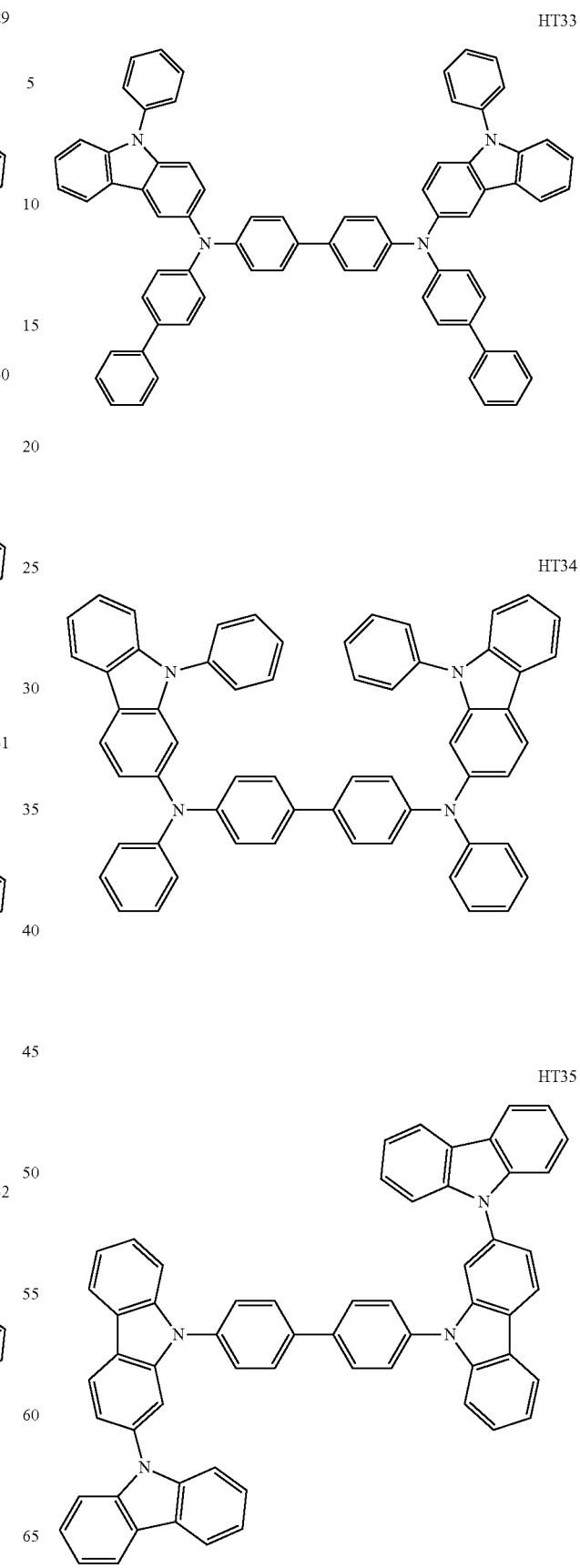

-continued
HT36
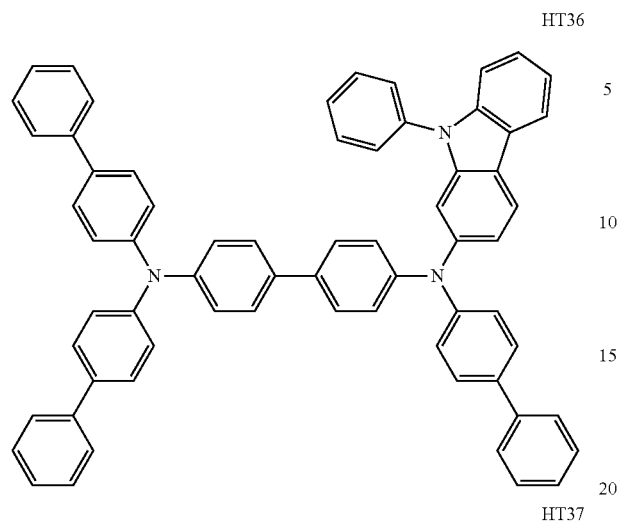
HT37
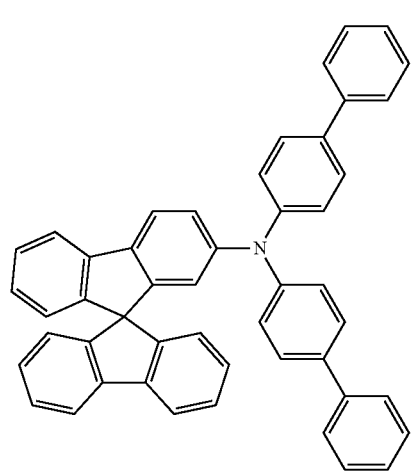
HT38
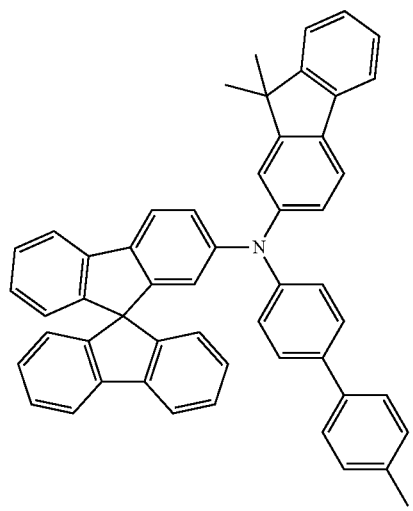
-continued
HT39
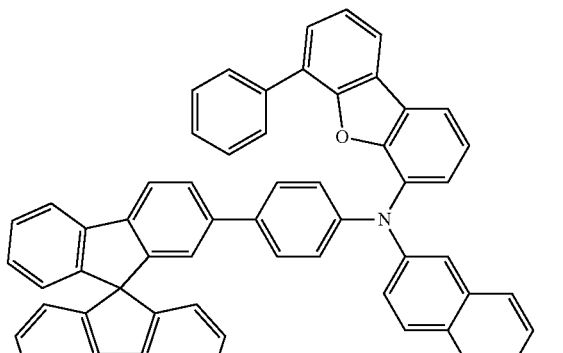
HT40
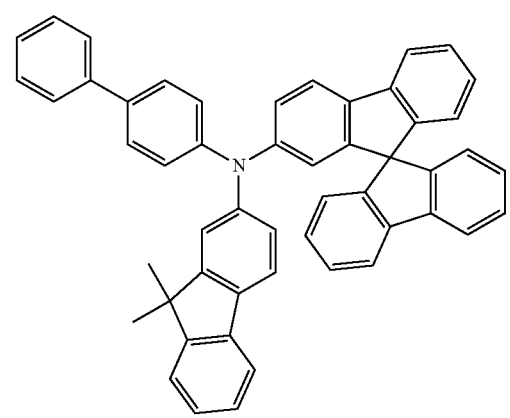
HT41
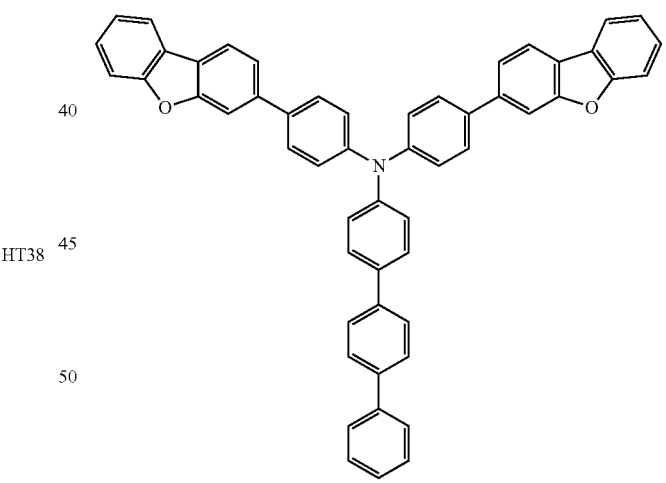
HT42
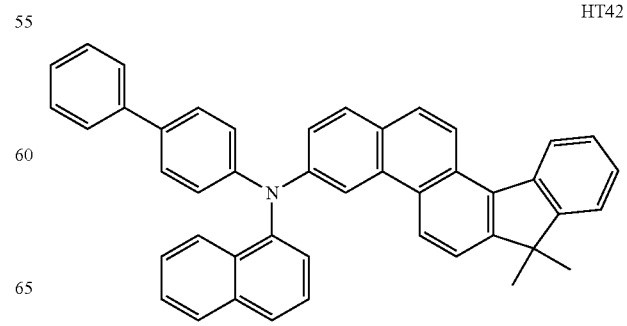

HT43
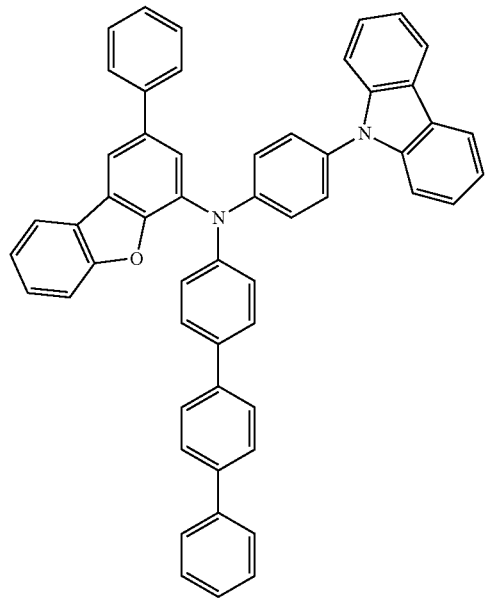
HT44
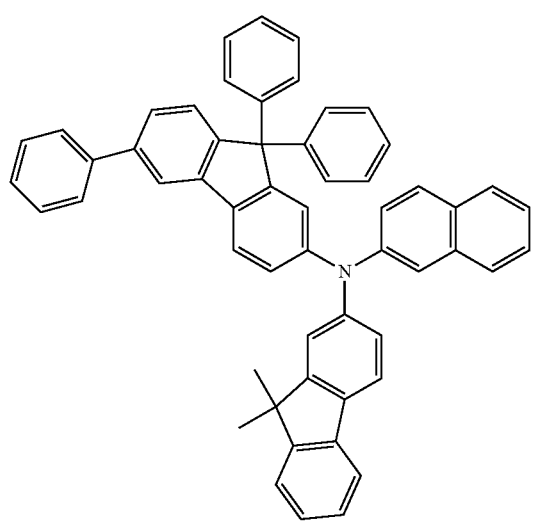
HT45
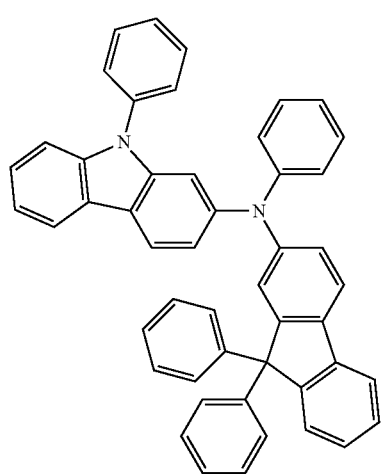
HT46
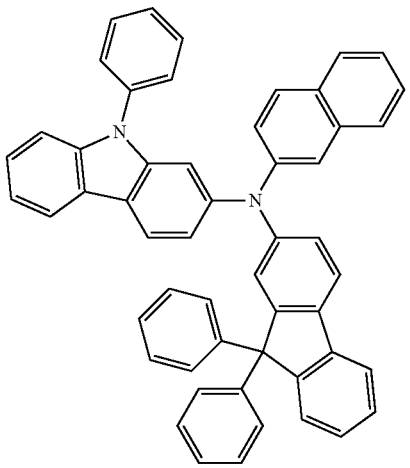
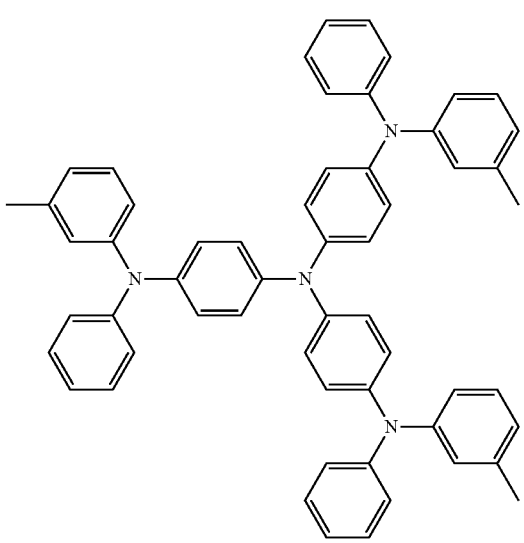
m-MTDATA
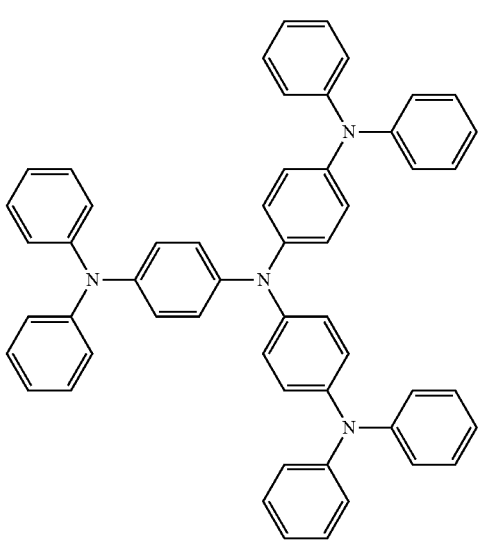
TDATA

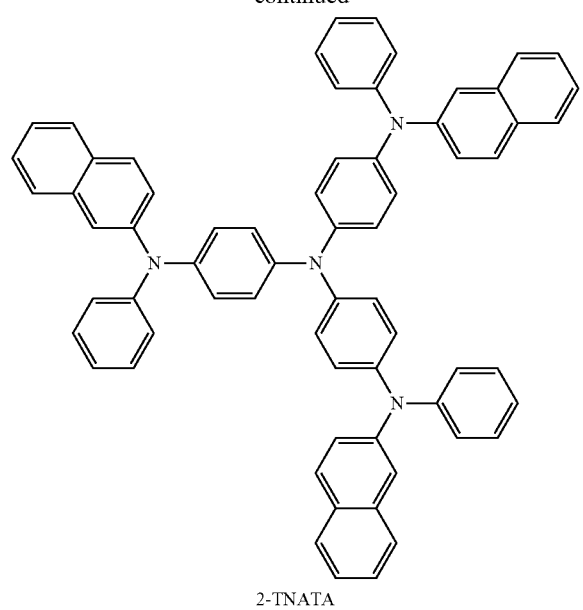
2-TNATA

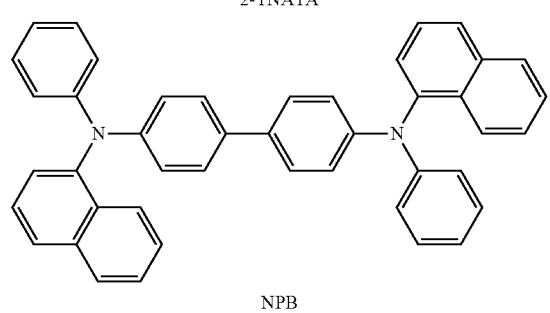
NPB

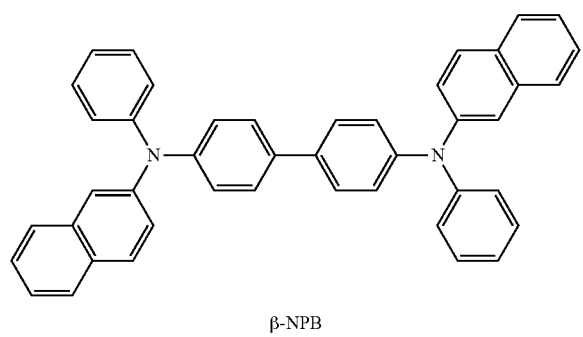
β-NPB

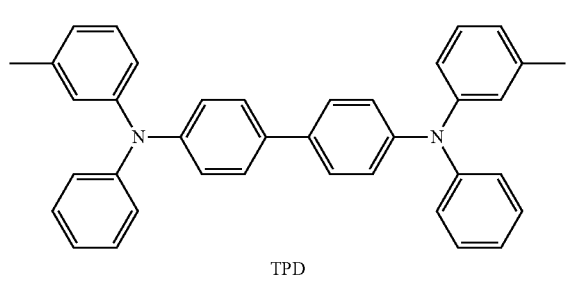
TPD

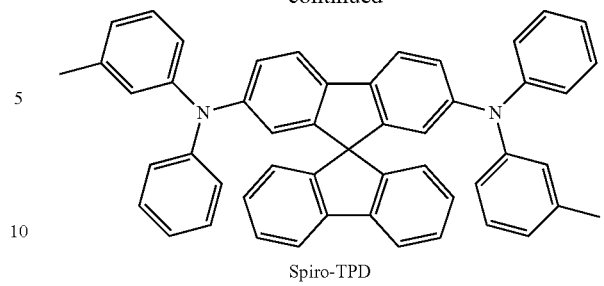
Spiro-TPD

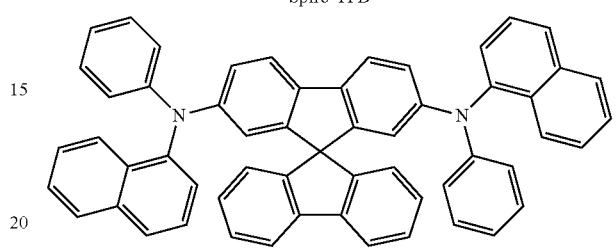
Spiro-NPB

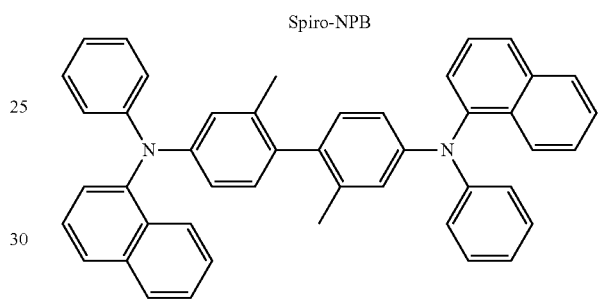
methylated-NPB

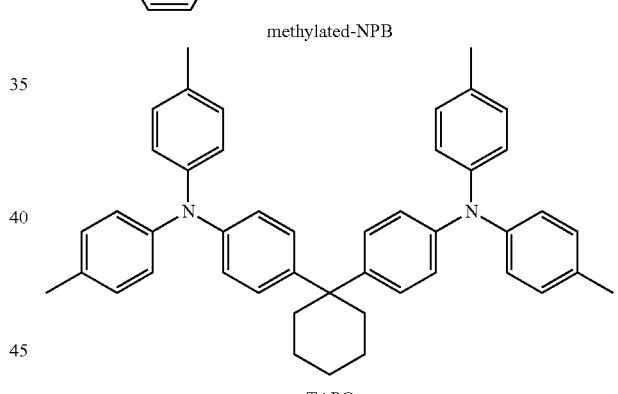
TAPC

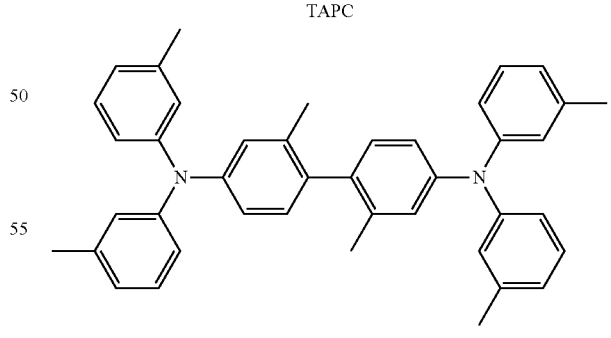
HMTPD

A thickness of the hole transport region may be in a range of about 50 Å to about 10,000 Å. For example, the thickness of the hole transport region may be in a range of about 100 Å to about 4,000 Å. When the hole transport region includes a hole injection layer, a hole transport layer, or any combination thereof, a thickness of the hole injection layer may be in a range of about 100 Å to about 9,000 Å, and a thickness of the hole transport layer may be in a range of about 50 Å to about 2,000 Å. For example, the thickness of the hole injection layer may be in a range of 100 Å to about 1,000 Å. For example, the thickness of the hole transport layer may be in a range of about 100 Å to about 1,500 Å. When the thicknesses of the hole transport region, the hole injection layer, and the hole transport layer are within these ranges, satisfactory hole transporting characteristics may be obtained without a substantial increase in driving voltage.

The emission auxiliary layer may increase light-emission efficiency by compensating for an optical resonance distance according to a wavelength of light emitted by an emission layer, and the electron blocking layer may block the leakage of electrons from an emission layer to a hole transport region. Materials that may be included in the hole transport region may be included in the emission auxiliary layer and the electron blocking layer.

[p-Dopant]

The hole transport region may further include, in addition to these materials, a charge-generation material for the improvement of conductive properties. The charge-generation material may be uniformly or non-uniformly dispersed in the hole transport region (for example, in the form of a single layer consisting of a charge-generation material).

The charge-generation material may be, for example, a p-dopant.

In embodiments, the lowest unoccupied molecular orbital (LUMO) energy level of the p-dopant may be equal to or less than about −3.5 eV.

In embodiments, the p-dopant may include a quinone derivative, a cyano group-containing compound, a compound containing element EL1 and element EL2, or any combination thereof.

Examples of the quinone derivative may include TCNQ, F4-TCNQ, etc.

Examples of the cyano group-containing compound may include HAT-CN, and a compound represented by Formula 221 below.

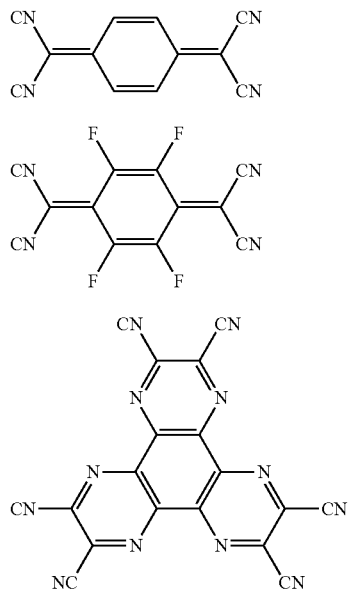

TCNQ

F4-TCNQ

HAT-CN

-continued

[Formula 221]

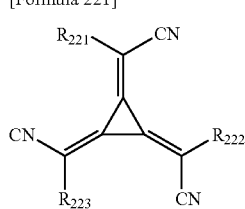

In Formula 221, $R_{221}$ to $R_{223}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and at least one of $R_{221}$ to $R_{223}$ may each independently be a $C_3$-$C_{60}$ carbocyclic group or a $C_1$-$C_{60}$ heterocyclic group, each substituted with a cyano group; —F; —Cl; —Br; —I; a $C_1$-$C_{20}$ alkyl group substituted with a cyano group, —F, —Cl, —Br, —I, or any combination thereof, or any combination thereof.

In the compound containing element EL1 and element EL2, element EL1 may be a metal, a metalloid, or any combination thereof, and element EL2 may be a non-metal, a metalloid, or any combination thereof.

Examples of the metal may include an alkali metal (for example, lithium (Li), sodium (Na), potassium (K), rubidium (Rb), cesium (Cs), etc.); an alkaline earth metal (for example, beryllium (Be), magnesium (Mg), calcium (Ca), strontium (Sr), barium (Ba), etc.); a transition metal (for example, titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au), etc.); a post-transition metal (for example, zinc (Zn), indium (In), tin (Sn), etc.); and a lanthanide metal (for example, lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), etc.).

Examples of the metalloid may include silicon (Si), antimony (Sb), and tellurium (Te).

Examples of the non-metal may oxygen (O) and a halogen (for example, F, Cl, Br, I, etc.).

In embodiments, examples of the compound containing element EL1 and element EL2 may include a metal oxide, a metal halide (for example, metal fluoride, metal chloride, metal bromide, or metal iodide), a metalloid halide (for example, metalloid fluoride, metalloid chloride, metalloid bromide, or metalloid iodide), a metal telluride, or any combination thereof.

Examples of the metal oxide may include tungsten oxide (for example, WO, $W_2O_3$, $WO_2$, $WO_3$, $W_2O_5$, etc.), vanadium oxide (for example, VO, $V_2O_3$, $VO_2$, $V_2O_5$, etc.), molybdenum oxide (MoO, $Mo_2O_3$, $MoO_2$, $MoO_3$, $Mo_2O_5$, etc.), and rhenium oxide (for example, $ReO_3$, etc.).

Examples of the metal halide may include an alkali metal halide, an alkaline earth metal halide, a transition metal halide, a post-transition metal halide, and a lanthanide metal halide.

Examples of the alkali metal halide may include LiF, NaF, KF, RbF, CsF, LiCl, NaCl, KCl, RbCl, CsCl, LiBr, NaBr, KBr, RbBr, CsBr, LiI, NaI, KI, RbI, and CsI.

Examples of the alkaline earth metal halide may include $BeF_2$, $MgF_2$, $CaF_2$, $SrF_2$, $BaF_2$, $BeCl_2$, $MgCl_2$, $CaCl_2$, $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, and $BaI_2$.

Examples of the transition metal halide may titanium halide (for example, $TiF_4$, $TiCl_4$, $TiBr_4$, $TiI_4$, etc.), zirconium halide (for example, $ZrF_4$, $ZrCl_4$, $ZrBr_4$, $ZrI_4$, etc.), hafnium halide (for example, $HfF_4$, $HfCl_4$, $HfBr_4$, $HfI_4$, etc.), vanadium halide (for example, $VF_3$, $VCl_3$, $VBr_3$, $VI_3$, etc.), niobium halide (for example, $NbF_3$, $NbCl_3$, $NbBr_3$, $NbI_3$, etc.), tantalum halide (for example, $TaF_3$, $TaCl_3$, $TaBr_3$, $TaI_3$, etc.), chromium halide (for example, $CrF_3$, $CrCl_3$, $CrBr_3$, $CrI_3$, etc.), molybdenum halide (for example, $MoF_3$, $MoCl_3$, $MoBr_3$, $MoI_3$, etc.), tungsten halide (for example, $WF_3$, $WCl_3$, $WBr_3$, $WI_3$, etc.), manganese halide (for example, $MnF_2$, $MnCl_2$, $MnBr_2$, $MnI_2$, etc.), technetium halide (for example, $TcF_2$, $TcCl_2$, $TcBr_2$, $TcI_2$, etc.), rhenium halide (for example, $ReF_2$, $ReCl_2$, $ReBr_2$, $ReI_2$, etc.), iron halide (for example, $FeF_2$, $FeCl_2$, $FeBr_2$, $FeI_2$, etc.), ruthenium halide (for example, $RuF_2$, $RuCl_2$, $RuBr_2$, $RuI_2$, etc.), osmium halide (for example, $OsF_2$, $OsCl_2$, $OsBr_2$, $OsI_2$, etc.), cobalt halide (for example, $CoF_2$, $CoCl_2$, $CoBr_2$, $CoI_2$, etc.), rhodium halide (for example, $RhF_2$, $RhCl_2$, $RhBr_2$, $RhI_2$, etc.), iridium halide (for example, $IrF_2$, $IrCl_2$, $IrBr_2$, $IrI_2$, etc.), nickel halide (for example, $NiF_2$, $NiCl_2$, $NiBr_2$, $NiI_2$, etc.), palladium halide (for example, $PdF_2$, $PdCl_2$, $PdBr_2$, $PdI_2$, etc.), platinum halide (for example, $PtF_2$, $PtCl_2$, $PtBr_2$, $PtI_2$, etc.), copper halide (for example, $CuF$, $CuCl$, $CuBr$, $CuI$, etc.), silver halide (for example, $AgF$, $AgCl$, $AgBr$, $AgI$, etc.), and gold halide (for example, $AuF$, $AuCl$, $AuBr$, $AuI$, etc.).

Examples of the post-transition metal halide may include zinc halide (for example, $ZnF_2$, $ZnCl_2$, $ZnBr_2$, $ZnI_2$, etc.), indium halide (for example, $InI_3$, etc.), and tin halide (for example, $SnI_2$, etc.).

Examples of the lanthanide metal halide may include $YbF$, $YbF_2$, $YbF_3$, $SmF_3$, $YbCl$, $YbCl_2$, $YbCl_3$ $SmCl_3$, $YbBr$, $YbBr_2$, $YbBr_3$ $SmBr_3$, $YbI$, $YbI_2$, $YbI_3$, and $SmI_3$.

An example of the metalloid halide may include antimony halide (for example, $SbCl_5$, etc.).

Examples of the metal telluride may include an alkali metal telluride (for example, $Li_2Te$, $Na_2Te$, $K_2Te$, $Rb_2Te$, $Cs_2Te$, etc.), an alkaline earth metal telluride (for example, $BeTe$, $MgTe$, $CaTe$, $SrTe$, $BaTe$, etc.), a transition metal telluride (for example, $TiTe_2$, $ZrTe_2$, $HfTe_2$, $V_2Te_3$, $Nb_2Te_3$, $Ta_2Te_3$, $Cr_2Te_3$, $Mo_2Te_3$, $W_2Te_3$, $MnTe$, $TcTe$, $ReTe$, $FeTe$, $RuTe$, $OsTe$, $CoTe$, $RhTe$, $IrTe$, $NiTe$, $PdTe$, $PtTe$, $Cu_2Te$, $CuTe$, $Ag_2Te$, $AgTe$, $Au_2Te$, etc.), a post-transition metal telluride (for example, $ZnTe$, etc.), and a lanthanide metal telluride (for example, $LaTe$, $CeTe$, $PrTe$, $NdTe$, $PmTe$, $EuTe$, $GdTe$, $TbTe$, $DyTe$, $HoTe$, $ErTe$, $TmTe$, $YbTe$, $LuTe$, etc.).

[Emission Layer in Interlayer 130]

When the light-emitting device 10 is a full-color light-emitting device, the emission layer may be patterned into a red emission layer, a green emission layer, and/or a blue emission layer, according to a subpixel. In embodiments, the emission layer may have a stacked structure of two or more layers of a red emission layer, a green emission layer, and a blue emission layer, in which the two or more layers may contact each other or may be separated from each other. In embodiments, the emission layer may include two or more materials of a red light-emitting material, a green light-emitting material, and a blue light-emitting material, in which the two or more materials are mixed with each other in a single layer to emit white light.

The emission layer may include a host and a dopant. The dopant may include a phosphorescent dopant, a fluorescent dopant, or any combination thereof.

An amount of the dopant in the emission layer may be in a range of about 0.01 to about 15 parts by weight based on 100 parts by weight of the host.

In embodiments, the emission layer may include a quantum dot.

The emission layer may include a delayed fluorescence material. The delayed fluorescence material may act as a host or a dopant in the emission layer.

A thickness of the emission layer may be in a range of about 100 Å to about 1,000 Å. For example, the thickness of the emission layer may be in a range of about 200 Å to about 600 Å. When the thickness of the emission layer is within these ranges, excellent light-emission characteristics may be obtained without a substantial increase in driving voltage.

[Host]

In embodiments, the host may include a compound represented by Formula 301 below:

$[Ar_{301}]_{xb11}$-$[(L_{301})_{xb1}$-$R_{301}]_{xb21}$      [Formula 301]

In Formula 301, $Ar_{301}$ and $L_{301}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xb11 may be 1, 2, or 3, xb1 may be an integer from 0 to 5, $R_{301}$ may be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), or —P(=O)($Q_{301}$)($Q_{302}$), xb21 may be an integer from 1 to 5, and $Q_{301}$ to $Q_{303}$ may each independently be the same as described in connection with Qi.

For example, when xb11 in Formula 301 is 2 or more, two or more of $Ar_{301}$(s) may be linked to each other via a single bond.

In embodiments, the host may include a compound represented by Formula 301-1, a compound represented by Formula 301-2, or any combination thereof:

[Formula 301-1]

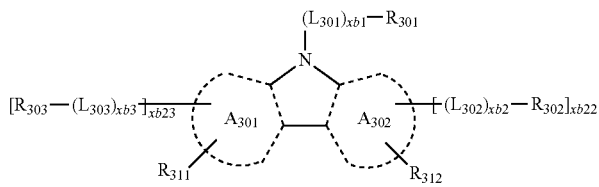

[Formula 301-2]

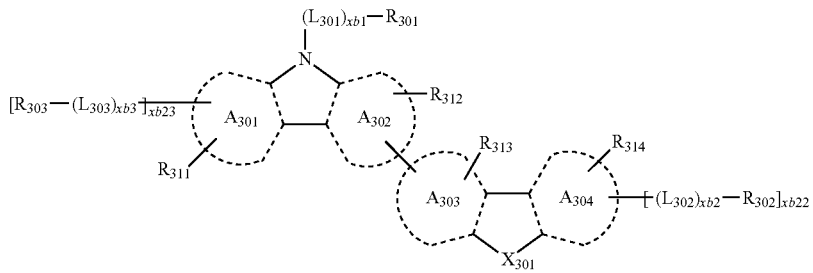

In Formulae 301-1 and 301-2,
ring $A_{301}$ to ring $A_{304}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$,
$X_{301}$ may be O, S, N-[$(L_{304})_{xb4}$-$R_{304}$], C($R_{304}$)($R_{305}$), or Si($R_{304}$)($R_{305}$),
xb22 and xb23 may each independently be 0, 1, or 2,
$L_{301}$, xb1, and $R_{301}$ may each respectively be the same as described in connection with $L_{301}$, xb1, and $R_{301}$ as provided in the specification,
$L_{302}$ to $L_{304}$ may each independently be the same as described in connection with $L_{301}$,
xb2 to xb4 may each independently be the same as described in connection with xb1, and
$R_{302}$ to $R_{305}$ and $R_{311}$ to $R_{314}$ may each independently be the same as described in connection with $R_{301}$ in the specification.

In embodiments, the host may include an alkali earth metal complex, a post-transition metal complex, or any combination thereof. In embodiments, the host may include a Be complex (for example, Compound H55), an Mg complex, a Zn complex, or any combination thereof.

In an embodiment, the host may include one of Compounds H1 to H126, 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), or any combination thereof:

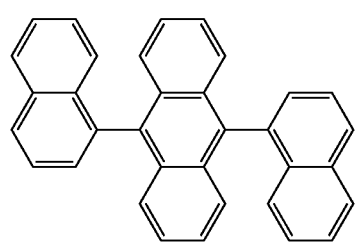
H1

-continued

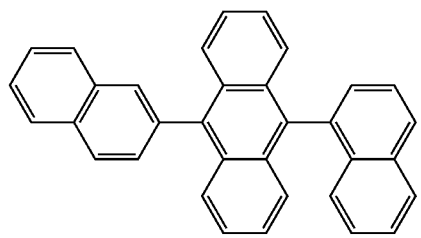
H2

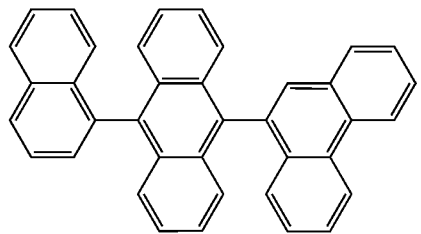
H3

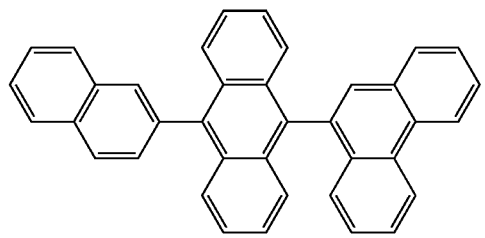
H4

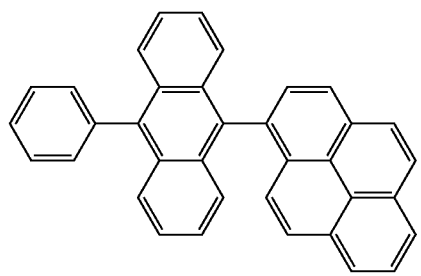
H5

H6
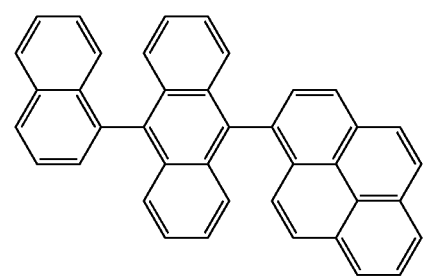
H7
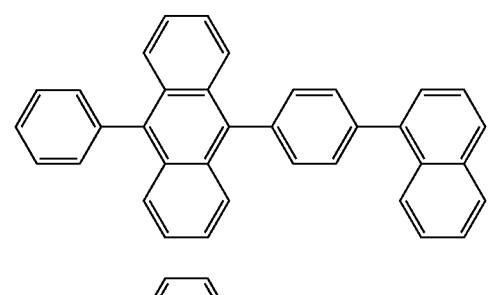
H8
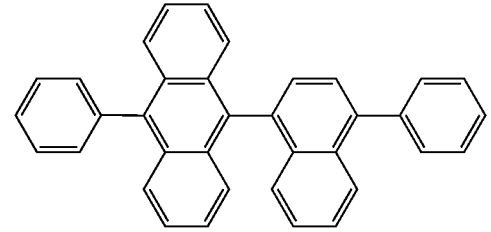
H9
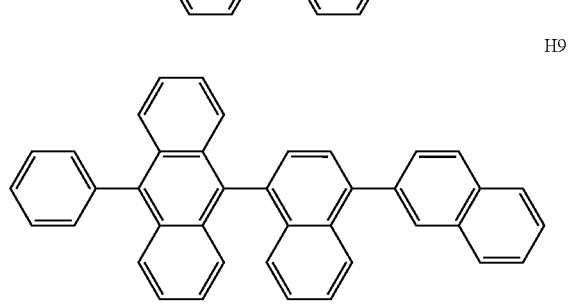
H10
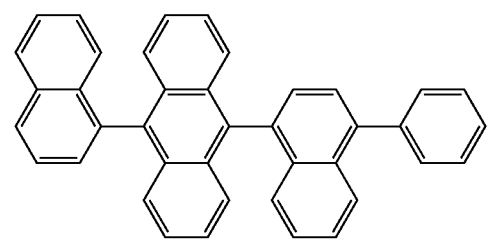
H11
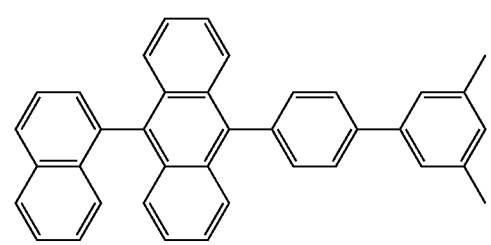
H12
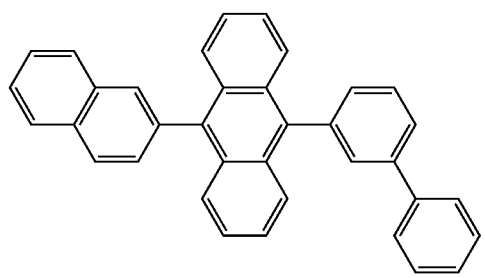
H13
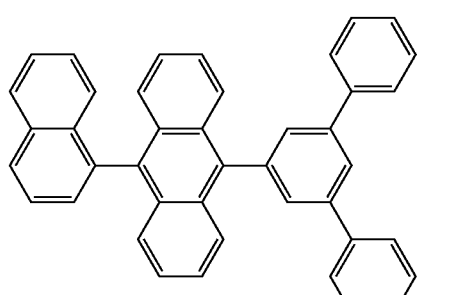
H14
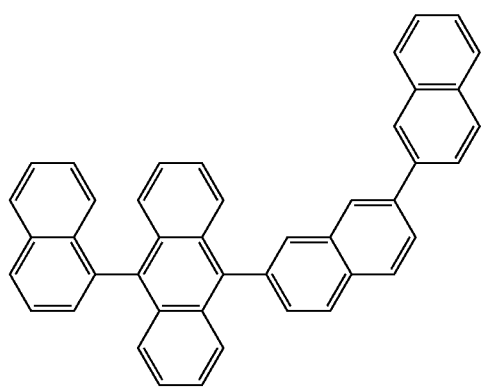
H15
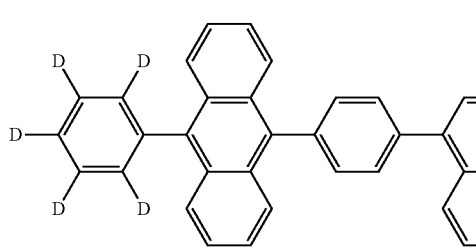
H16
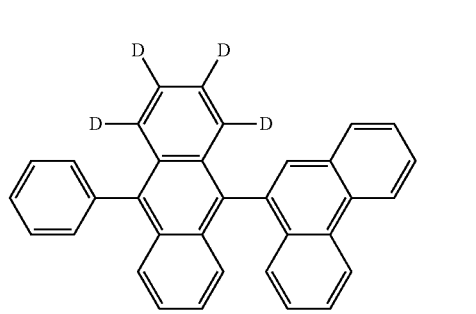

H17
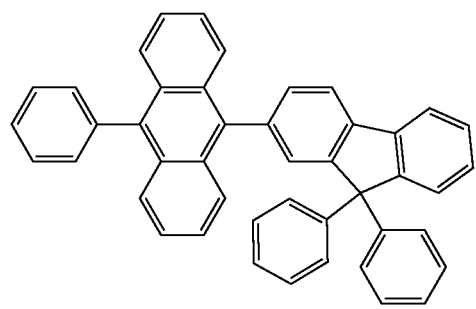
H18
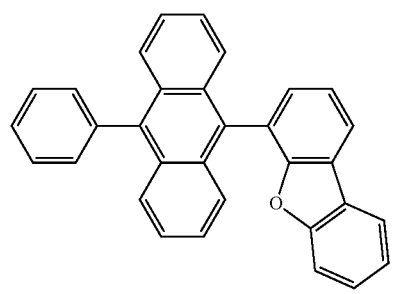
H19
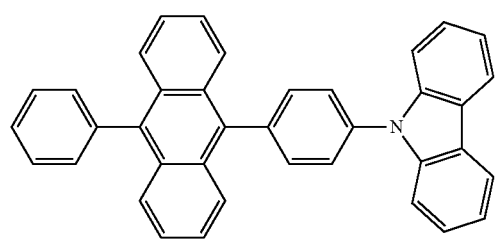
H20
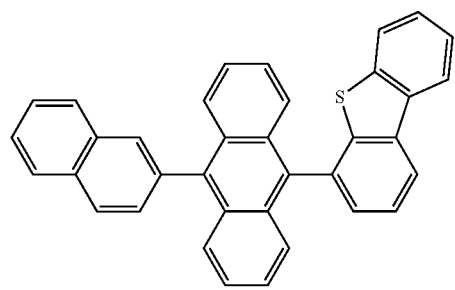
H21
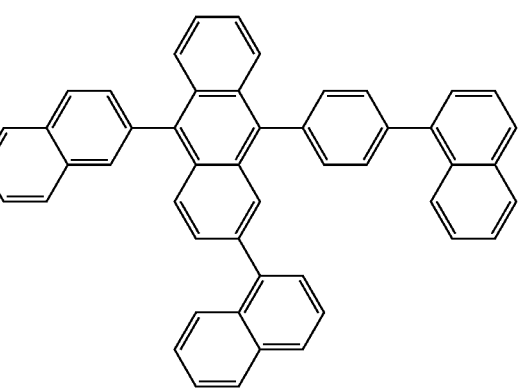
H22
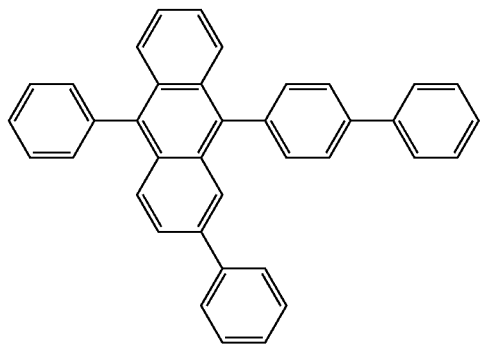
H23
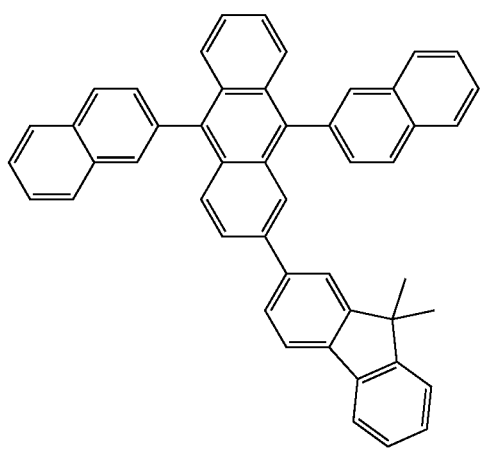
H24
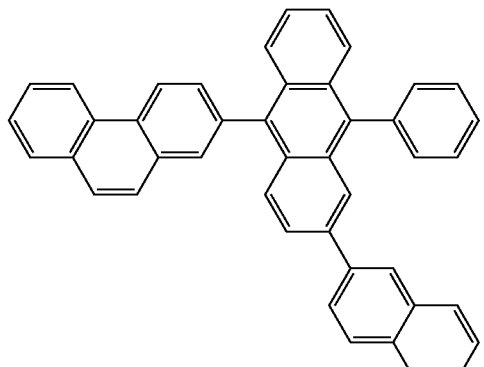

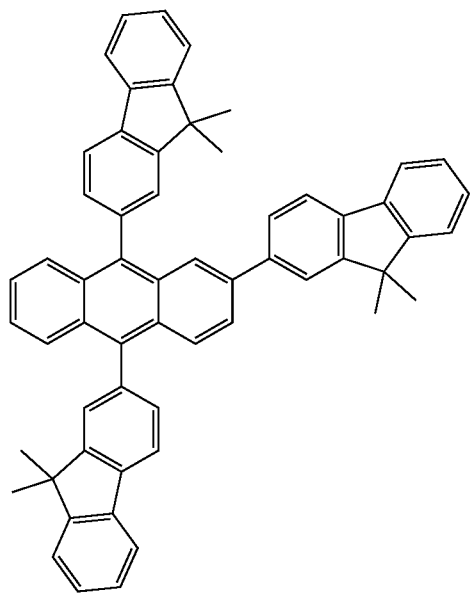
H25
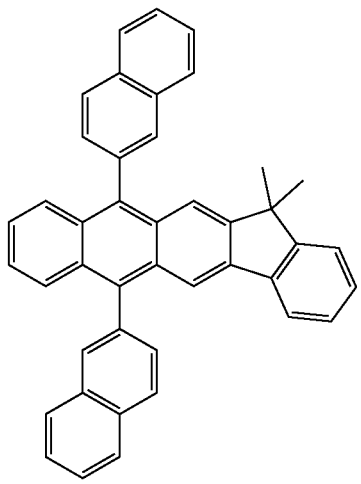
H27
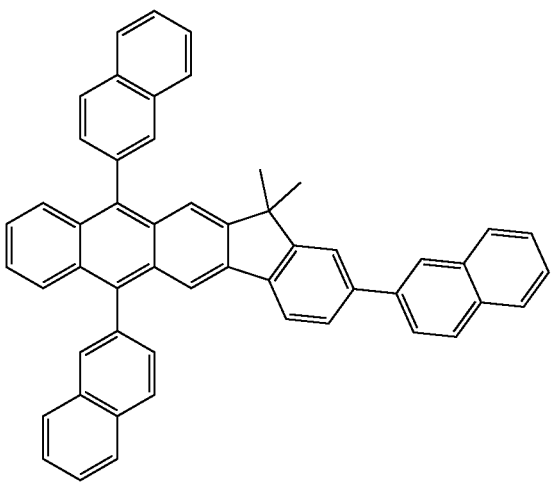
H28
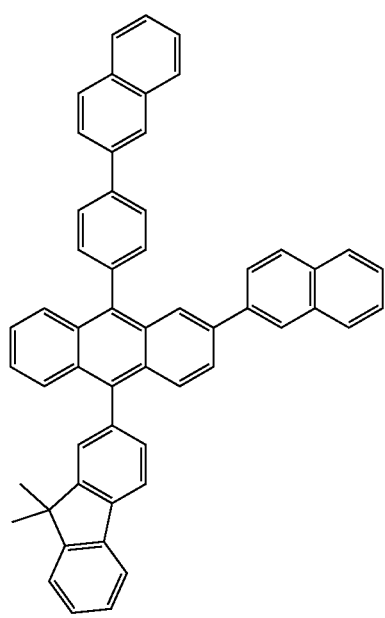
H26
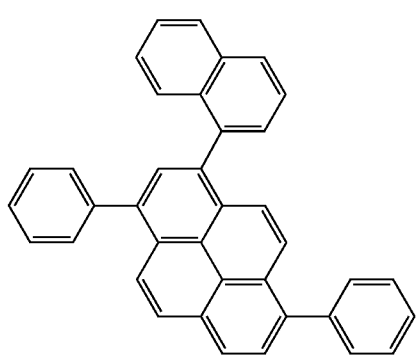
H29

H30
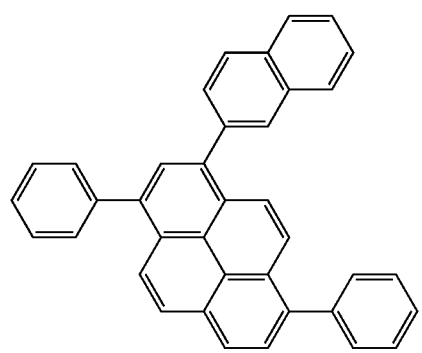
H31
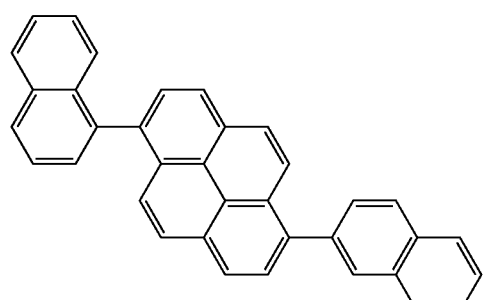
H32
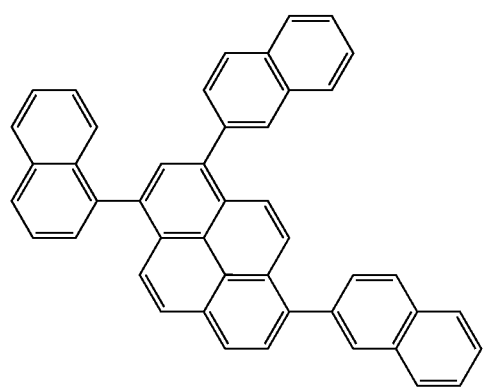
H33
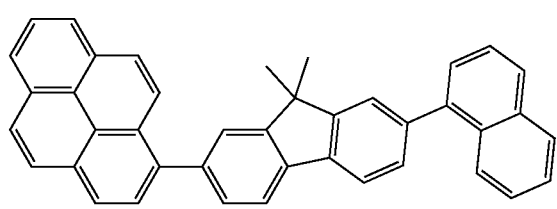
H34
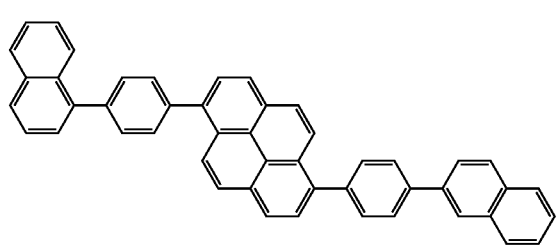
H35
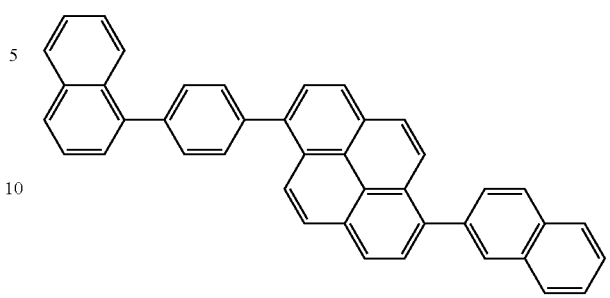
H36
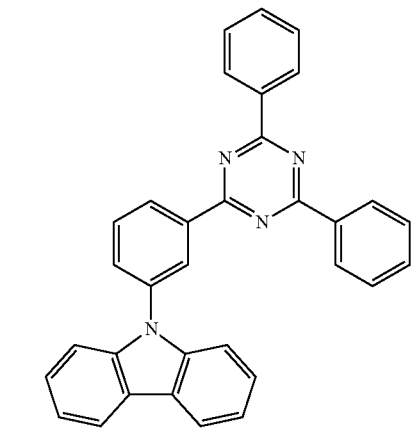
H37
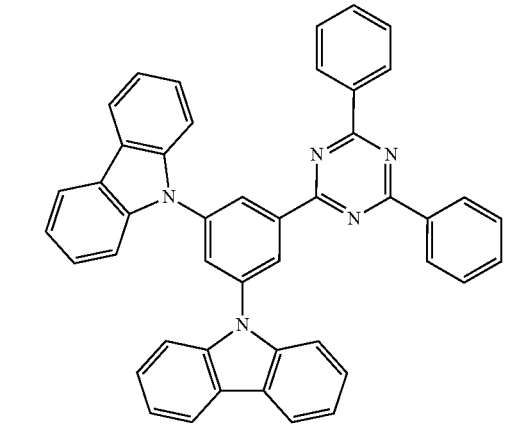
H38
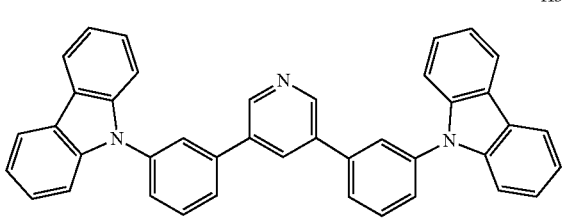

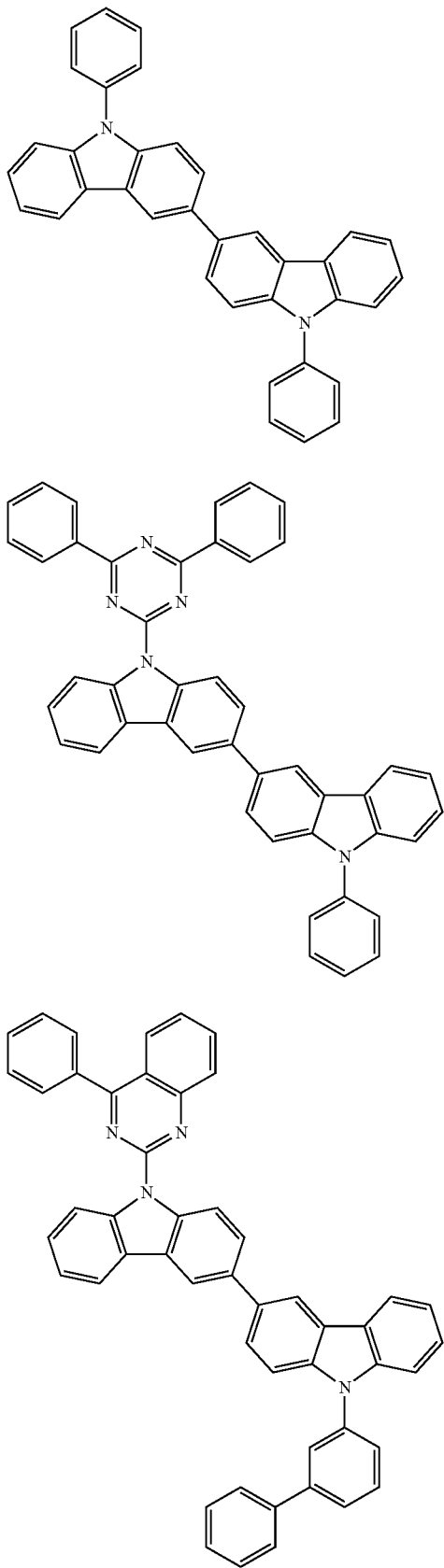
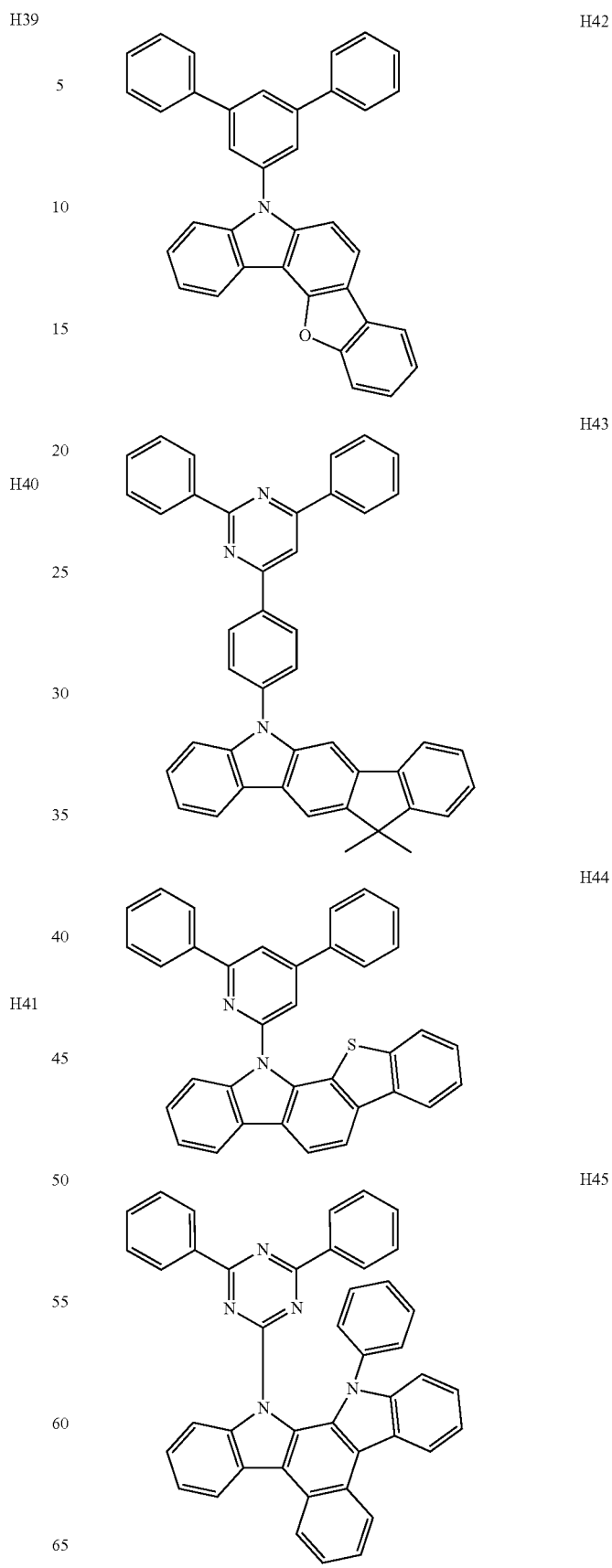

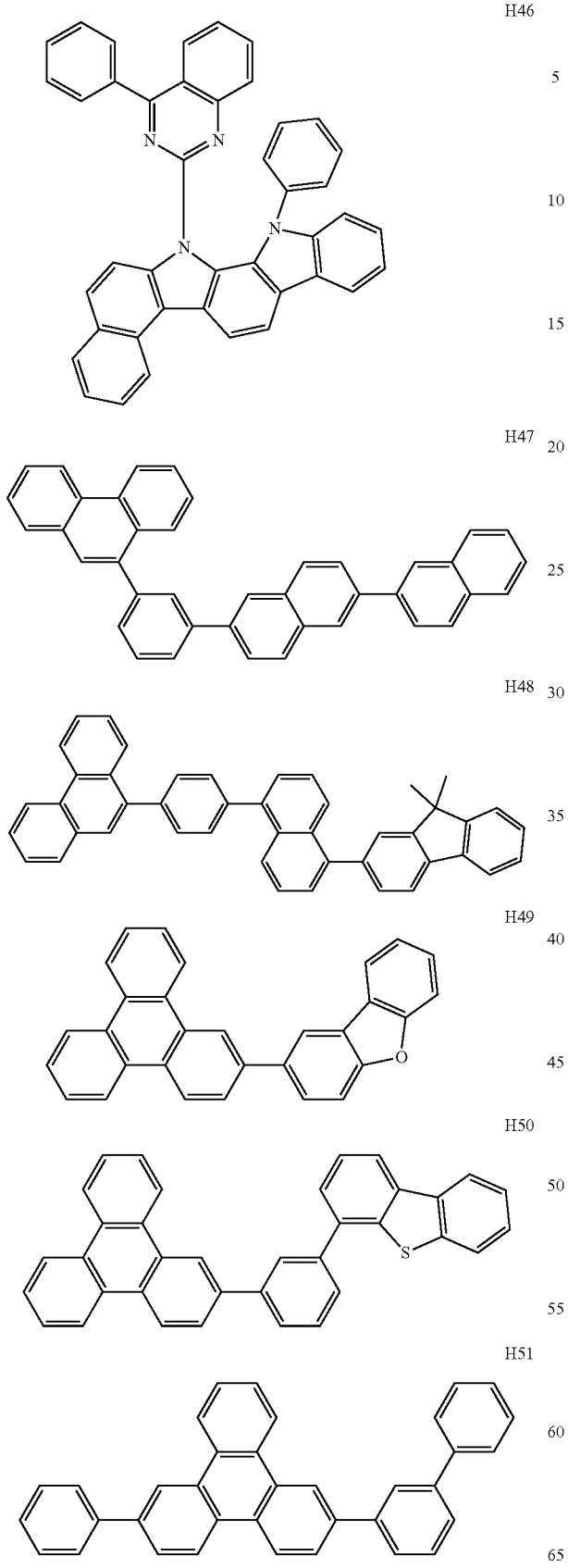

H56
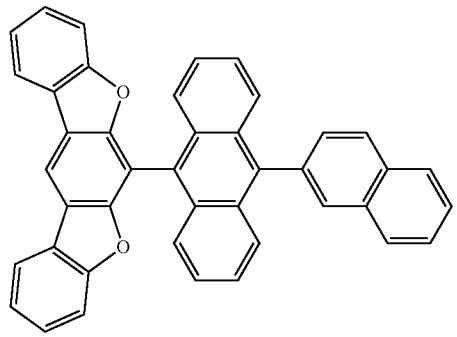
H57
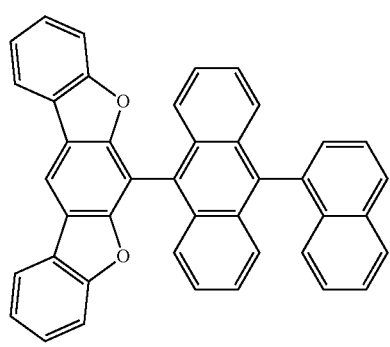
H58
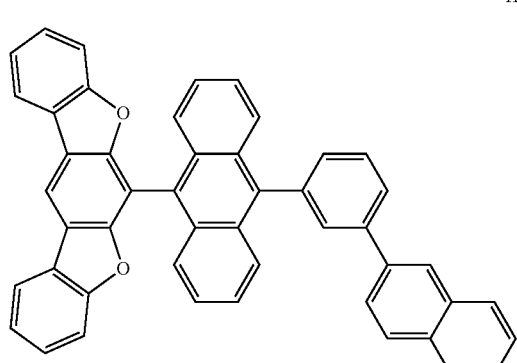
H59
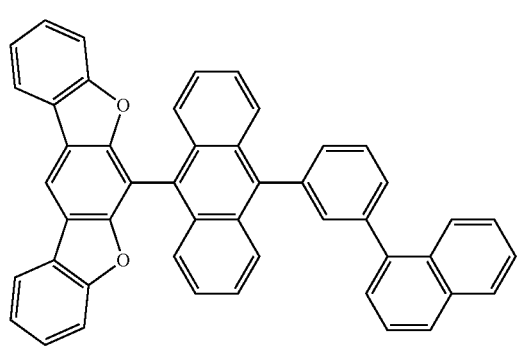
H60
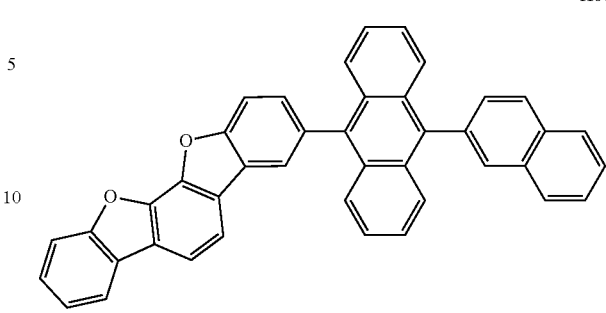
H61
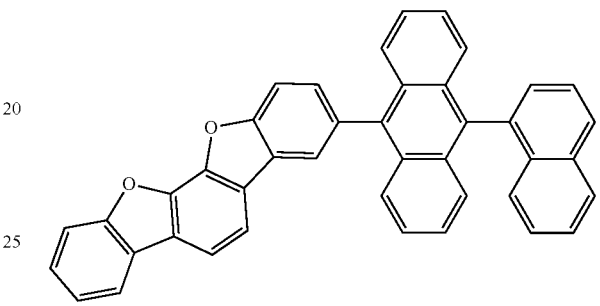
H62
H63
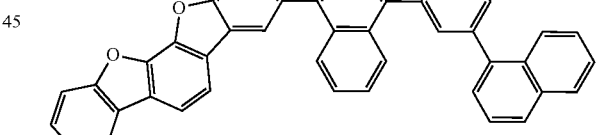
H64
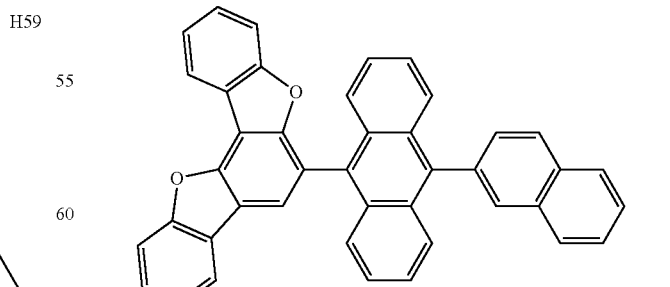

-continued
H65
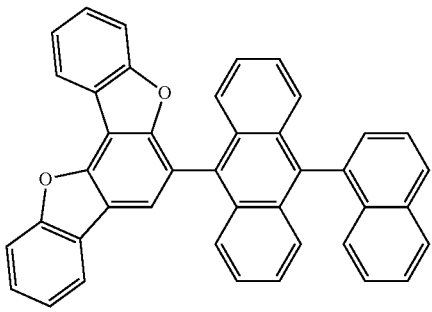
H66
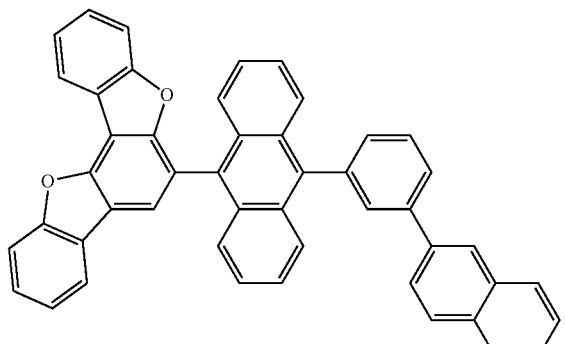
H67
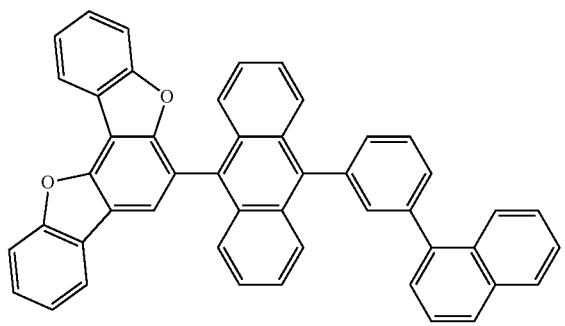
H68
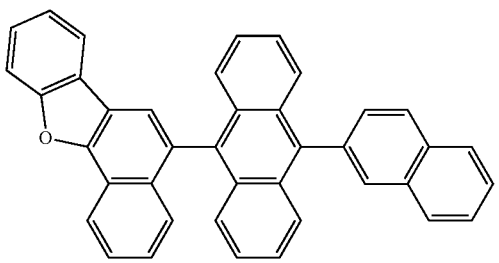
H69
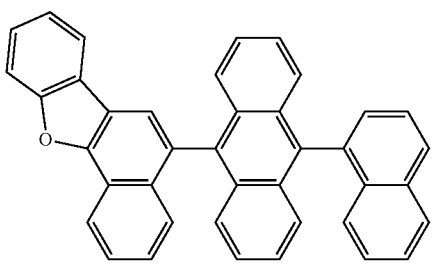
-continued
H70
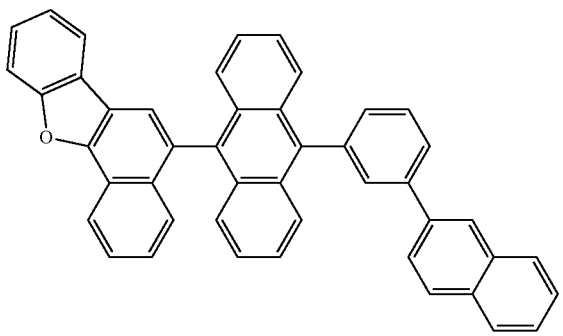
H71
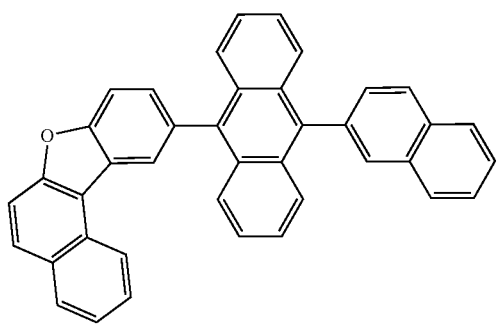
H72
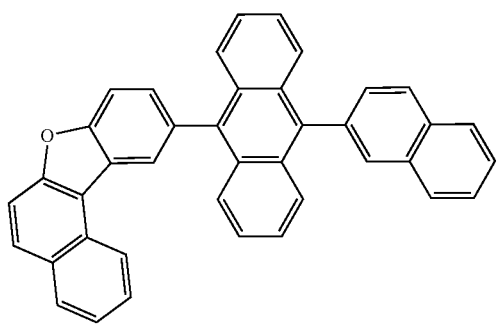
H73
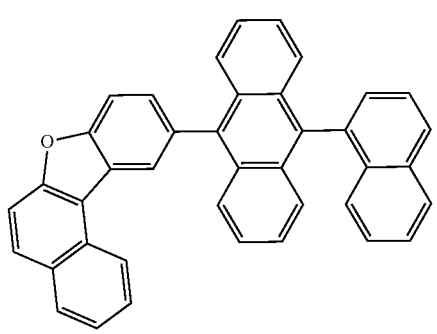

H74
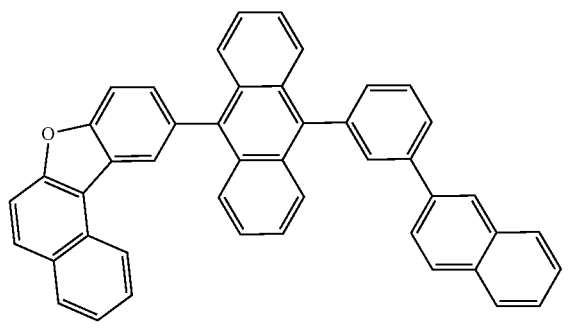
H75
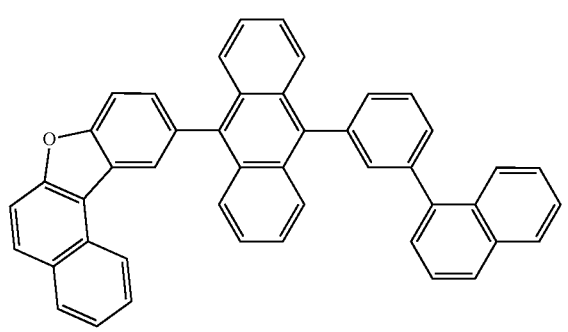
H76
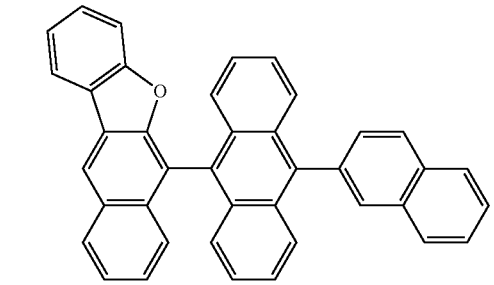
H77
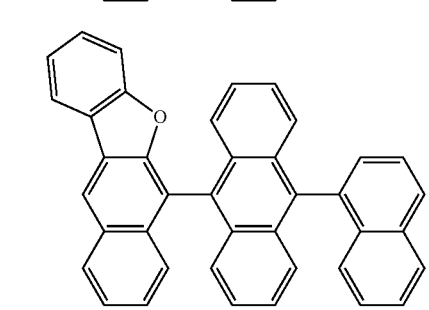
H78
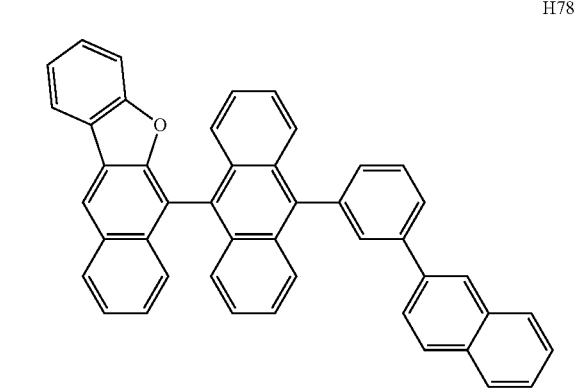
H79
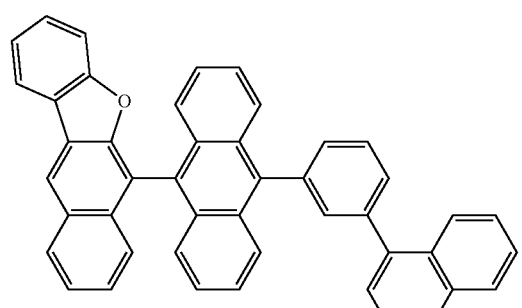
H80
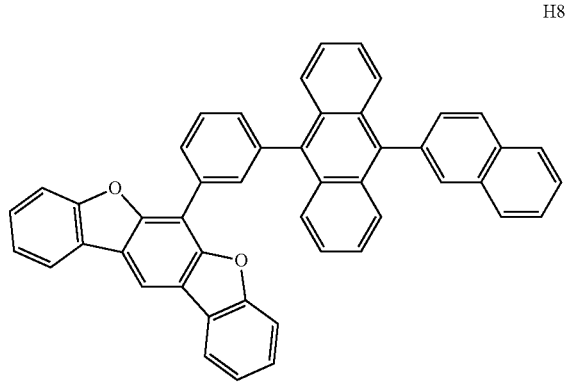
H81
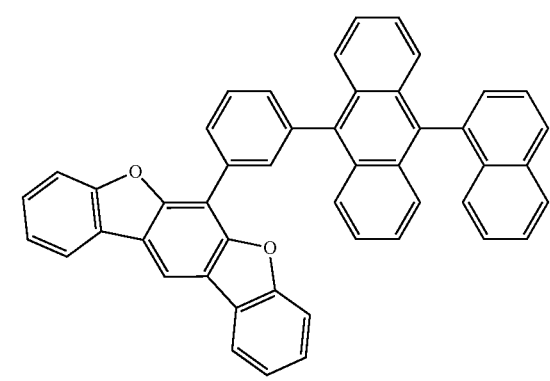
H82
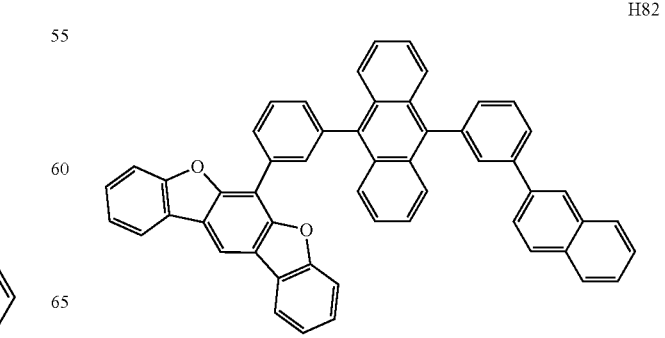

H83
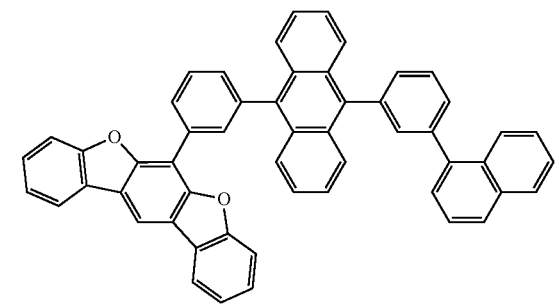
H84
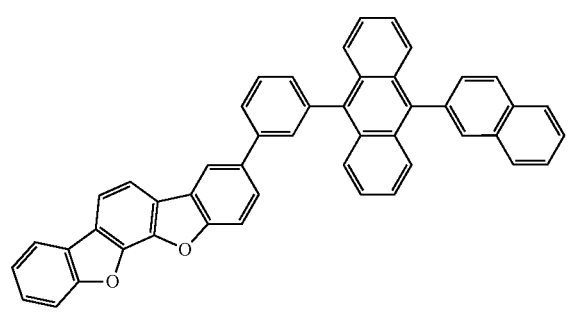
H85
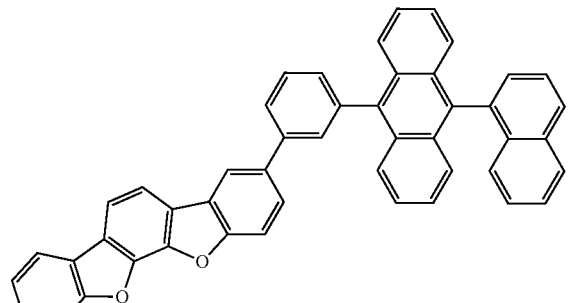
H86
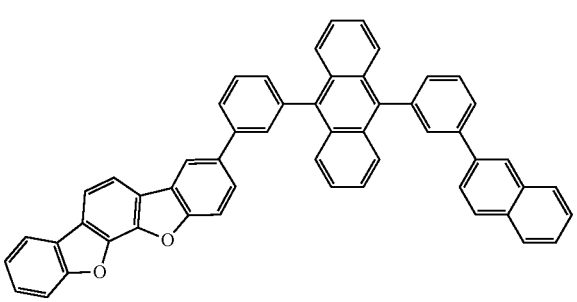
H87
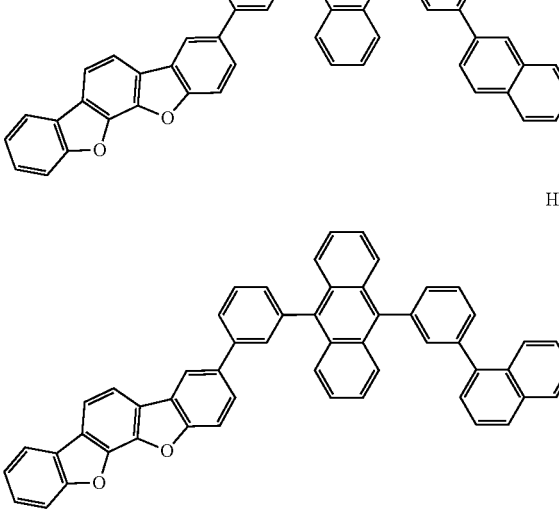
H88
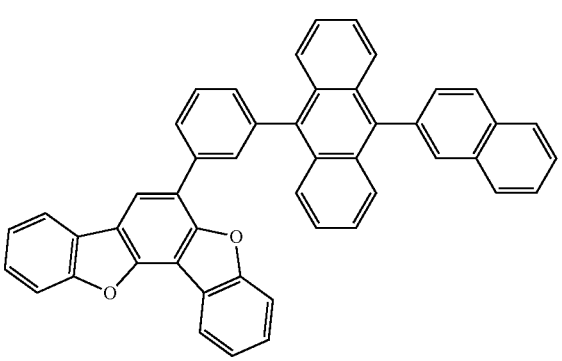
H89
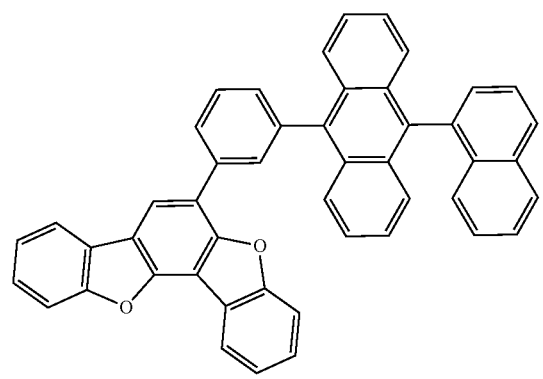
H90
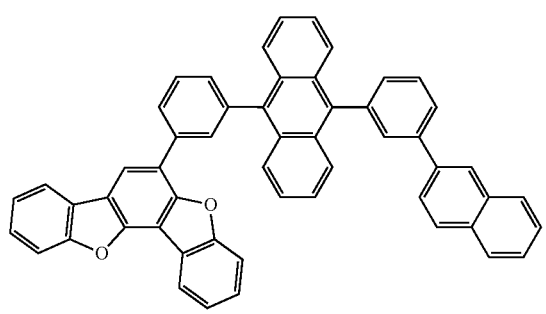
H91
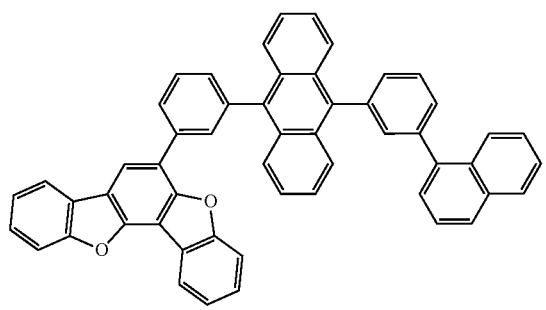

-continued
H92
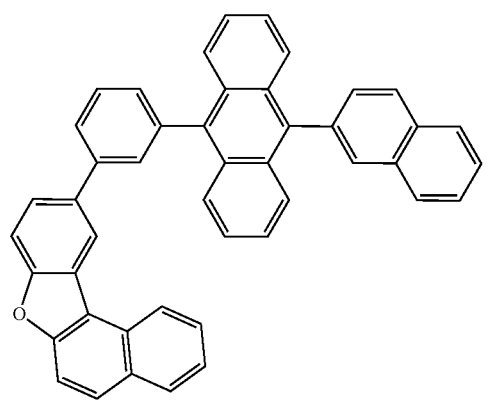
H93
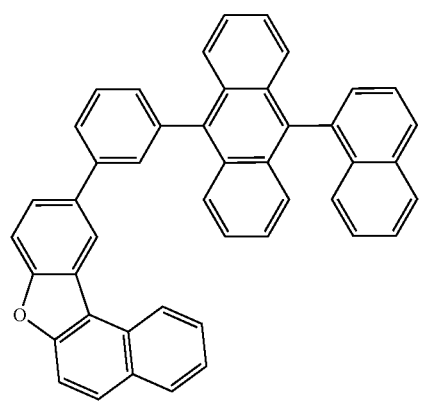
H94
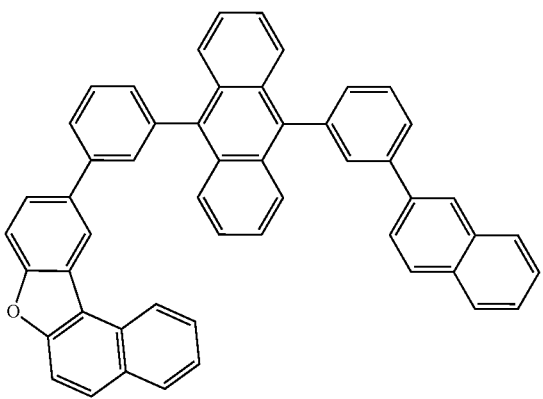
H95
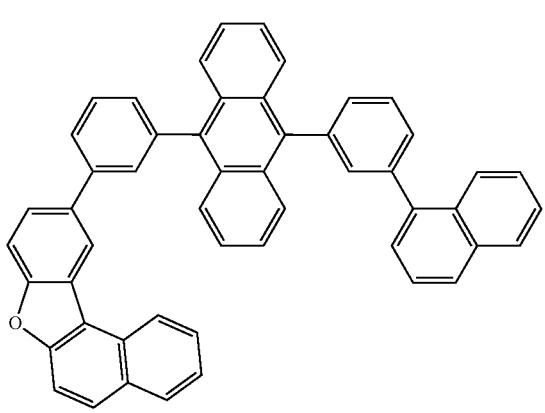
-continued
H96
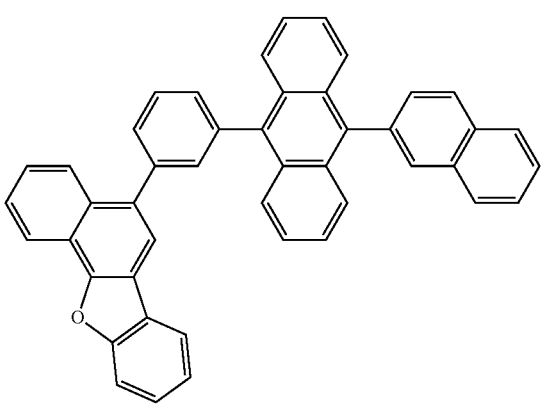
H97
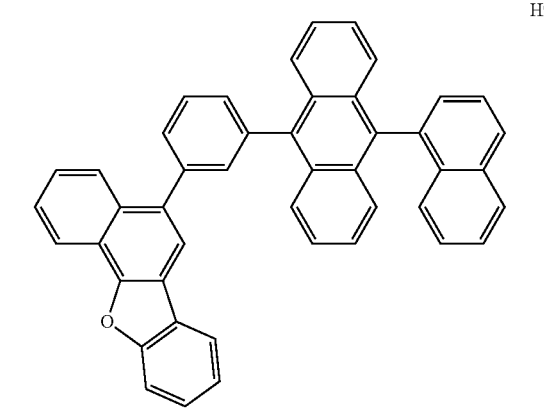
H98
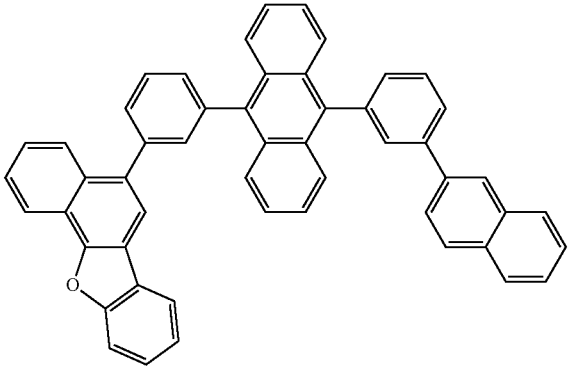
H99
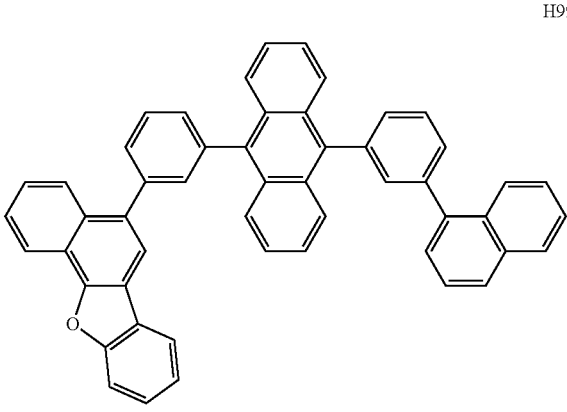

H100
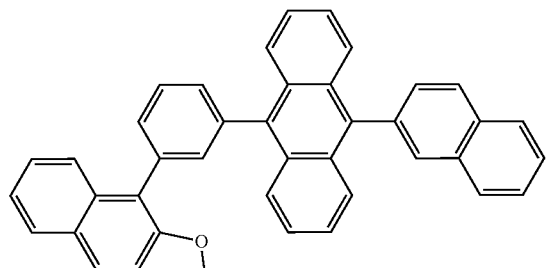
H101
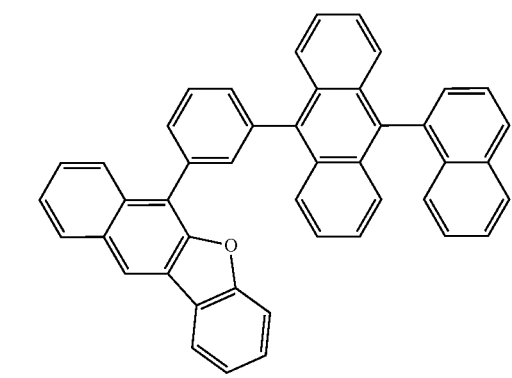
H102
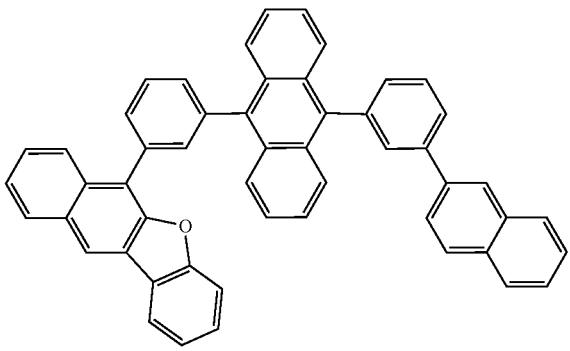
H103
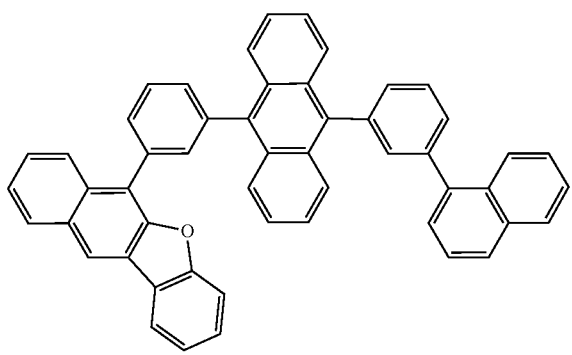
H104
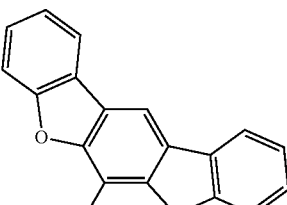
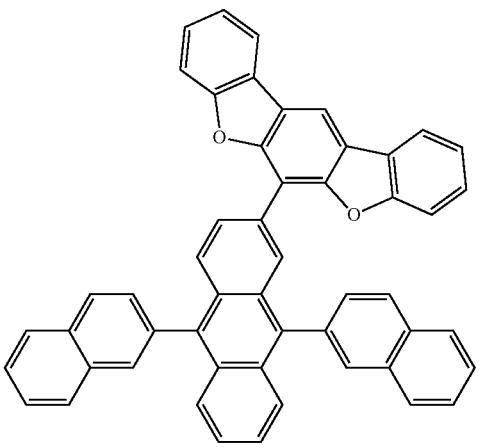
H105
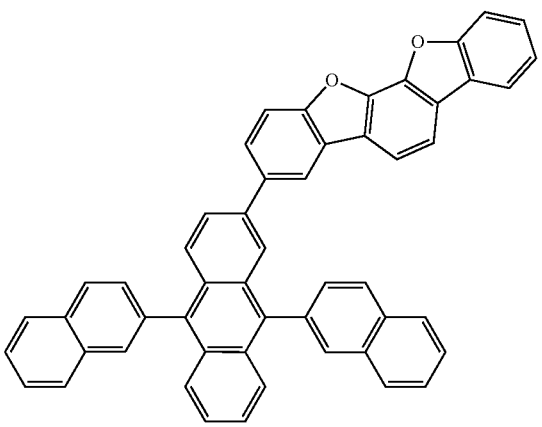
H106
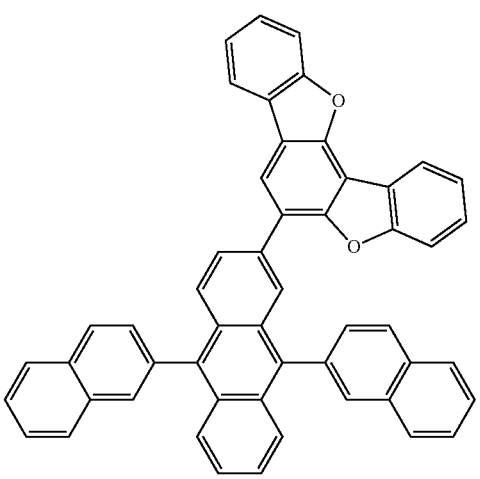

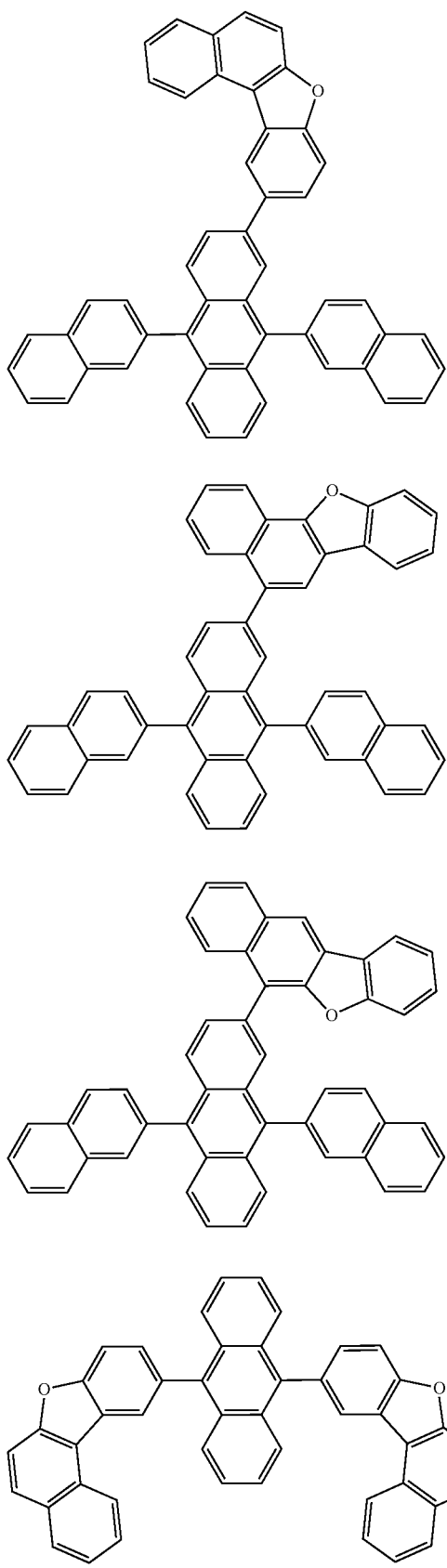
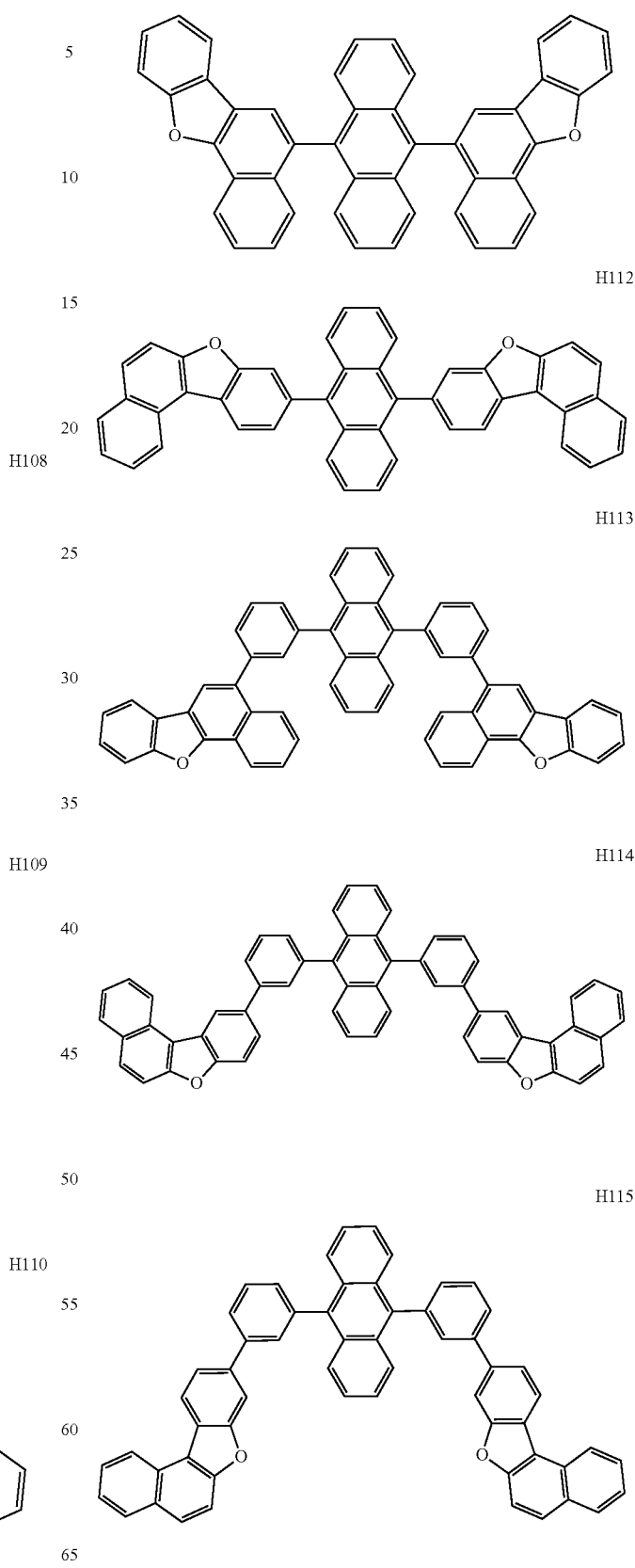

-continued
H116
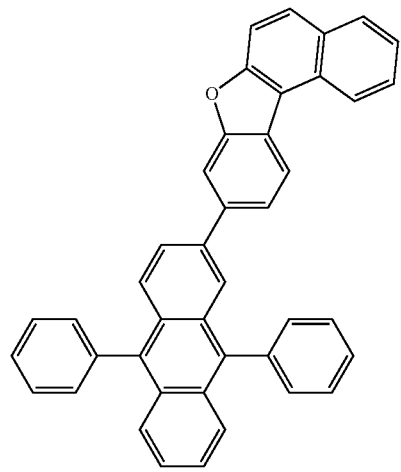
H117
H118
-continued
H119
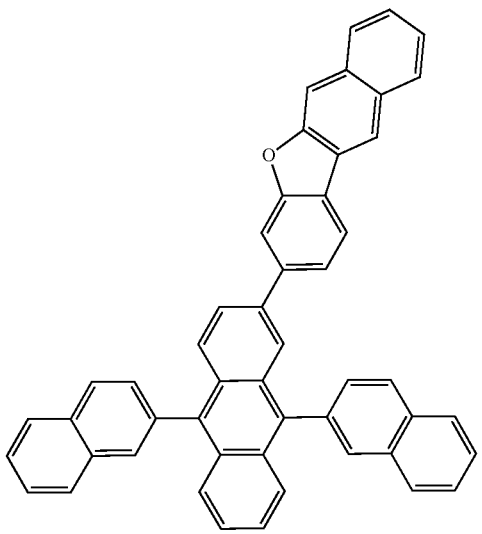
H120
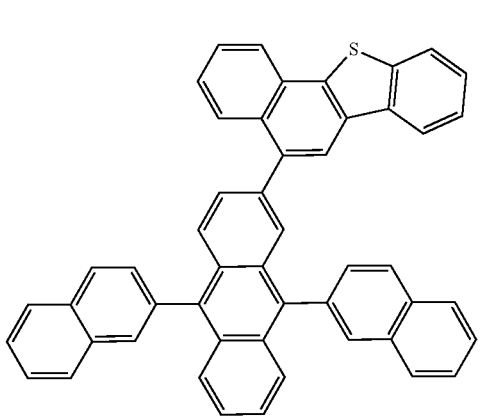
H121
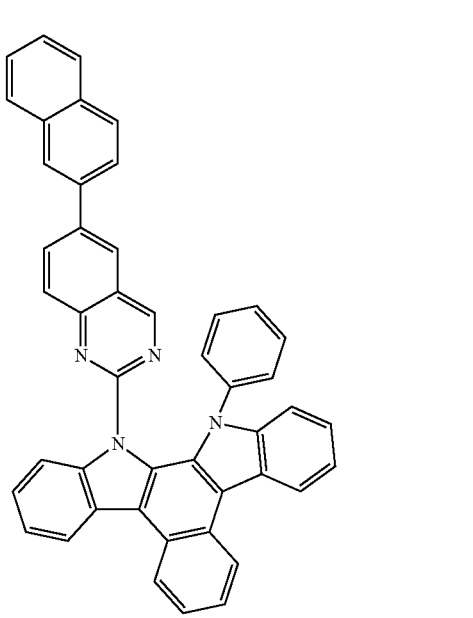

H122 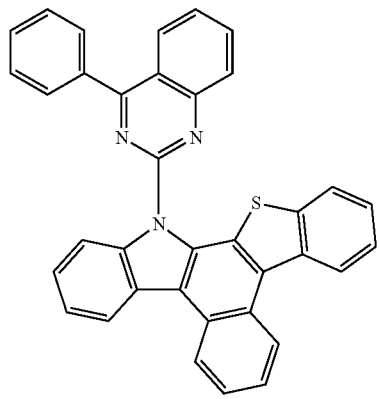

H123 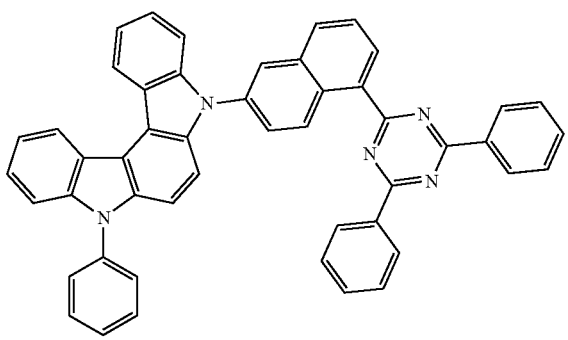

H124 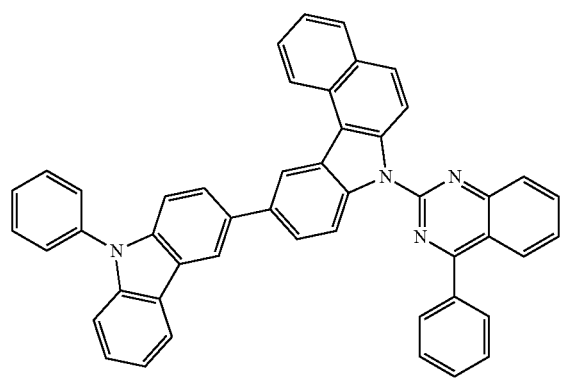

H125 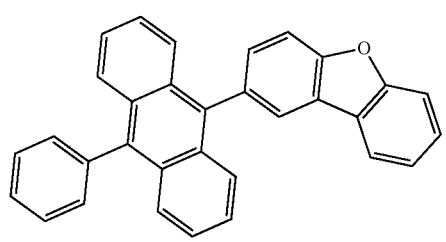

H126 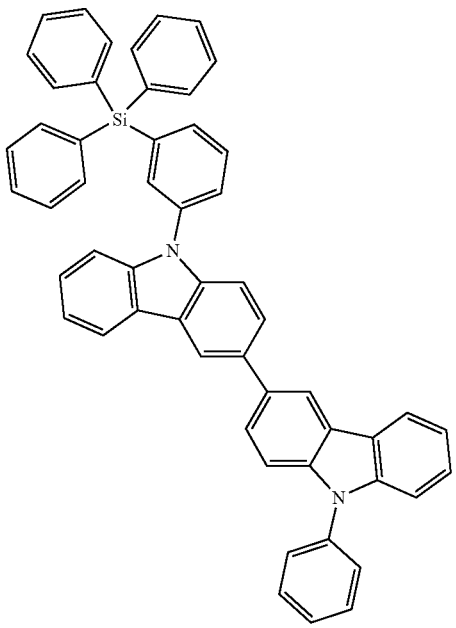

[Phosphorescent Dopant]

In embodiments, the phosphorescent dopant may include at least one transition metal as a central metal.

The phosphorescent dopant may include a monodentate ligand, a bidentate ligand, a tridentate ligand, a tetradentate ligand, a pentadentate ligand, a hexadentate ligand, or any combination thereof.

The phosphorescent dopant may be electrically neutral.

For example, the phosphorescent dopant may include an organometallic compound represented by Formula 401:

[Formula 401]

$M(L_{401})_{xc1}(L_{402})_{xc2}$

[Formula 402]

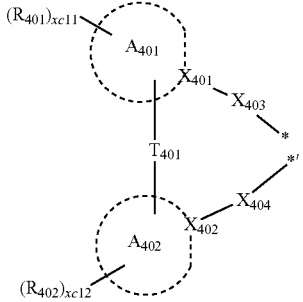

In Formulae 401 and 402,

M may be a transition metal (for example, iridium (Ir), platinum (Pt), palladium (Pd), osmium (Os), titanium (Ti), gold (Au), hafnium (Hf), europium (Eu), terbium (Tb), rhodium (Rh), rhenium (Re), or thulium (Tm)), $L_{401}$ may be a ligand represented by Formula 402, and xc1 may be 1, 2, or 3, wherein when xc1 is two or more, two or more of $L_{401}$(s) may be identical to or different from each other, $L_{402}$ may be an organic ligand, and xc2 may be 0, 1, 2, 3, or 4, and when xc2 is 2 or more, two or more of $L_{402}$(s) may be identical to or different from each other, $X_{401}$ and $X_{402}$ may each independently be nitrogen (N) or carbon (C), ring $A_{401}$ and ring $A_{402}$ may each independently be a $C_3$-$C_{60}$ carbocyclic group or a $C_1$-$C_{60}$ heterocyclic group, $T_{401}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C=*', $X_{403}$ and $X_{404}$ may each independently be a chemical bond (for example, a covalent bond or a coordination bond), O, S, N($Q_{413}$), B($Q_{413}$), P($Q_{413}$), C($Q_{413}$)($Q_{414}$), or Si($Q_{413}$)($Q_{414}$), $Q_{411}$ to $Q_{414}$ may each independently be the same as described in connection with Qi, $R_{401}$ and $R_{402}$ may each independently be hydrogen, deuterium, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), or —P(=O)($Q_{401}$)($Q_{402}$), $Q_{401}$ to $Q_{403}$ may each independently be the same as described in connection with Qi, xc11 and xc12 may each independently be an integer from 0 to 10,

* and *' in Formula 402 each indicate a binding site to M in Formula 401.

For example, in Formula 402, $X_{401}$ may be nitrogen, and $X_{402}$ may be carbon, or each of $X_{401}$ and $X_{402}$ may be nitrogen.

In embodiments, when xc1 in Formula 401 is 2 or more, two ring $A_{401}$ in two or more of $L_{401}$(s) may be optionally linked to each other via $T_{402}$, which is a linking group, and two ring $A_{402}$ are optionally linked to each other via $T_{403}$, which is a linking group (see Compounds PD1 to PD4 and PD7). $T_{402}$ and $T_{403}$ may each independently be the same as described in connection with $T_{401}$.

$L_{402}$ in Formula 401 may be an organic ligand. For example, $L_{402}$ may include a halogen group, a diketone group (for example, an acetylacetonate group), a carboxylic acid group (for example, a picolinate group), —C(=O), an isonitrile group, —CN group, a phosphorus-containing group (for example, a phosphine group, a phosphite group, etc.), or any combination thereof.

The phosphorescent dopant may include, for example, one of compounds PD1 to PD25, or any combination thereof:

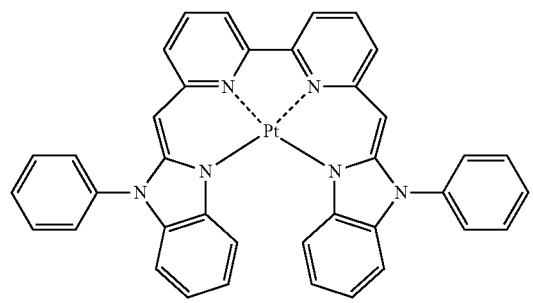

PD1

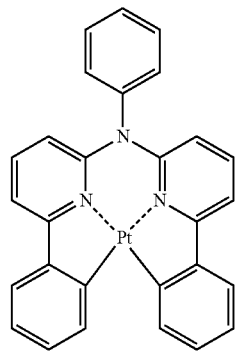

PD2

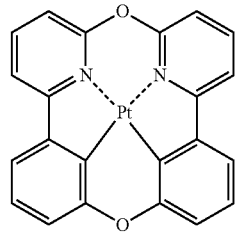

PD3

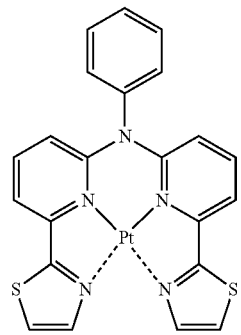

PD4

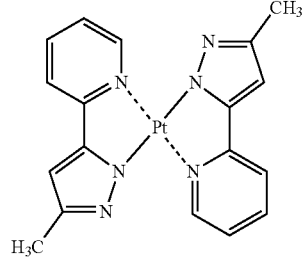

PD5

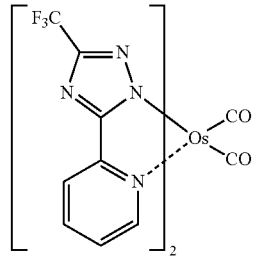

PD6

PD7
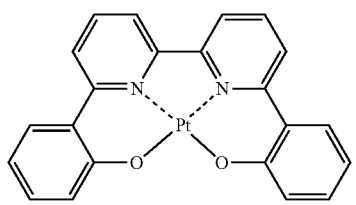
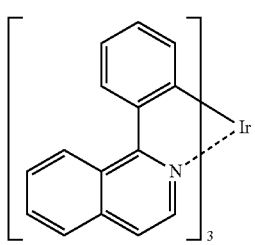
PD8
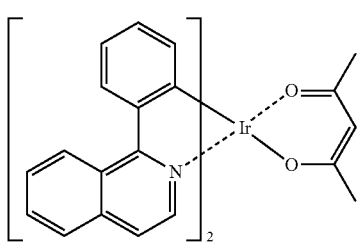
PD9
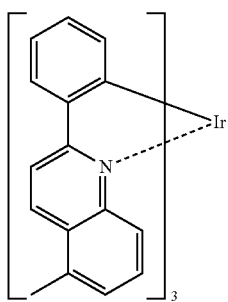
PD10
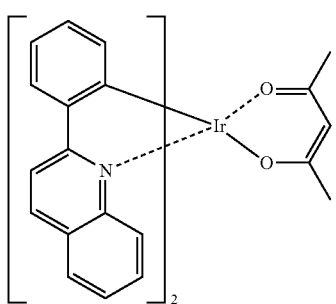
PD11
PD12
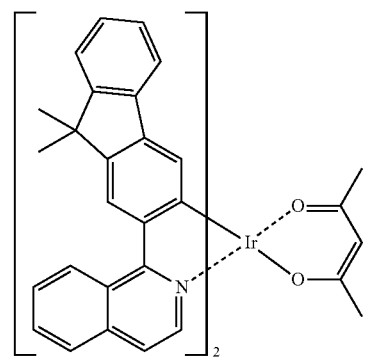
PD13
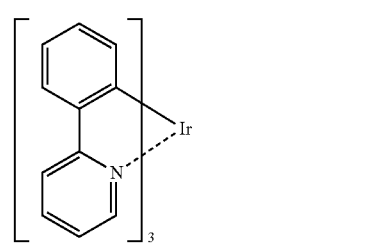
PD14
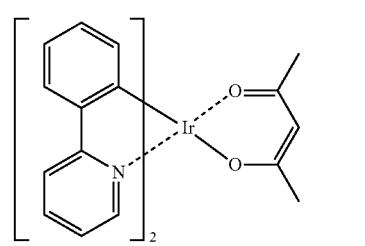
PD15
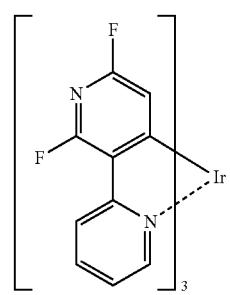
PD16
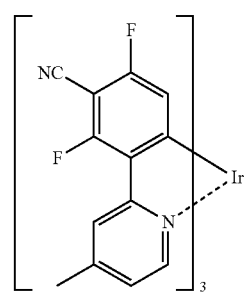

PD17
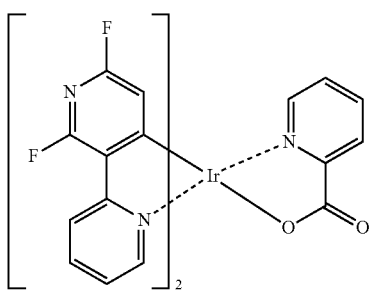
PD18
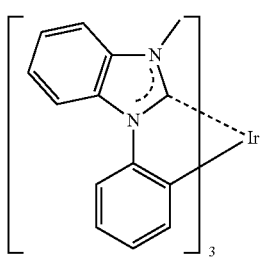
PD19
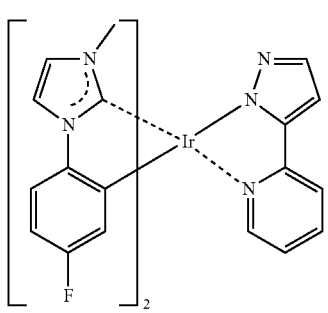
PD20
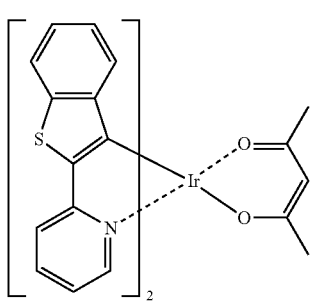
PD21
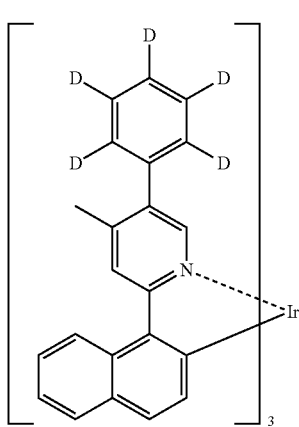
PD22
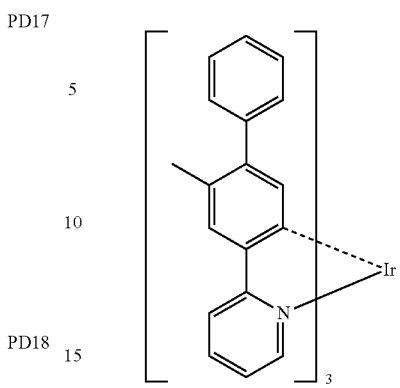
PD23
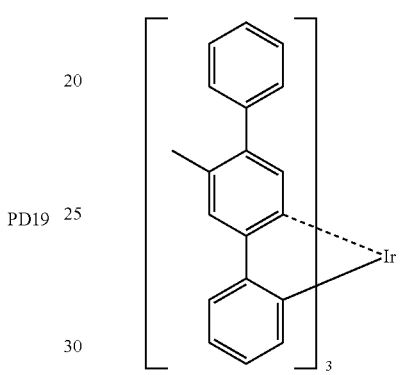
PD24
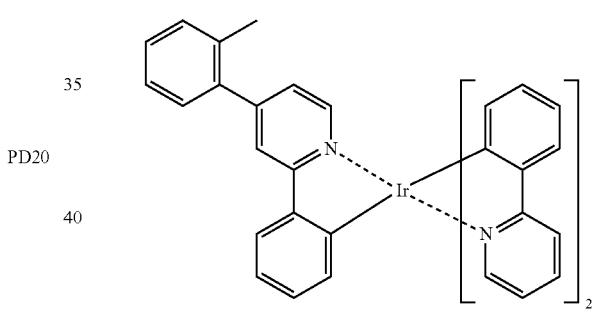
PD25
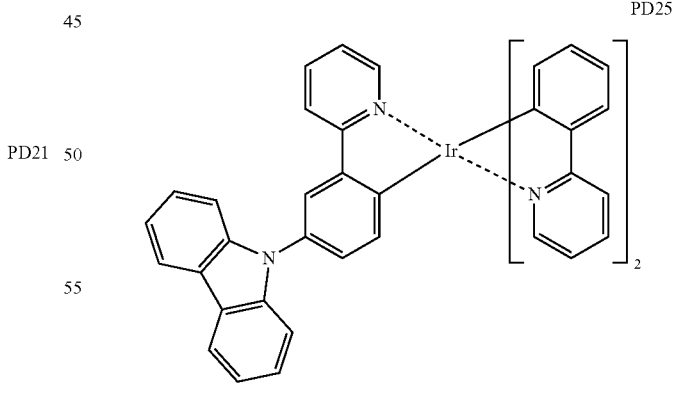
[Fluorescent Dopant]
The fluorescent dopant may include an amine group-containing compound, a styryl group-containing compound, or any combination thereof.
In embodiments, the fluorescent dopant may include a compound represented by Formula 501:

[Formula 501]

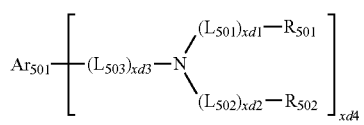

In Formula 501, $Ar_{501}$, $L_{501}$ to $L_{503}$, $R_{501}$, and $R_{502}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xd1 to xd3 may each independently be 0, 1, 2, or 3, xd4 may be 1, 2, 3, 4, 5, or 6.

In embodiments, $Ar_{501}$ in Formula 501 may be a condensed cyclic group (for example, an anthracene group, a chrysene group, or a pyrene group) in which three or more monocyclic groups are condensed together.

In embodiments, xd4 in Formula 501 may be 2.

In embodiments, the fluorescent dopant may include one of Compounds FD1 to FD36, DPVBi, DPAVBi, or any combination thereof:

FD1

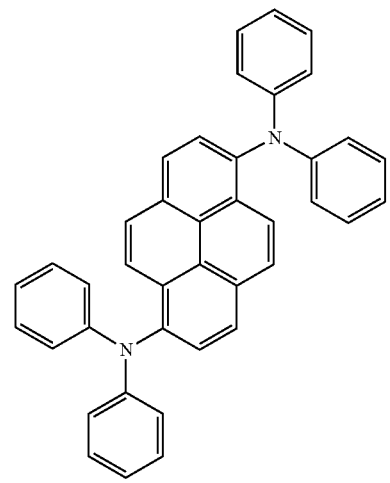

FD2

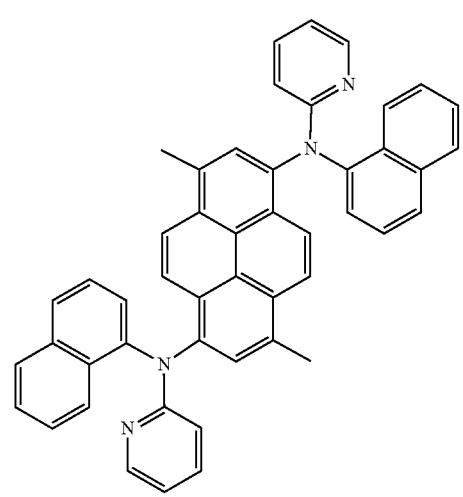

FD3

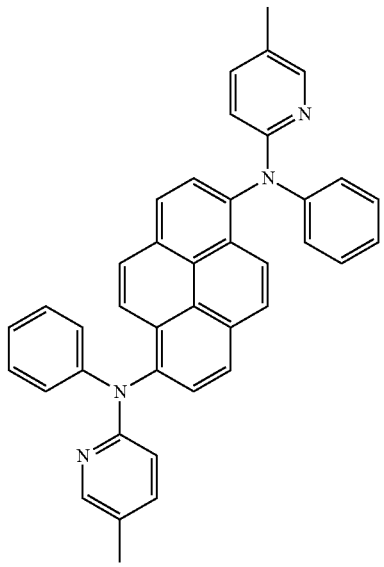

FD4

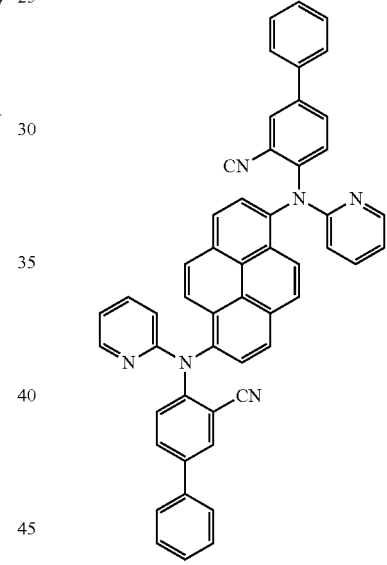

FD5

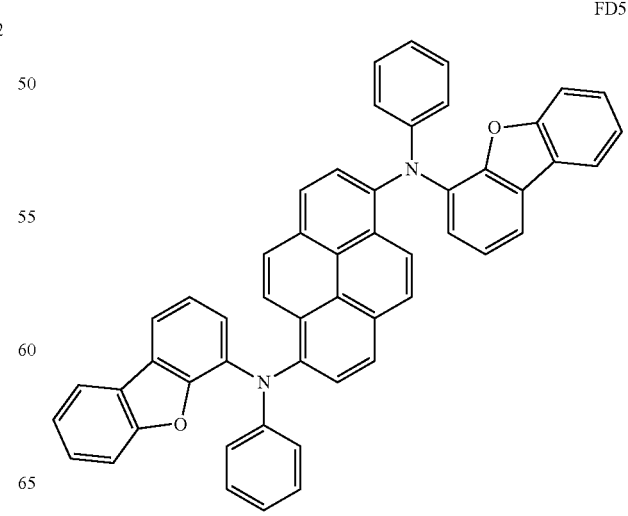

FD6
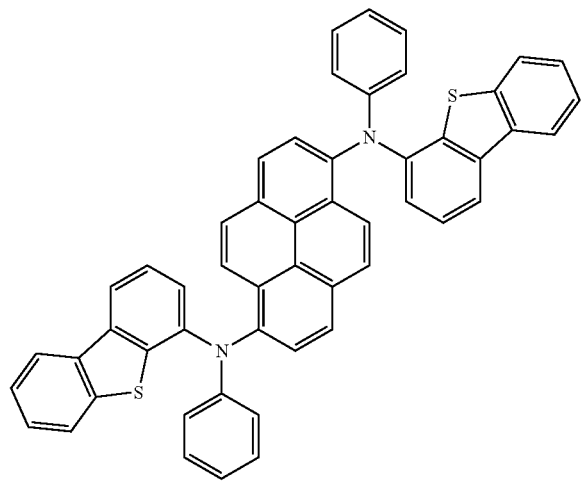
FD7
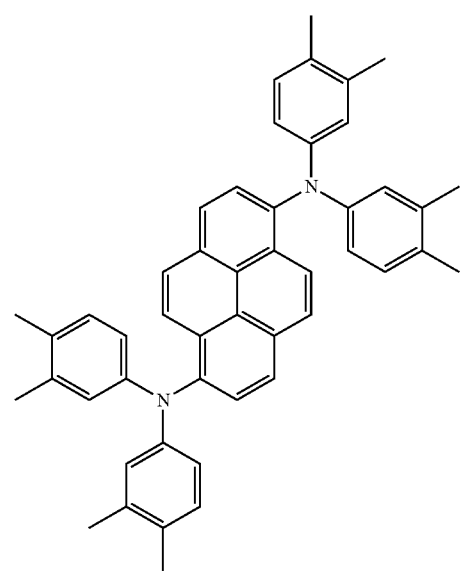
FD8
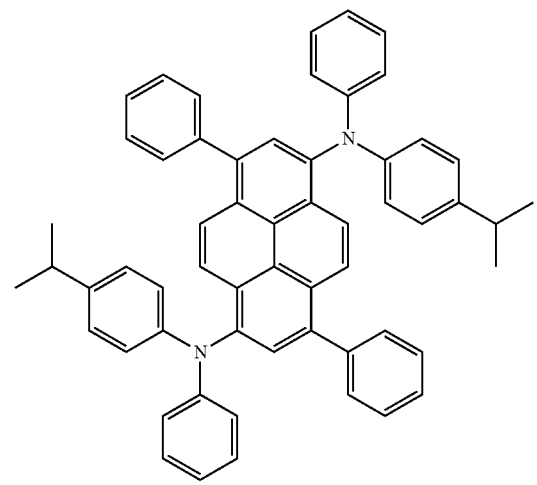
FD9
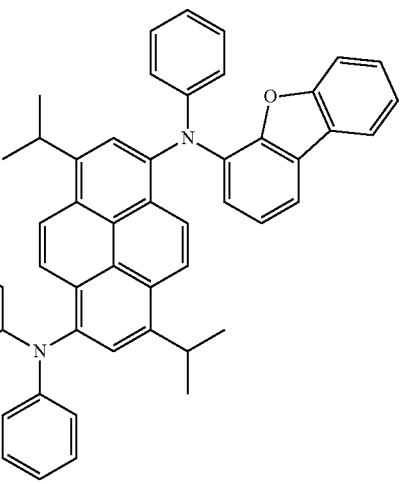
FD10
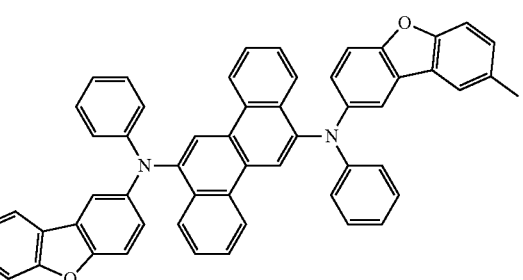
FD11
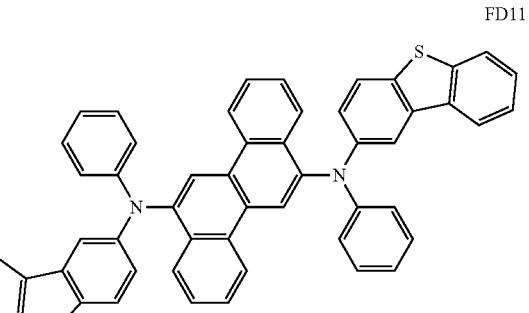
FD12
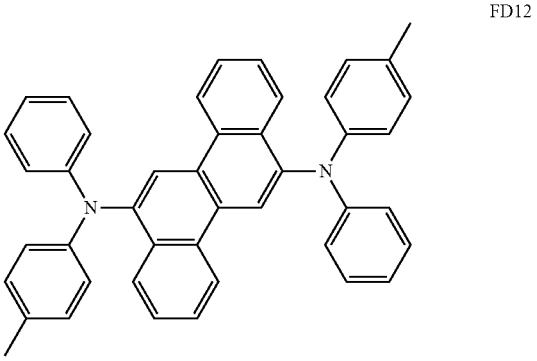

-continued
FD13
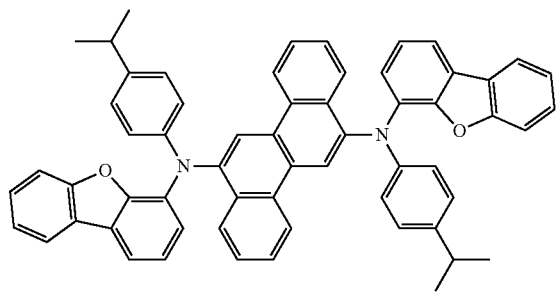
FD14
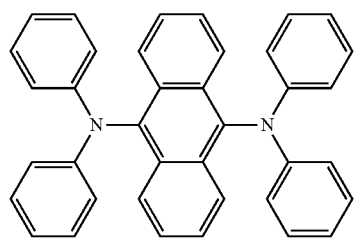
FD15
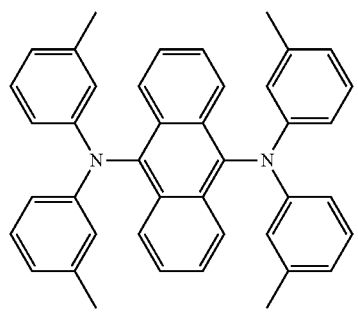
FD16
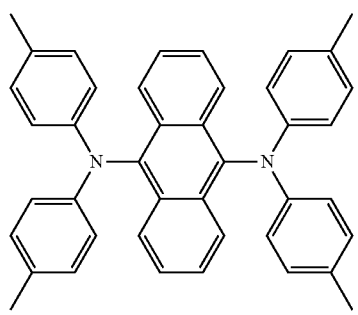
FD17
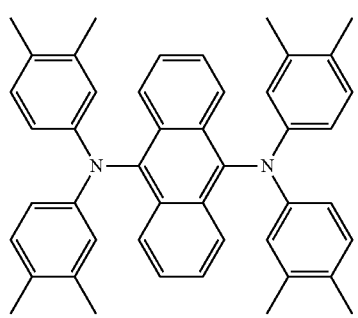
-continued
FD18
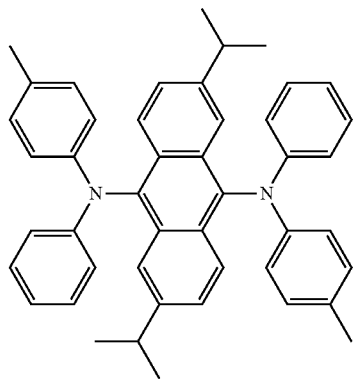
FD19
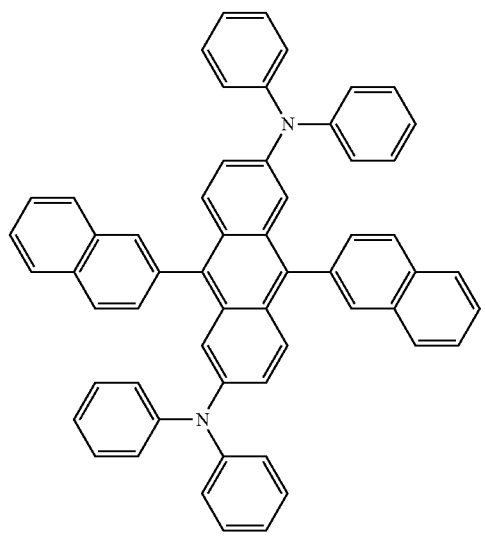
FD20
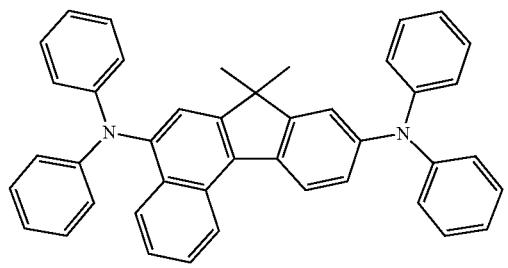
FD21
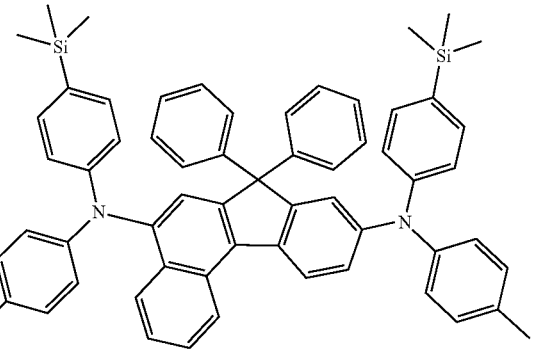

FD22
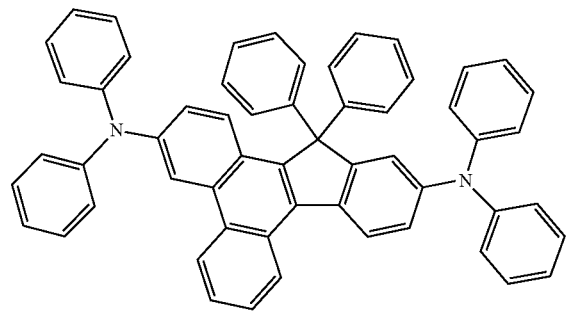
FD23
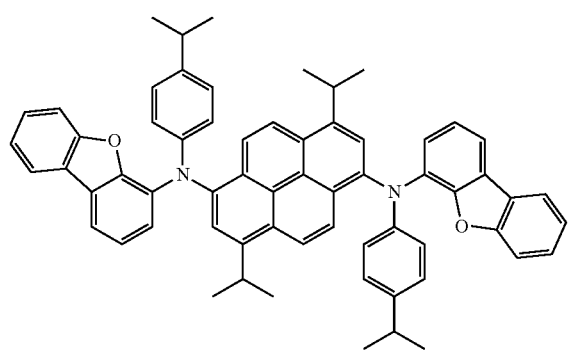
FD24
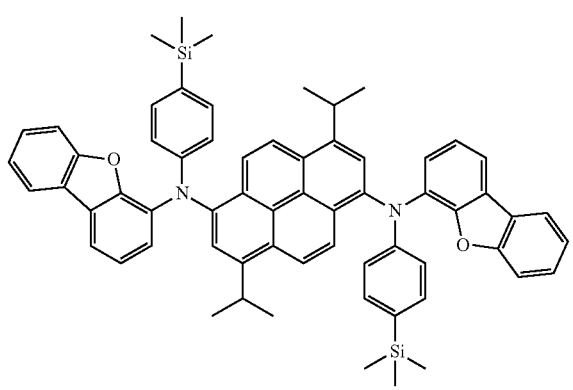
FD25
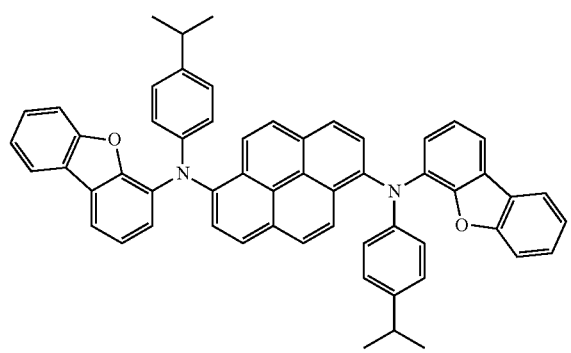
FD26
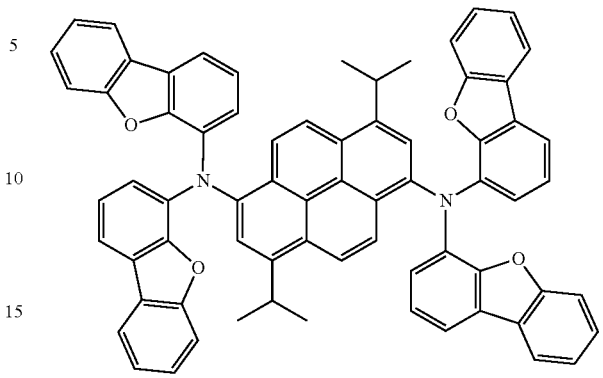
FD27
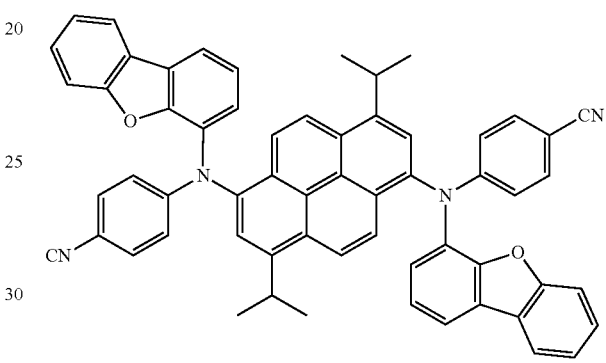
FD28
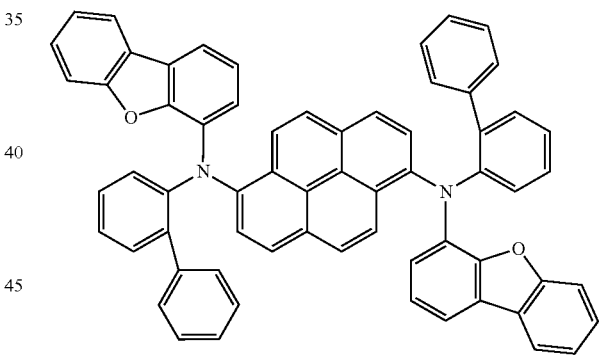
FD29
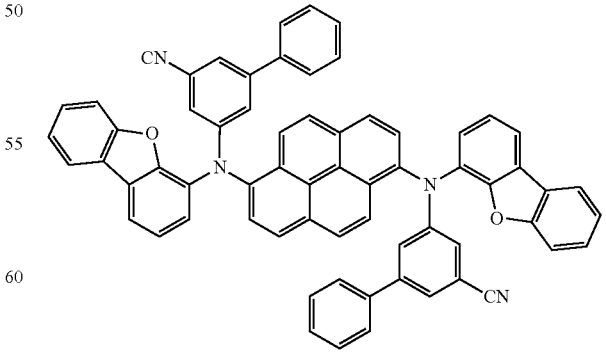

FD30
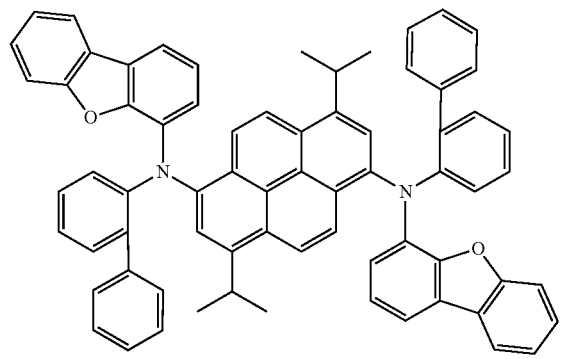
FD31
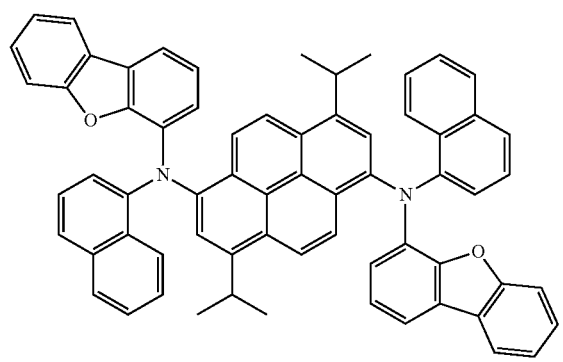
FD32
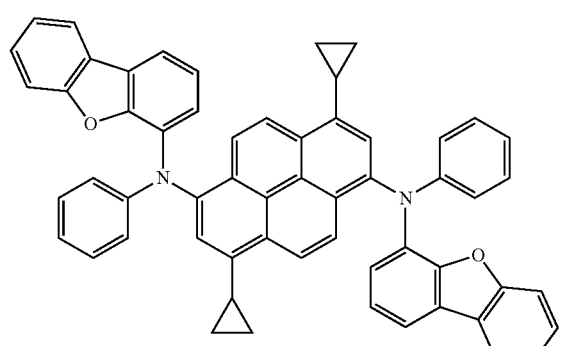
FD33
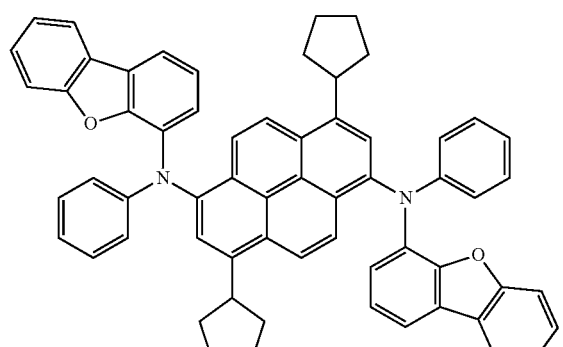
FD34
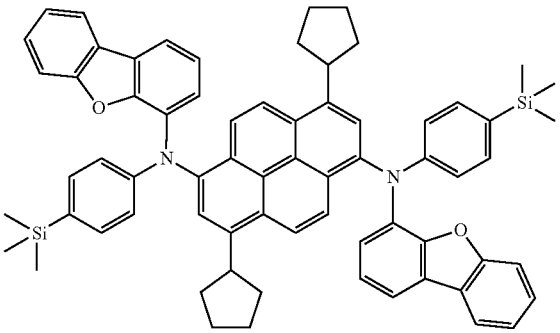
FD35
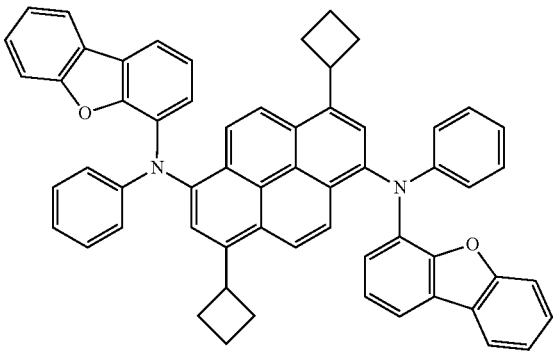
FD36
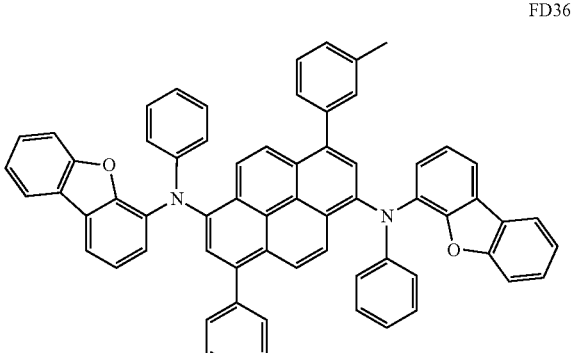
DPVBi
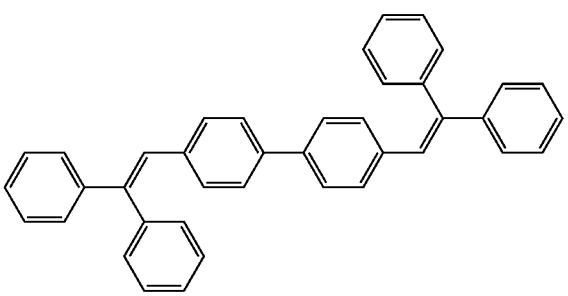

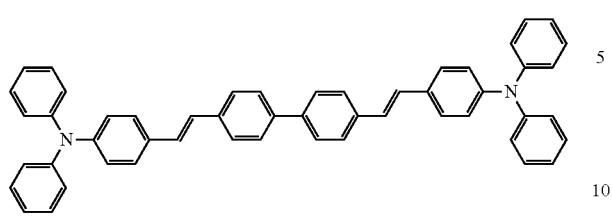
DPAVBi

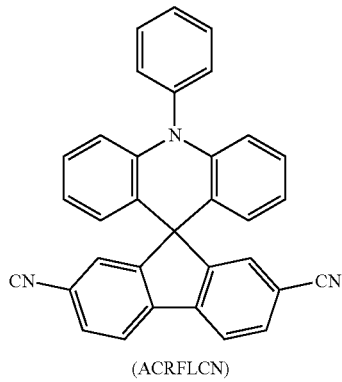
(ACRFLCN)

DF2

[Delayed Fluorescence Material]

The emission layer may include a delayed fluorescence material.

In the specification, the delayed fluorescence material may be selected from compounds capable of emitting delayed fluorescence based on a delayed fluorescence emission mechanism.

The delayed fluorescent material included in the emission layer may act as a host or a dopant depending on the type of other materials included in the emission layer.

In embodiments, a difference between the triplet energy level (eV) of the delayed fluorescence material and the singlet energy level (eV) of the delayed fluorescence material may be in a range of about 0 eV to about 0.5 eV. When the difference between the triplet energy level (eV) of the delayed fluorescent material and the singlet energy level (eV) of the delayed fluorescent material satisfies the above-described range, up-conversion from the triplet state to the singlet state of the delayed fluorescent materials may effectively occur, and thus, the emission efficiency of the light-emitting device 10 may be improved.

In embodiments, the delayed fluorescence material may include a material including at least one electron donor (for example, a π electron-rich $C_3$-$C_{60}$ cyclic group, such as a carbazole group) and at least one electron acceptor (for example, a sulfoxide group, a cyano group, or a π electron-deficient nitrogen-containing $C_1$-$C_{60}$ cyclic group), and a material including a $C_8$-$C_{60}$ polycyclic group in which two or more cyclic groups are condensed while sharing boron (B).

In embodiments, the delayed fluorescence material may include at least one of the following compounds DF1 to DF9:

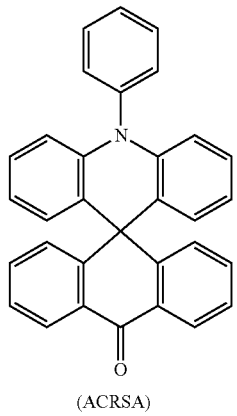
(ACRSA)

DF3

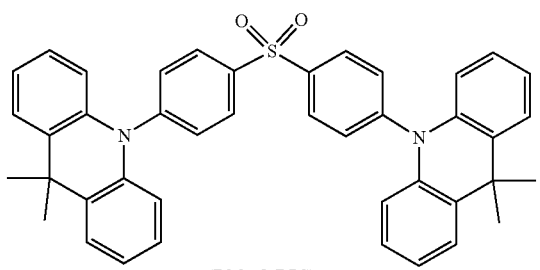
(DMAC-DPS)

DF1

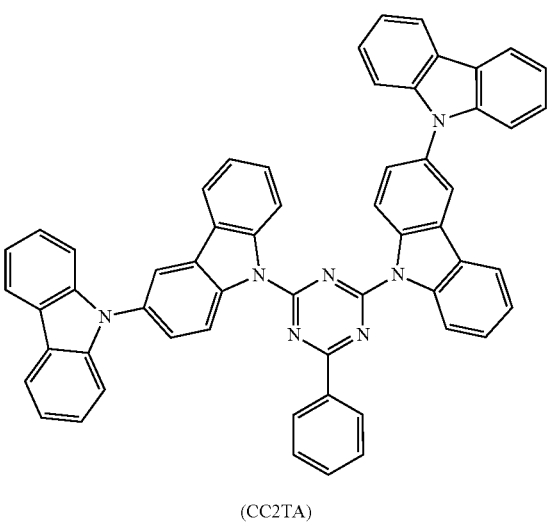
(CC2TA)

DF4

-continued

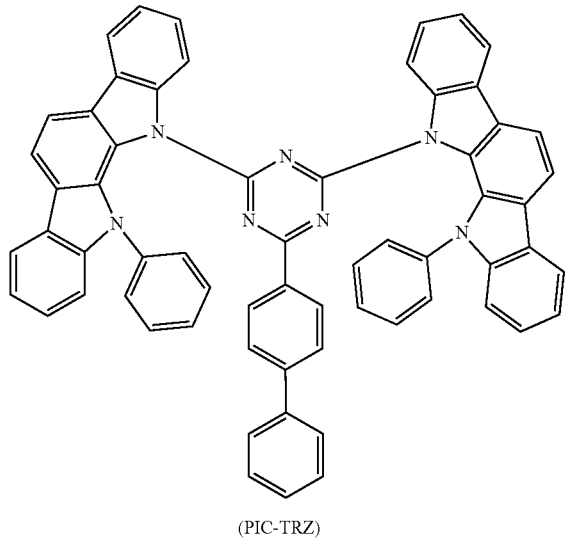

(PIC-TRZ)

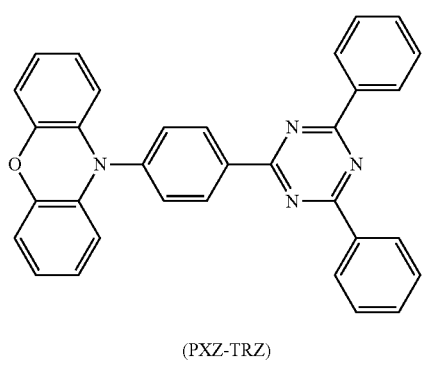

(PIC-TRZ2)

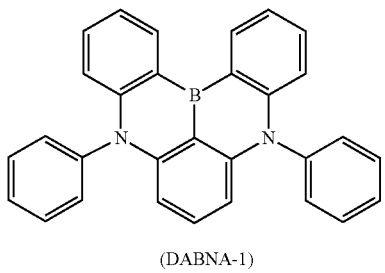

(PXZ-TRZ)

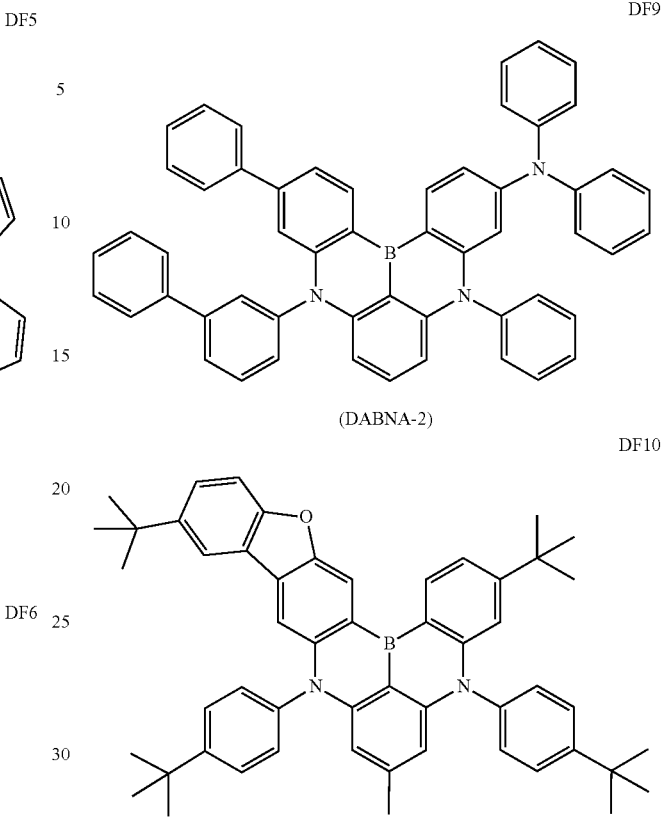

(DABNA-1)

(DABNA-2)

(DF10 structure)

[Quantum Dot]

The emission layer may include a quantum dot.

In the specification, a quantum dot may be a crystal of a semiconductor compound, and may include any material capable of emitting light of various emission wavelengths according to the size of the crystal.

A diameter of the quantum dot may be, for example, in a range of about 1 nm to about 10 nm.

The quantum dot may be synthesized by a wet chemical process, a metal organic chemical vapor deposition process, a molecular beam epitaxy process, or any process similar thereto.

According to the wet chemical process, a precursor material is mixed with an organic solvent to grow a quantum dot particle crystal. When the crystal grows, the organic solvent naturally acts as a dispersant coordinated on the surface of the quantum dot crystal and controls the growth of the crystal so that the growth of quantum dot particles can be controlled through a process which is more easily performed than vapor deposition methods, such as metal organic chemical vapor deposition (MOCVD) or molecular beam epitaxy (MBE), and which requires low costs.

The quantum dot may include Group II-VI semiconductor compounds, Group III-V semiconductor compounds, Group III-VI semiconductor compounds, Group I-III-VI semiconductor compounds, Group IV-VI semiconductor compounds, a Group IV element or compound; or any combination thereof.

Examples of the Group II-VI semiconductor compound may include a binary compound, such as CdSe, CdTe, ZnS, ZnSe, ZnTe, ZnO, HgS, HgSe, HgTe, MgSe, or MgS; a ternary compound, such as CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, or MgZnS; a quaternary compound, such as CdZnSeS, CdZnSeTe, CdZnSTe, CdHgSeS, CdHgSeTe, CdHgSTe, HgZnSeS, HgZnSeTe, or HgZnSTe; or any combination thereof.

Examples of the Group III-V semiconductor compound may include a binary compound, such as GaN, GaP, GaAs, GaSb, AlN, AlP, AlAs, AlSb, InN, InP, InAs, InSb, or the like; a ternary compound, such as GaNP, GaNAs, GaNSb, GaPAs, GaPSb, AlNP, AlNAs, AlNSb, AlPAs, AlPSb, InGaP, InNP, InAlP, InNAs, InNSb, InPAs, InPSb, GaAlNP, or the like; a quaternary compound, such as GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, or the like; or any combination thereof. The Groups III-V semiconductor compound may further include Group II elements. Examples of the Groups III-V semiconductor compound further including Group II elements may include InZnP, InGaZnP, InAlZnP, etc.

Examples of the Group III-VI semiconductor compound may include a binary compound, such as GaS, GaSe, $Ga_2Se_3$, GaTe, InS, InSe, $In_2S_3$, $In_2Se_3$, or InTe; a ternary compound, such as $InGaS_3$, or $InGaSe_3$; and any combination thereof.

Examples of the Group I-III-VI semiconductor compound may include a ternary compound, such as AgInS, $AgInS_2$, CuInS, $CuInS_2$, $CuGaO_2$, $AgGaO_2$, or $AgAlO_2$; or any combination thereof.

Examples of the Group IV-VI semiconductor compound may include a binary compound, such as SnS, SnSe, SnTe, PbS, PbSe, PbTe, or the like; a ternary compound, such as SnSeS, SnSeTe, SnSTe, PbSeS, PbSeTe, PbSTe, SnPbS, SnPbSe, SnPbTe, or the like; a quaternary compound, such as SnPbSSe, SnPbSeTe, SnPbSTe, or the like; or any combination thereof.

The Group IV element or compound may include a single element material, such as Si or Ge; a binary compound, such as SiC or SiGe; or any combination thereof.

Each element included in a multi-element compound such as the binary compound, the ternary compound, and the quaternary compound, may exist in a particle at a uniform concentration or at a non-uniform concentration.

The quantum dot may have a single structure or a core-shell structure. In the case of the quantum dot having a single structure, the concentration of each element included in the corresponding quantum dot may be uniform. In embodiments, the material contained in the core and the material contained in the shell may be different from each other.

The shell of the quantum dot may be a protective layer that prevents chemical degeneration of the core to maintain semiconductor characteristics and/or may be a charging layer that imparts electrophoretic characteristics to the quantum dot. The shell may be a single layer or a multi-layer. The interface between the core and the shell may have a concentration gradient in which the concentration of element presents in the shell decreases toward the center of the core.

Examples of the shell of the quantum dot may include an oxide of a metal, an oxide of a metalloid, or an oxide of a non-metal, a semiconductor compound, and any combination thereof. Examples of the oxide of metal, metalloid, or non-metal may include a binary compound, such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, or NiO; a ternary compound, such as $MgAl_2O_4$, $CoFe_2O_4$, $NiFe_2O_4$, or $CoMn_2O_4$; and any combination thereof. Examples of the semiconductor compound may include, as described herein, Group II-VI semiconductor compounds; Group III-V semiconductor compounds; Group III-VI semiconductor compounds; Group I-III-VI semiconductor compounds; Group IV-VI semiconductor compounds; and any combination thereof. The semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, or any combination thereof.

A full width at half maximum (FWHM) of an emission wavelength spectrum of the quantum dot may be equal to or less than about 45 nm. For example, a FWHM of an emission wavelength spectrum of the quantum dot may be equal to or less than about 40 nm. For example, a FWHM of an emission wavelength spectrum of the quantum dot may be equal to or less than about 30 nm. Within these ranges, color purity or color gamut may be increased. Light emitted through the quantum dot may be emitted in all directions, and a wide viewing angle can be improved.

The quantum dot may be a spherical nanoparticle, a pyramidal nanoparticle, a multi-arm nanoparticle, a cubic nanoparticle, a nanotube, a nanowire, a nanofiber, or a nanoplate.

Since the energy band gap can be adjusted by controlling the size of the quantum dot, light having various wavelength bands can be obtained from the quantum dot emission layer. Therefore, by using quantum dots of different sizes, a light-emitting device that emits light of various wavelengths may be implemented. In embodiments, the size of the quantum dot may be selected to emit red, green and/or blue light. The size of the quantum dot may be configured to emit white light by combining light of various colors.

[Electron Transport Region in Interlayer 130]

The electron transport region may have a structure consisting of a layer consisting of a single material, a structure consisting of a layer consisting of different materials, or a multi-layered structure including layers including different materials.

The electron transport region may include a buffer layer, a hole blocking layer, an electron control layer, an electron transport layer, an electron injection layer, or any combination thereof.

In an embodiment, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein, for each structure, constituting layers may be stacked from an emission layer in its respective stated order.

In an embodiment, the electron transport region (for example, the buffer layer, the hole blocking layer, the electron control layer, or the electron transport layer in the electron transport region) may include a metal-free compound including at least one π electron-deficient nitrogen-containing $C_1$-$C_{60}$ cyclic group.

In an embodiment, the electron transport region may include a compound represented by Formula 601 below:

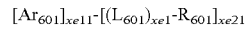 [Formula 601]

In Formula 601, $Ar_{601}$ and $L_{601}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xe11 may be 1, 2, or 3, xe1 may be 0, 1, 2, 3, 4, or 5, $R_{601}$ may be a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, $-Si(Q_{601})(Q_{602})(Q_{603})$, $-C(=O)(Q_{601})$, $-S(=O)_2(Q_{601})$, or $-P(=O)(Q_{601})(Q_{602})$, $Q_{601}$ to $Q_{603}$ may each independently be the same as described in connection with Qi, xe21 may be 1, 2, 3, 4, or 5, at least one of $Ar_{601}$, $L_{601}$, and $R_{601}$ may each independently be a π electron-deficient nitrogen-containing $C_1$-$C_{60}$ cyclic group unsubstituted or substituted with at least one $R_{10a}$.

For example, when xe11 in Formula 601 is 2 or more, two or more of $Ar_{601}$(s) may be linked via a single bond.

In embodiments, $Ar_{601}$ in Formula 601 may be a substituted or unsubstituted anthracene group.

In an embodiment, the electron transport region may include a compound represented by Formula 601-1:

[Formula 601-1]

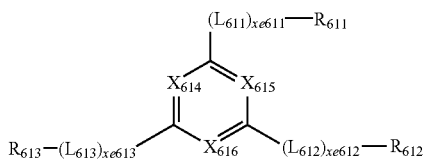

In Formula 601-1, $X_{614}$ may be N or $C(R_{614})$, $X_{615}$ may be N or $C(R_{615})$, $X_{616}$ may be N or $C(R_{616})$, wherein at least one of $X_{614}$ to $X_{616}$ may be N, $L_{611}$ to $L_{613}$ may each independently be the same as described in connection with $L_{601}$, xe611 to xe613 may each independently be the same as described in connection with xe1, $R_{611}$ to $R_{613}$ may each independently be the same as described in connection with $R_{601}$, and $R_{614}$ to $R_{616}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$.

For example, xe1 and xe611 to xe613 in Formulae 601 and 601-1 may each independently be 0, 1, or 2.

The electron transport region may include one of Compounds ET1 to ET47, 2,9-dimethyl-4,7-diphenyl-1,10-phenanthroline (BCP), 4,7-diphenyl-1,10-phenanthroline (Bphen), Alq3, BAlq, TAZ, NTAZ, or any combination thereof.

ET1

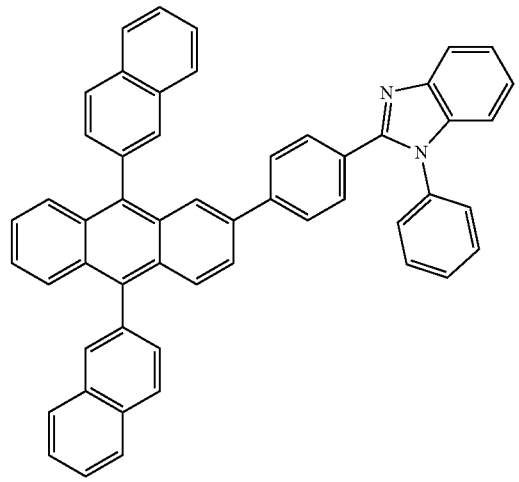

ET2

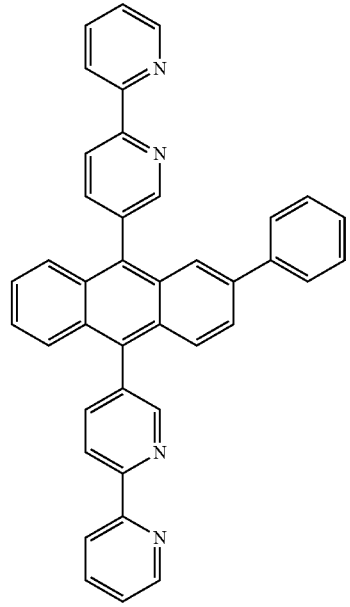

ET3

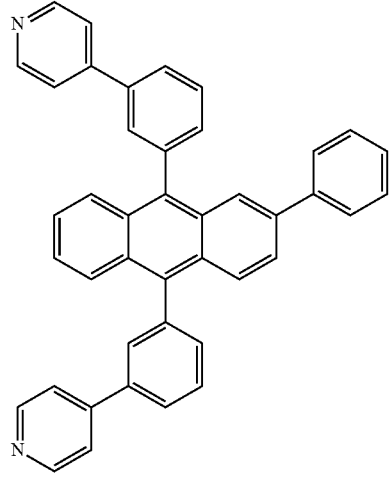

ET4
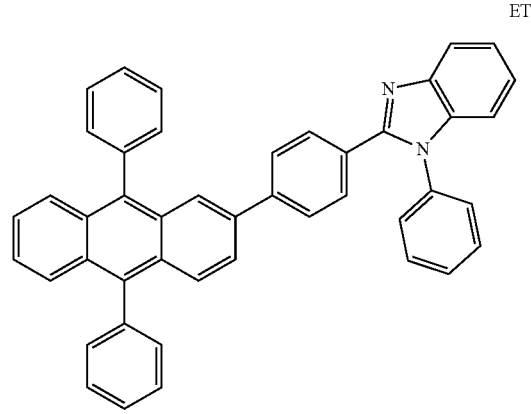
ET7
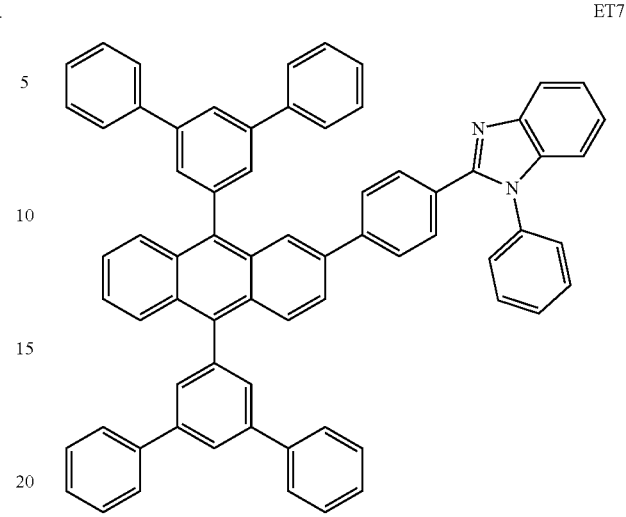
ET5
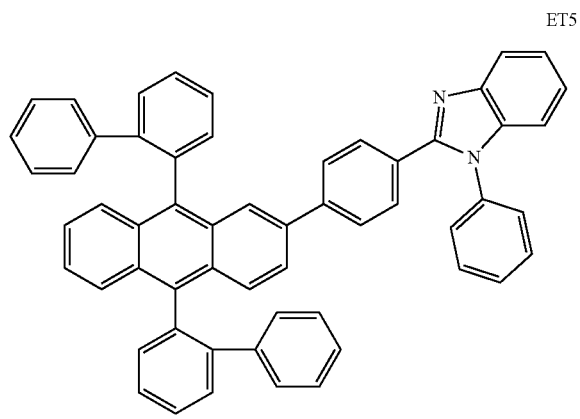
ET8
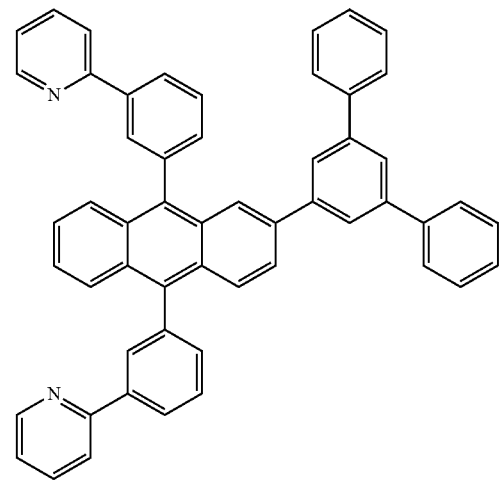
ET6
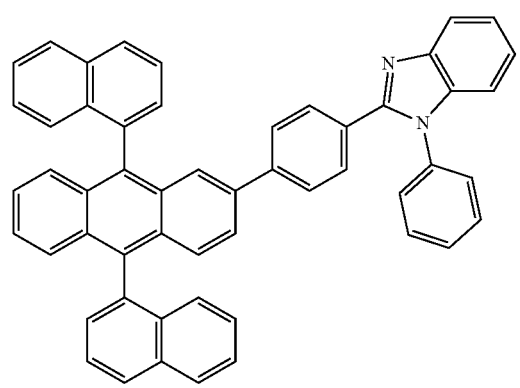
ET9
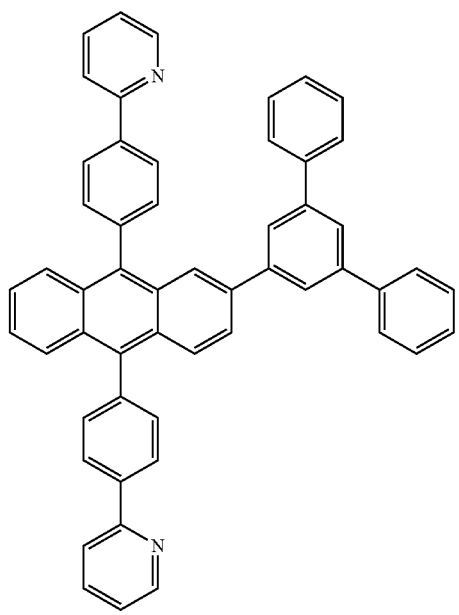

ET10
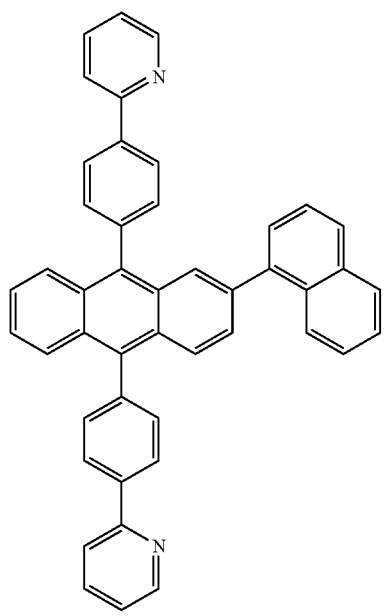
ET11
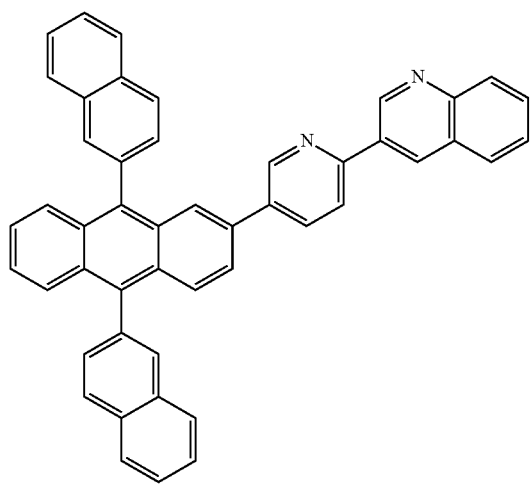
ET12
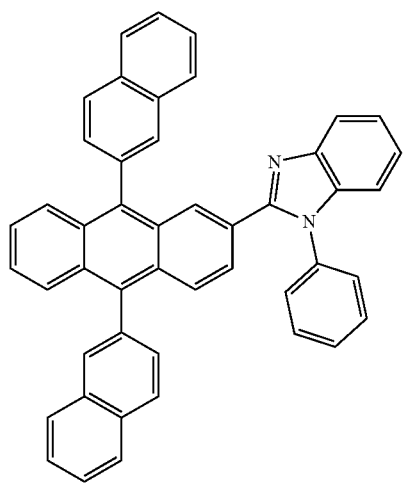
ET13
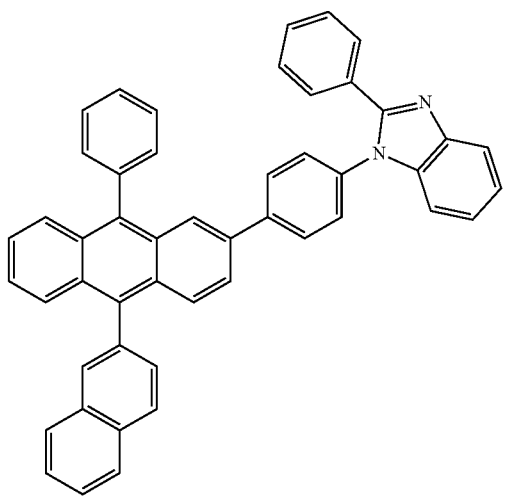
ET14
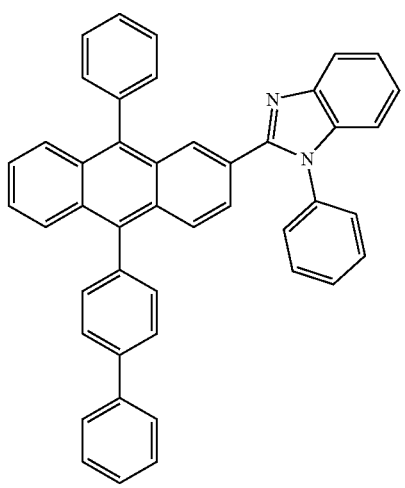
ET15
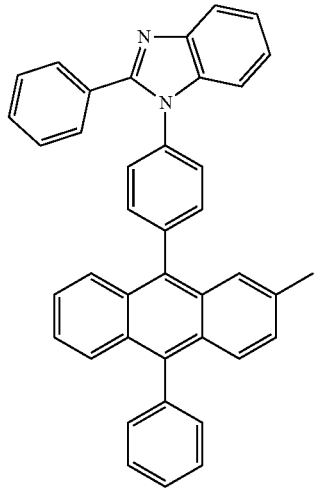

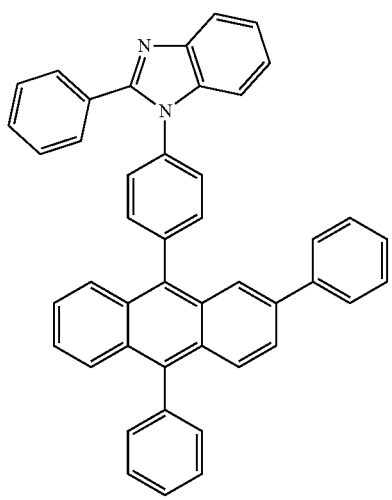
ET16
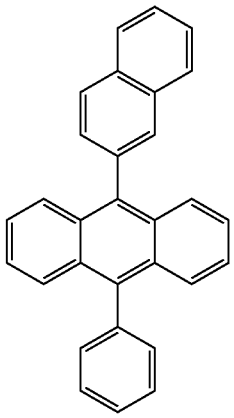
ET19
ET17
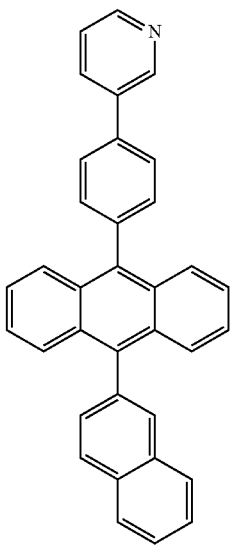
ET20
ET18
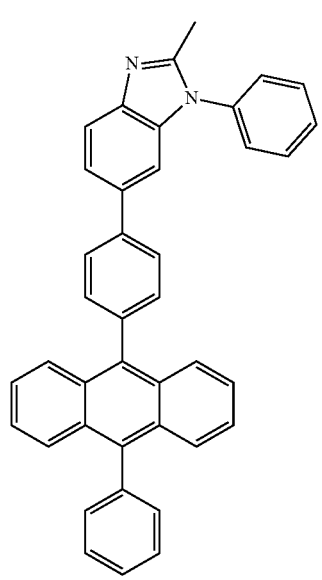
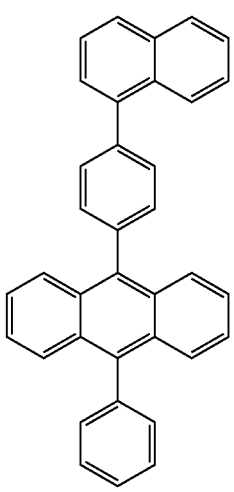
ET21

ET22
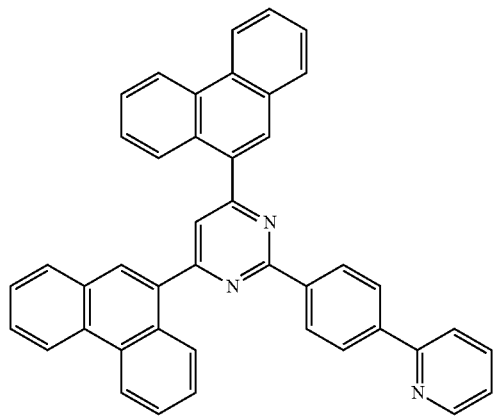
ET25
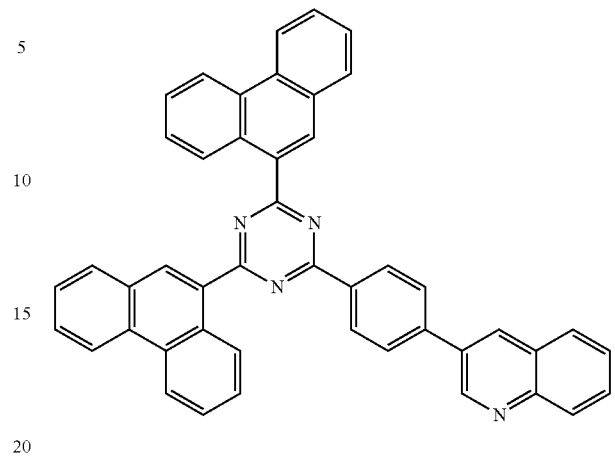
ET23
ET26
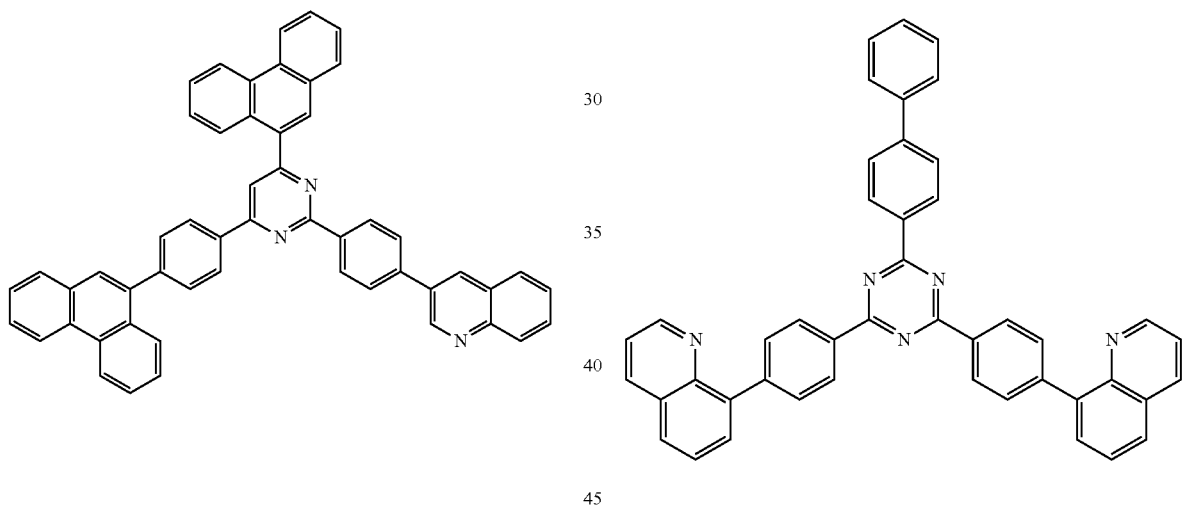
ET24
ET27
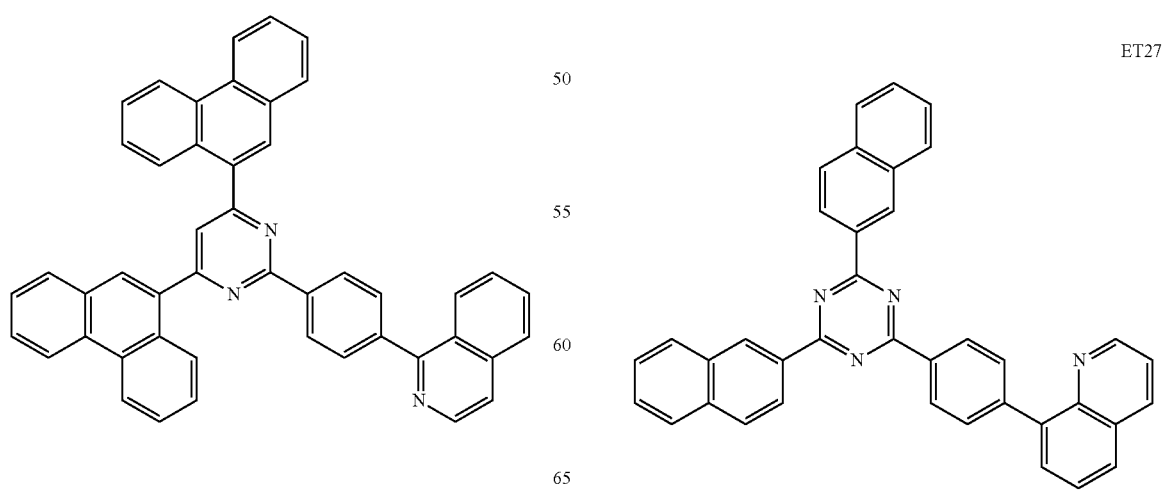

ET28
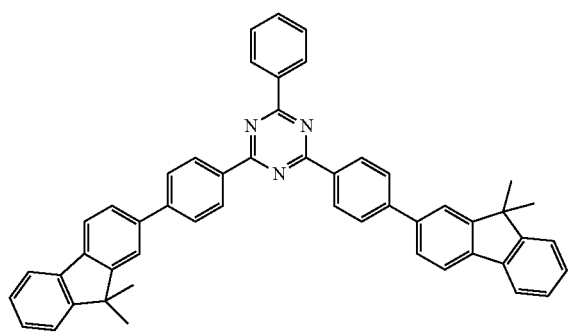
ET29
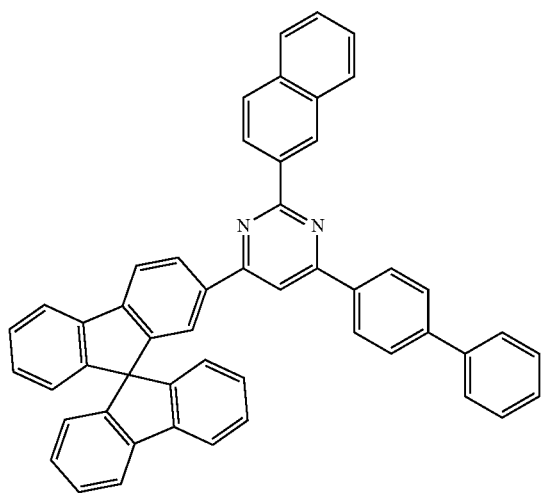
ET30
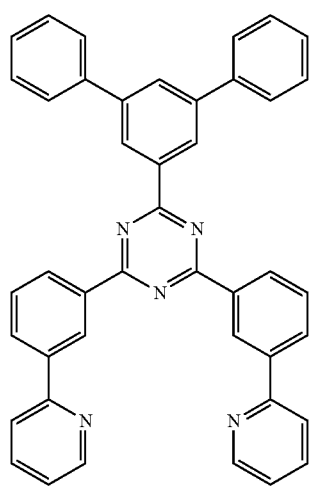
ET31
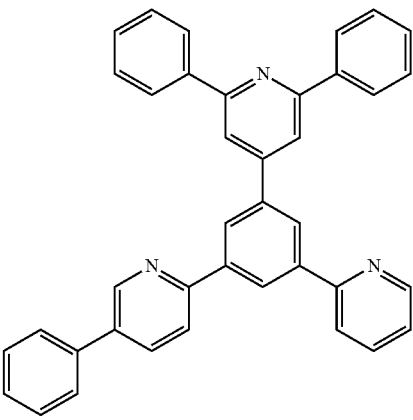
ET32
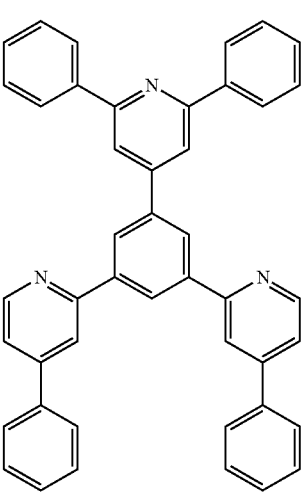
ET33
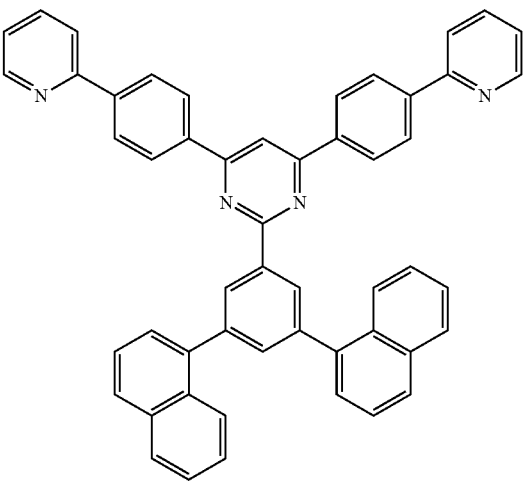

ET34
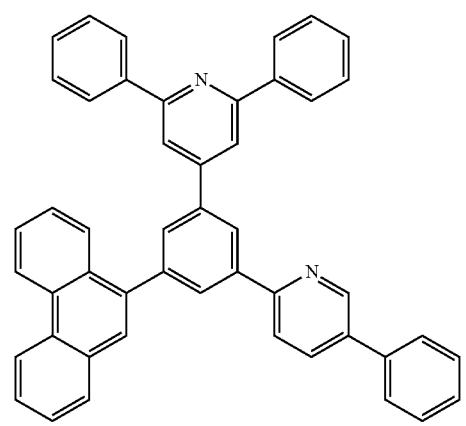
ET38
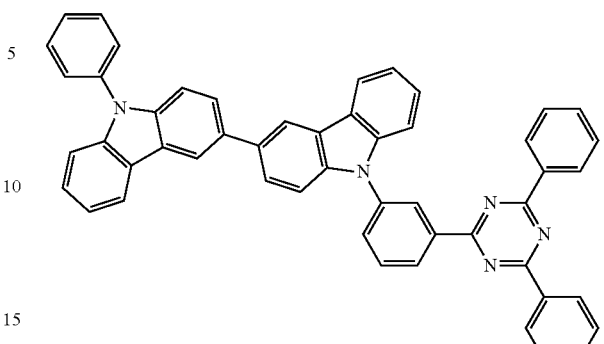
ET35
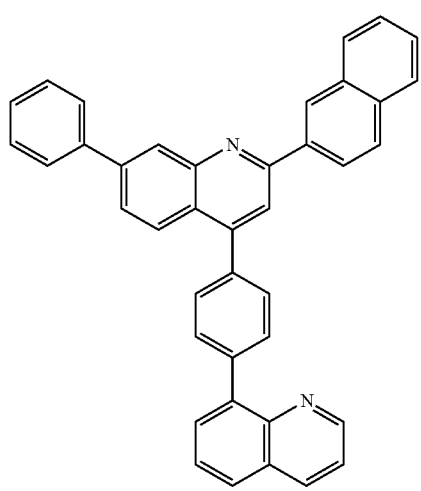
ET39
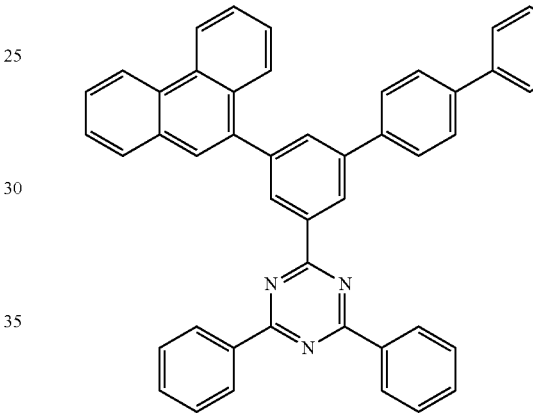
ET36
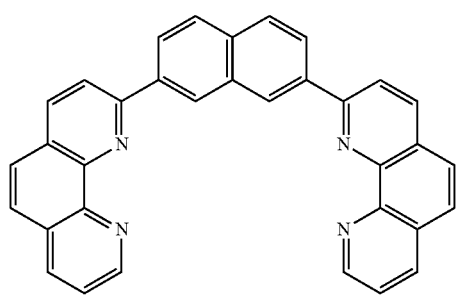
ET40
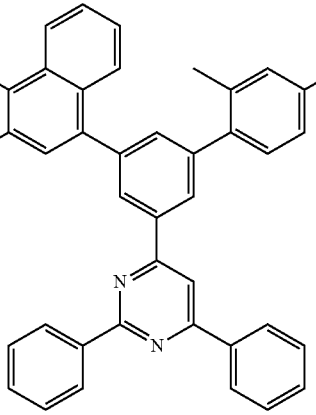
ET37
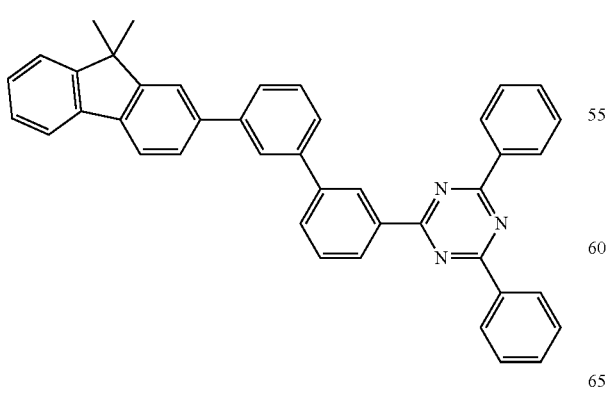
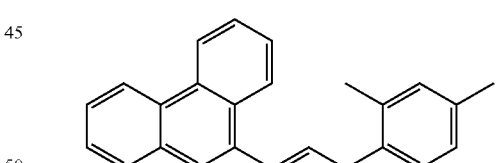

ET41
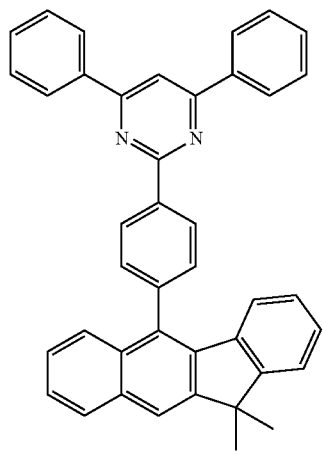
ET44
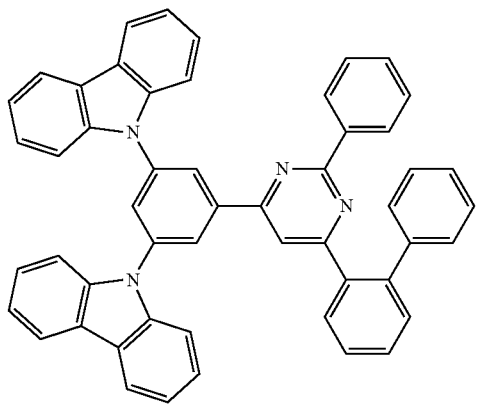
ET45
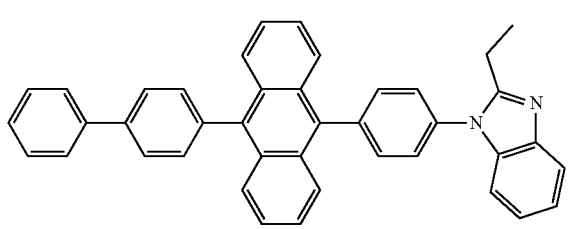
ET42
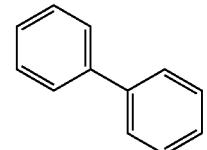
ET46
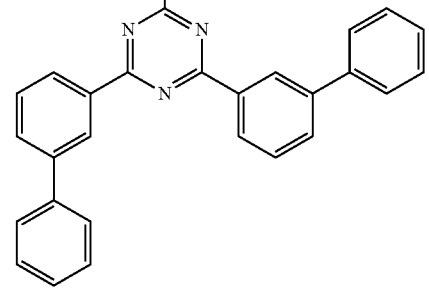
ET43
ET47
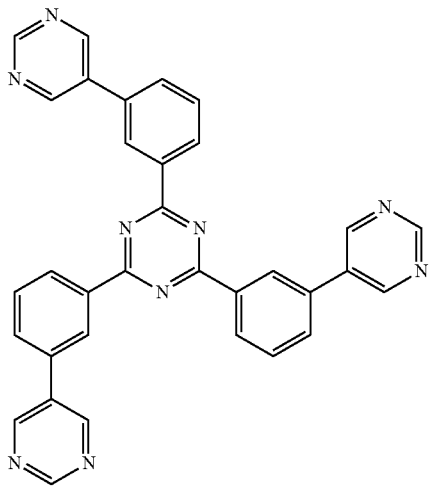

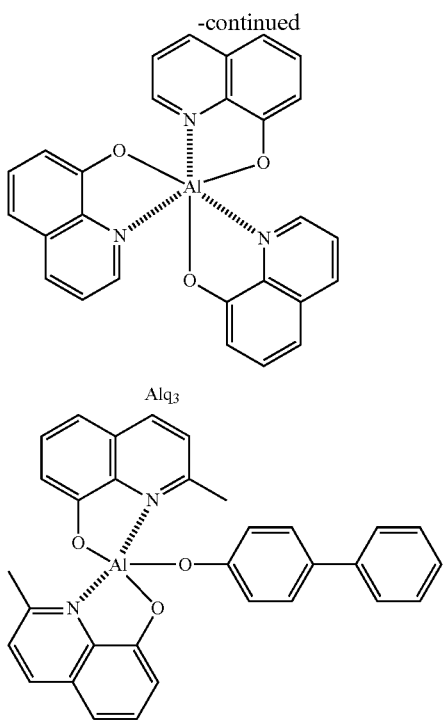

Alq₃

BAlq

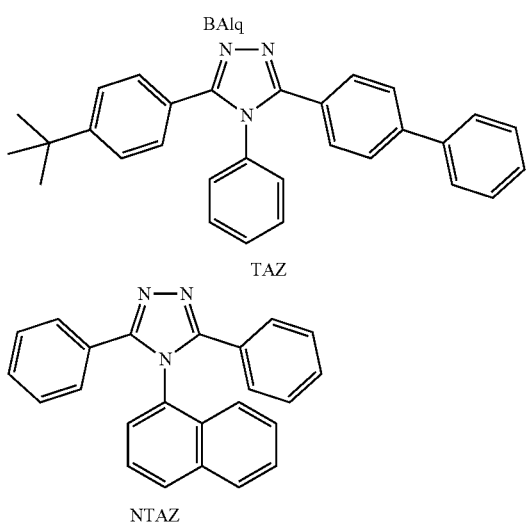

TAZ

NTAZ

A thickness of the electron transport region may be in a range of about 100 Å to about 5,000 Å. For example, the thickness of the electron transport region may be in a range of about 100 Å to about 4,000 Å. When the electron transport region includes a buffer layer, a hole blocking layer, an electron control layer, an electron transport layer, or any combination thereof, a thickness of the buffer layer, the hole blocking layer, or the electron control layer may each independently be in a range of about 20 Å to about 1000 Å, and a thickness of the electron transport layer may be in a range of about 100 Å to about 1000 Å. For example, the thicknesses of the buffer layer, the hole blocking layer, or the electron control layer may each independently be in a range of about 30 Å to about 300 Å. For example, the thickness of the electron transport layer may be in a range of about 150 Å to about 500 Å. When the thicknesses of the buffer layer, the hole blocking layer, the electron control layer, and/or the electron transport layer are within these ranges, satisfactory electron transporting characteristics may be obtained without a substantial increase in driving voltage.

The electron transport region (for example, the electron transport layer in the electron transport region) may further include, in addition to the materials described above, a metal-containing material.

The metal-containing material may include an alkali metal complex, alkaline earth metal complex, or any combination thereof. The metal ion of an alkali metal complex may be a Li ion, a Na ion, a K ion, a Rb ion, or a Cs ion, and the metal ion of an alkaline earth metal complex may be a Be ion, a Mg ion, a Ca ion, a Sr ion, or a Ba ion. A ligand coordinated with the metal ion of the alkali metal complex or the alkaline earth-metal complex may include a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxyphenyloxadiazole, a hydroxyphenylthiadiazole, a hydroxyphenylpyridine, a hydroxyphenylbenzimidazole, a hydroxyphenylbenzothiazole, a bipyridine, a phenanthroline, a cyclopentadiene, or any combination thereof.

For example, the metal-containing material may include a Li complex. The Li complex may include, for example, Compound ET-D1 (LiQ) or ET-D2:

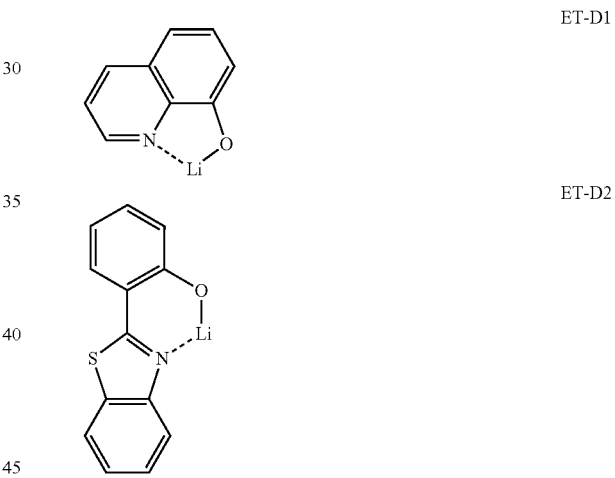

ET-D1

ET-D2

The electron transport region may include an electron injection layer that facilitates the injection of electrons from the second electrode 150. The electron injection layer may directly contact the second electrode 150.

The electron injection layer may have a structure consisting of a layer consisting of a single material, a structure consisting of a layer consisting of different materials, or a multi-layered structure including layers including different materials.

The electron injection layer may include an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof.

The alkali metal may include Li, Na, K, Rb, Cs, or any combination thereof. The alkaline earth metal may include Mg, Ca, Sr, Ba, or any combination thereof. The rare earth metal may include Sc, Y, Ce, Tb, Yb, Gd, or any combination thereof.

The alkali metal-containing compound, the alkaline earth metal-containing compound, and the rare earth metal-containing compound may be oxides, halides (for example, fluorides, chlorides, bromides, or iodides), or tellurides of the alkali metal, the alkaline earth metal, and the rare earth metal, or any combination thereof.

The alkali metal-containing compound may include alkali metal oxides, such as $Li_2O$, $Cs_2O$, or $K_2O$, or alkali metal halides, such as LiF, NaF, CsF, KF, LiI, NaI, CsI, or KI, or any combination thereof. The alkaline earth metal-containing compound may include an alkaline earth metal compound, such as BaO, SrO, CaO, $Ba_xSr_{1-x}O$ (x is a real number satisfying the condition of 0<x<1), $Ba_xCa_{1-x}O$ (x is a real number satisfying the condition of 0<x<1), or the like. The rare earth metal-containing compound may include $YbF_3$, $ScF_3$, $Sc_2O_3$, $Y_2O_3$, $Ce_2O_3$, $GdF_3$, $TbF_3$, $YbI_3$, $ScI_3$, $TbI_3$, or any combination thereof. In embodiments, the rare earth metal-containing compound may include a lanthanide metal telluride. Examples of the lanthanide metal telluride may include LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, and $Lu_2Te_3$.

The alkali metal complex, the alkaline earth-metal complex, and the rare earth metal complex may include one of ions of the alkali metal, ions of the alkaline earth metal, and ions of the rare earth metal and a ligand bonded to the metal ion, for example, hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenyl benzimidazole, hydroxyphenylbenzothiazole, bipyridine, phenanthroline, cyclopentadiene, or any combination thereof.

The electron injection layer may consist of an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof, as described above. In embodiments, the electron injection layer may further include an organic material (for example, a compound represented by Formula 601).

In embodiments, the electron injection layer may consist of an alkali metal-containing compound (for example, an alkali metal halide); or the electron injection layer may consist of an alkali metal-containing compound (for example, an alkali metal halide), and an alkali metal, an alkaline earth metal, a rare earth metal, or any combination thereof. In embodiments, the electron injection layer may be a KI:Yb co-deposited layer, an RbI:Yb co-deposited layer, or the like.

When the electron injection layer further includes an organic material, the alkali metal, the alkaline earth metal, the rare earth metal, the alkali metal-containing compound, the alkaline earth metal-containing compound, the rare earth metal-containing compound, the alkali metal complex, the alkaline earth-metal complex, the rare earth metal complex, or any combination thereof may be homogeneously or non-homogeneously dispersed in a matrix including the organic material.

A thickness of the electron injection layer may be in a range of about 1 Å to about 100 Å. For example, the thickness of the electron injection layer may be in a range of about 3 Å to about 90 Å. When the thickness of the electron injection layer is within the range described above, the electron injection layer may have satisfactory electron injection characteristics without a substantial increase in driving voltage.

[Second Electrode 150]

The second electrode 150 may be disposed on the interlayer 130 having such a structure. The second electrode 150 may be a cathode, which is an electron injection electrode, and as the material for the second electrode 150, a metal, an alloy, an electrically conductive compound, or any combination thereof, each having a low work function, may be used.

In embodiments, the second electrode 150 may include lithium (Li), silver (Ag), magnesium (Mg), aluminum (Al), aluminum-lithium (Al—Li), calcium (Ca), magnesium-indium (Mg—In), magnesium-silver (Mg—Ag), ytterbium (Yb), silver-ytterbium (Ag—Yb), ITO, IZO, or any combination thereof. The second electrode 150 may be a transmissive electrode, a semi-transmissive electrode, or a reflective electrode.

The second electrode 150 may have a single-layered structure or a multi-layered structure including two or more layers.

[Capping Layer]

A first capping layer may be located outside the first electrode 110, and/or a second capping layer may be located outside the second electrode 150. In embodiments, the light-emitting device 10 may have a structure in which the first capping layer, the first electrode 110, the interlayer 130, and the second electrode 150 are stacked in this stated order, a structure in which the first electrode 110, the interlayer 130, the second electrode 150, and the second capping layer are stacked in this stated order, or a structure in which the first capping layer, the first electrode 110, the interlayer 130, the second electrode 150, and the second capping layer are stacked in this stated order.

Light generated in an emission layer of the interlayer 130 of the light-emitting device 10 may be extracted toward the outside through the first electrode 110 (which may be a semi-transmissive electrode or a transmissive electrode) and through the first capping layer. Light generated in an emission layer of the interlayer 130 of the light-emitting device 10 may be extracted toward the outside through the second electrode 150 (which may be a semi-transmissive electrode or a transmissive electrode) and through the second capping layer.

The first capping layer and the second capping layer may each increase external emission efficiency according to the principle of constructive interference. Accordingly, the light extraction efficiency of the light-emitting device 10 may be increased, so that the emission efficiency of the light-emitting device 10 may be improved.

Each of the first capping layer and the second capping layer may include a material having a refractive index (at a wavelength of about 589 nm) equal to or greater than about 1.6.

The first capping layer and the second capping layer may each independently be an organic capping layer including an organic material, an inorganic capping layer including an inorganic material, or an organic-inorganic composite capping layer including an organic material and an inorganic material.

At least one selected from the first capping layer and the second capping layer may each independently include carbocyclic compounds, heterocyclic compounds, amine group-containing compounds, porphyrin derivatives, phthalocyanine derivatives, naphthalocyanine derivatives, alkali metal complexes, alkaline earth metal complexes, or any combination thereof. The carbocyclic compound, the heterocyclic compound, and the amine group-containing compound may each independently be optionally substituted with a substituent containing O, N, S, Se, Si, F, Cl, Br, I, or any combination thereof. In embodiments, at least one of the first capping layer and the second capping layer may each independently include an amine group-containing compound.

In embodiments, at least one of the first capping layer and the second capping layer may each independently include a compound represented by Formula 201, a compound represented by Formula 202, or any combination thereof.

In embodiments, at least one of the first capping layer and the second capping layer may each independently include one of Compounds HT28 to HT33, one of Compounds CP1 to CP6, β-NPB, or any combination thereof:

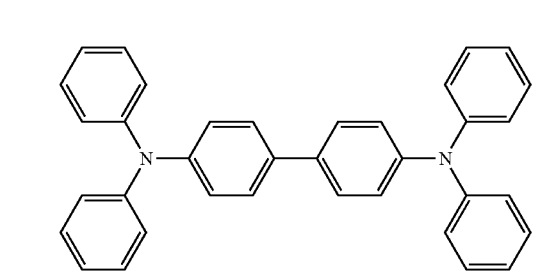
CP1

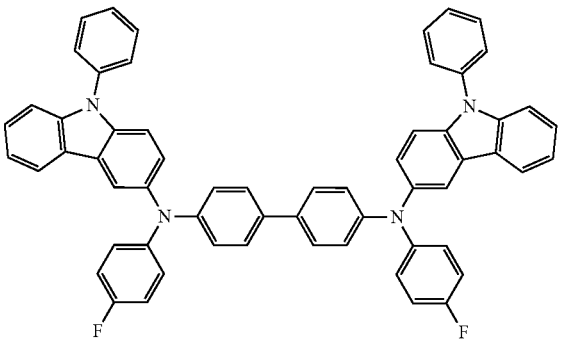
CP4

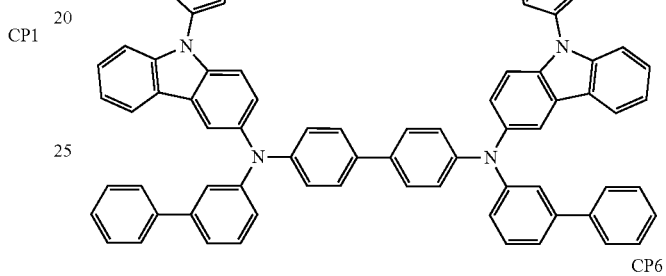
CP2

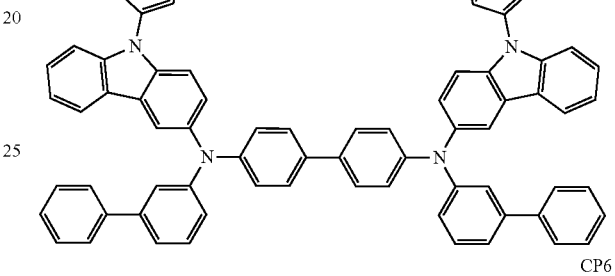
CP5

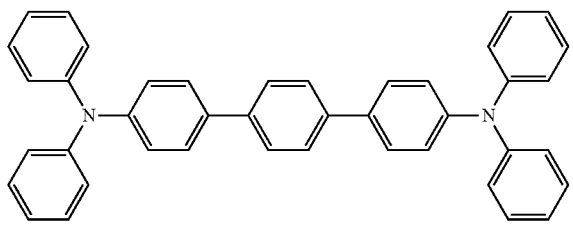
CP3

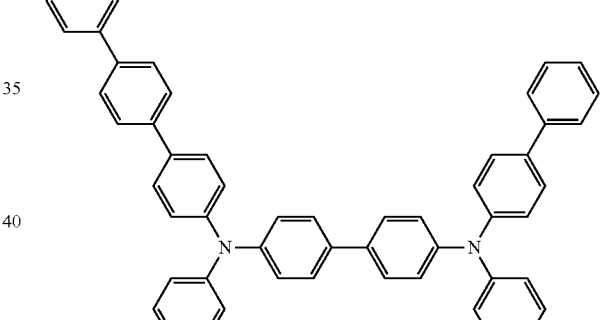
CP6

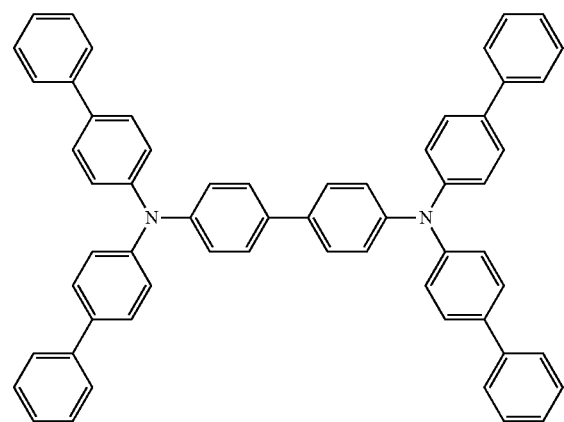

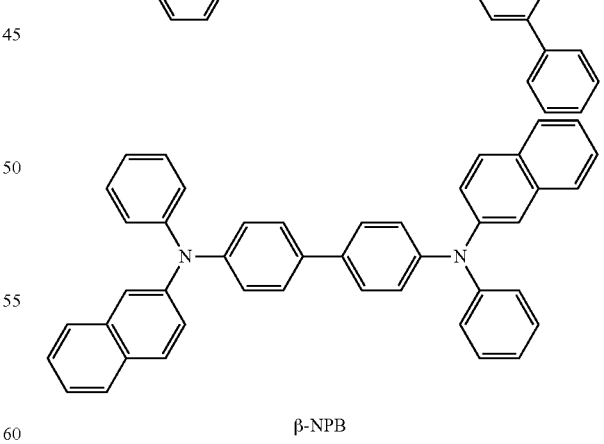
β-NPB

[Film]

The compound represented by Formula 1 may be included in various films. Therefore, according to an embodiment, a film including the compound represented by Formula 1 may be provided. The film may be, for example, an optical member (or a light control means) (e.g., a color filter, a color conversion member, a capping layer, an optical extraction efficiency improvement layer, an optional light absorbing layer, a polarizing layer, a quantum dot-containing layer, etc.), a light-shielding member (e.g., a light reflection layer, a light absorbing layer, etc.), or a protective member (e.g., an insulating layer, a dielectric layer, etc.).

[Electronic Apparatus]

The light-emitting device may be included in various electronic apparatuses. In embodiments, the electronic apparatus including the light-emitting device may be a light-emitting apparatus, an authentication apparatus, or the like.

The electronic apparatus (for example, light-emitting apparatus) may further include, in addition to the light-emitting device, a color filter, a color conversion layer, or a color filter and a color conversion layer. The color filter and/or the color conversion layer may be located in at least one traveling direction of light emitted from the light-emitting device. In embodiments, the light emitted from the light-emitting device may be blue light or white light. The light-emitting device may be the same as described above. In embodiments, the color conversion layer may include quantum dots. The quantum dot may be, for example, a quantum dot as described herein.

The electronic apparatus may include a first substrate. The first substrate may include subpixels, the color filter may include color filter areas respectively corresponding to the subpixels, and the color conversion layer may include color conversion areas respectively corresponding to the subpixels.

A pixel-defining film may be located among the subpixels to define each of the subpixels.

The color filter may further include color filter areas and light-shielding patterns located among the color filter areas, and the color conversion layer may include color conversion areas and light-shielding patterns located among the color conversion areas.

The color filter areas (or the color conversion areas) may include a first area emitting first color light, a second area emitting second color light, and/or a third area emitting third color light, and the first color light, the second color light, and/or the third color light may have different maximum emission wavelengths from one another. In embodiments, the first color light may be red light, the second color light may be green light, and the third color light may be blue light. In embodiments, the color filter areas (or the color conversion areas) may include quantum dots. For example, the first area may include a red quantum dot, the second area may include a green quantum dot, and the third area may not include a quantum dot. The quantum dot may be the same as described in the specification. The first area, the second area, and/or the third area may each include a scatterer.

In embodiments, the light-emitting device may emit first light, the first area may absorb the first light to emit first first-color light, the second area may absorb the first light to emit second first-color light, and the third area may absorb the first light to emit third first-color light. In this regard, the first first-color light, the second first-color light, and the third first-color light may each have different maximum emission wavelengths. For example, the first light may be blue light, the first first-color light may be red light, the second first-color light may be green light, and the third first-color light may be blue light.

The electronic apparatus may further include a thin-film transistor in addition to the light-emitting device as described above. The thin-film transistor may include a source electrode, a drain electrode, and an active layer, wherein any one of the source electrode and the drain electrode may be electrically connected to any one of the first electrode and the second electrode of the light-emitting device.

The thin-film transistor may further include a gate electrode, a gate insulating film, etc.

The active layer may include crystalline silicon, amorphous silicon, organic semiconductor, oxide semiconductor, or the like.

The electronic apparatus may further include a sealing portion for sealing the light-emitting device. The sealing portion may be placed between the color filter and/or the color conversion layer the light-emitting device. The sealing portion may allow light from the light-emitting device to be extracted to the outside, and may simultaneously prevent ambient air and moisture from penetrating into the light-emitting device. The sealing portion may be a sealing substrate including a transparent glass substrate or a plastic substrate. The sealing portion may be a thin-film encapsulation layer including at least one of an organic layer and an inorganic layer. When the sealing portion is a thin film encapsulation layer, the electronic apparatus may be flexible.

Various functional layers may be additionally located on the sealing portion, in addition to the color filter and/or the color conversion layer, according to the use of the electronic apparatus. The functional layers may include a touch screen layer, a polarizing layer, an authentication apparatus, and the like. The touch screen layer may be a pressure-sensitive touch screen layer, a capacitive touch screen layer, or an infrared touch screen layer. The authentication apparatus may be, for example, a biometric authentication apparatus that authenticates an individual by using biometric information of a living body (for example, fingertips, pupils, etc.).

The authentication apparatus may further include, in addition to the light-emitting device, a biometric information collector.

The electronic apparatus may be applied to various displays, such as light sources, lighting, personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement devices, pulse wave measurement devices, electrocardiogram displays, ultrasonic diagnostic devices, or endoscope displays), fish finders, various measuring instruments, meters (for example, meters for a vehicle, an aircraft, and a vessel), projectors, and the like.

Figure 3:
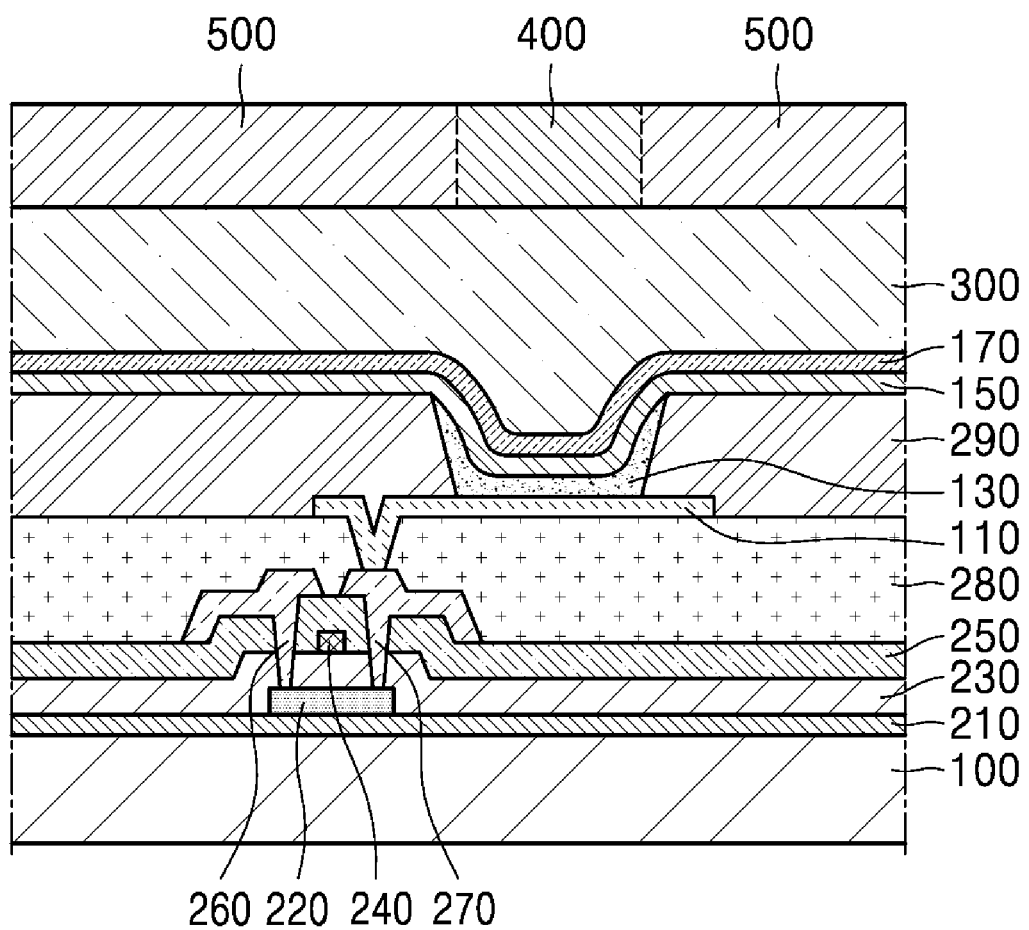
FIG. 3 is a schematic cross-sectional view of the structure of an electronic apparatus according to another embodiment.

[Description of FIGS. 2 and 3]

FIG. 2 is a schematic cross-sectional view showing an electronic apparatus according to an embodiment of the disclosure.

The electronic apparatus of FIG. 2 includes a substrate 100, a thin-film transistor (TFT), a light-emitting device, and an encapsulation portion 300 that seals the light-emitting device.

The substrate 100 may be a flexible substrate, a glass substrate, or a metal substrate. A buffer layer 210 may be formed on the substrate 100. The buffer layer 210 may prevent penetration of impurities through the substrate 100 and may provide a flat surface on the substrate 100.

A TFT may be located on the buffer layer 210. The TFT may include an active layer 220, a gate electrode 240, a source electrode 260, and a drain electrode 270.

The active layer 220 may include an inorganic semiconductor such as silicon or polysilicon, an organic semiconductor, or an oxide semiconductor, and may include a source region, a drain region, and a channel region.

A gate insulating film 230 for insulating the active layer 220 from the gate electrode 240 may be located on the active layer 220, and the gate electrode 240 may be located on the gate insulating film 230.

An interlayer insulating film 250 is located on the gate electrode 240. The interlayer insulating film 250 may be placed between the gate electrode 240 and the source electrode 260 to insulate the gate electrode 240 from the source electrode 260 and between the gate electrode 240 and the drain electrode 270 to insulate the gate electrode 240 from the drain electrode 270.

The source electrode 260 and the drain electrode 270 may be located on the interlayer insulating film 250. The interlayer insulating film 250 and the gate insulating film 230 may be formed to expose the source region and the drain region of the active layer 220, and the source electrode 260 and the drain electrode 270 may be in contact with the exposed portions of the source region and the drain region of the active layer 220.

The TFT is electrically connected to a light-emitting device to drive the light-emitting device, and is covered by a passivation layer 280. The passivation layer 280 may include an inorganic insulating film, an organic insulating film, or any combination thereof. A light-emitting device is provided on the passivation layer 280. The light-emitting device may include a first electrode 110, an interlayer 130, and a second electrode 150.

The first electrode 110 may be formed on the passivation layer 280. The passivation layer 280 does not completely cover the drain electrode 270 and may expose a portion of the drain electrode 270, and the first electrode 110 may be electrically connected to the exposed portion of the drain electrode 270.

A pixel-defining layer 290 containing an insulating material may be located on the first electrode 110. The pixel-defining layer 290 may expose a region of the first electrode 110, and an interlayer 130 may be formed in the exposed region of the first electrode 110. The pixel-defining layer 290 may be a polyimide or polyacrylic organic film. Although not shown in FIG. 2, at least some layers of the interlayer 130 may extend beyond the upper portion of the pixel-defining layer 290 to be provided in the form of a common layer.

The second electrode 150 may be located on the interlayer 130, and a capping layer 170 may be additionally formed on the second electrode 150. The capping layer 170 may be formed to cover the second electrode 150.

The encapsulation portion 300 may be located on the capping layer 170. The encapsulation portion 300 may be located on a light-emitting device to protect the light-emitting device from moisture and/or oxygen. The encapsulation portion 300 may include: an inorganic film including silicon nitride (SiNx), silicon oxide (SiOx), indium tin oxide, indium zinc oxide, or any combination thereof, an organic film including polyethylene terephthalate, polyethylene naphthalate, polycarbonate, polyimide, polyethylene sulfonate, polyoxymethylene, polyarylate, hexamethyldisiloxane, an acrylic-based resin (for example, polymethyl methacrylate, polyacrylic acid, or the like), an epoxy-based resin (for example, aliphatic glycidyl ether (AGE), or the like), or any combination thereof, or any combination of the inorganic film and the organic film.

FIG. 3 shows a schematic cross-sectional view showing an electronic apparatus according to an embodiment of the disclosure.

The light-emitting apparatus of FIG. 3 is the same as the light-emitting apparatus of FIG. 2, except that a light-shielding pattern 500 and a functional region 400 are additionally located on the encapsulation portion 300. The functional region 400 may be a color filter area, a color conversion area, or a combination of the color filter area and the color conversion area. In embodiments, the light-emitting device included in the electronic apparatus of FIG. 3 may be a tandem light-emitting device.

[Manufacture Method]

Respective layers included in the hole transport region, the emission layer, and respective layers included in the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, an emission layer, and layers constituting the electron transport region are formed by vacuum deposition, the deposition may be performed at a deposition temperature of about 100° C. to about 500° C., a vacuum degree of about 10-8 torr to about 10-3 torr, and a deposition speed of about 0.01 Å/sec to about 100 Å/sec, depending on a material to be included in a layer to be formed and the structure of a layer to be formed.

Definitions of Terms

The term "$C_3$-$C_{60}$ carbocyclic group" as used herein may be a cyclic group consisting only of carbon as a ring-forming atom and having three to sixty carbon atoms, and the term "$C_1$-$C_{60}$ heterocyclic group" as used herein may be a cyclic group that has one to sixty carbon atoms and further has, in addition to carbon, at least one heteroatom as a ring-forming atom. The $C_3$-$C_{60}$ carbocyclic group and the $C_1$-$C_{60}$ heterocyclic group may each be a monocyclic group consisting of one ring or a polycyclic group in which two or more rings are condensed with each other. For example, a $C_1$-$C_{60}$ heterocyclic group may have 3 to 61 ring-forming atoms.

The term "cyclic group" as used herein may include the $C_3$-$C_{60}$ carbocyclic group, and the $C_1$-$C_{60}$ heterocyclic group.

The term "π electron-rich $C_3$-$C_{60}$ cyclic group" as used herein may be a cyclic group that has three to sixty carbon atoms and may not include *—N=*' as a ring-forming moiety, and the term "π electron-deficient nitrogen-containing $C_1$-$C_{60}$ cyclic group" as used herein may be a heterocyclic group that has one to sixty carbon atoms and may include *—N=*' as a ring-forming moiety.

For example,
the $C_3$-$C_{60}$ carbocyclic group may be a T1 group or a condensed cyclic group in which two or more T1 groups are condensed with each other (for example, a cyclopentadiene group, an adamantane group, a norbornane group, a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indenophenanthrene group, or an indenoanthracene group), the $C_1$-$C_{60}$ heterocyclic group may be a T2 group, a condensed cyclic group in which two or more T2 groups are condensed with each other, or a condensed cyclic group in which at least one T2 group and at least one T1 group are condensed with each other (for example, a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.), the π electron-rich $C_3$-$C_{60}$ cyclic group may be a T1 group, a condensed cyclic group in which two or more T1 groups are condensed with each other, a T3 group, a condensed cyclic group in which two or more T3 groups are condensed with each other, or a condensed cyclic group in which at least one T3 group and at least one T1 group are condensed with each other (for example, the $C_3$-$C_{60}$ carbocyclic group, a 1H-pyrrole group, a silole group, a borole group, a 2H-pyrrole group, a 3H-pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, etc.), the π electron-deficient nitrogen-containing $C_1$-$C_{60}$ cyclic group may be a T4 group, a condensed cyclic group in which two or more T4 groups are condensed with each other, a condensed cyclic group in which at least one T4 group and at least one T1 group are condensed with each other, a condensed cyclic group in which at least one T4 group and at least one T3 group are condensed with each other, or a condensed cyclic group in which at least one T4 group, at least one T1 group, and at least one T3 group are condensed with one another (for example, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.), wherein the T1 group may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane (or a bicyclo[2.2.1]heptane) group, a norbornene group, a bicyclo[1.1.1]pentane group, a bicyclo[2.1.1]hexane group, a bicyclo[2.2.2] octane group, or a benzene group, the T2 group may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, a tetrazine group, a pyrrolidine group, an imidazolidine group, a dihydropyrrole group, a piperidine group, a tetrahydropyridine group, a dihydropyridine group, a hexahydropyrimidine group, a tetrahydropyrimidine group, a dihydropyrimidine group, a piperazine group, a tetrahydropyrazine group, a dihydropyrazine group, a tetrahydropyridazine group, or a dihydropyridazine group, the T3 group may be a furan group, a thiophene group, a 1H-pyrrole group, a silole group, or a borole group, and the T4 group may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

The terms "cyclic group," "$C_3$-$C_{60}$ carbocyclic group," "$C_1$-$C_{60}$ heterocyclic group," "π electron-rich $C_3$-$C_{60}$ cyclic group," or "π electron-deficient nitrogen-containing $C_1$-$C_{60}$ cyclic group" as used herein may be a group condensed to any cyclic group or a polyvalent group (for example, a divalent group, a trivalent group, a tetravalent group, etc.), depending on the structure of a formula in connection with which the terms are used. In embodiments, "a benzene group" may be a benzo group, a phenyl group, a phenylene group, or the like, which may be easily understood by one of ordinary skill in the art according to the structure of a formula including the "benzene group."

Examples of the monovalent $C_3$-$C_{60}$ carbocyclic group and the monovalent $C_1$-$C_{60}$ heterocyclic group may include a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, and examples of the divalent $C_3$-$C_{60}$ carbocyclic group and the divalent $C_1$-$C_{60}$ heterocyclic group may include a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic condensed polycyclic group, and a divalent non-aromatic condensed heteropolycyclic group.

The term "$C_1$-$C_{60}$ alkyl group" as used herein may be a linear or branched aliphatic hydrocarbon monovalent group that has one to sixty carbon atoms, and examples thereof may include a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group. The term "$C_1$-$C_{60}$ alkylene group" as used herein may be a divalent group having a same structure as the $C_1$-$C_{60}$ alkyl group.

The term "$C_2$-$C_{60}$ alkenyl group" as used herein may be a monovalent hydrocarbon group having at least one carbon-carbon double bond in the middle or at the terminus of the $C_2$-$C_{60}$ alkyl group, and examples thereof may include an ethenyl group, a propenyl group, and a butenyl group. The term "$C_2$-$C_{60}$ alkenylene group" as used herein refers to a divalent group having a same structure as the $C_2$-$C_{60}$ alkenyl group.

The term "$C_2$-$C_{60}$ alkynyl group" as used herein may be a monovalent hydrocarbon group having at least one carbon-carbon triple bond in the middle or at the terminus of the $C_2$-$C_{60}$ alkyl group, and examples thereof may include an ethynyl group and a propynyl group. The term "$C_2$-$C_{60}$ alkynylene group" as used herein may be a divalent group having a same structure as the $C_2$-$C_{60}$ alkynyl group.

The term "$C_1$-$C_{60}$ alkoxy group" as used herein may be a monovalent group represented by —$OA_{101}$ (wherein $A_{101}$ is a $C_1$-$C_{60}$ alkyl group), and examples thereof may include a methoxy group, an ethoxy group, and an isopropyloxy group.

The term "$C_3$-$C_{10}$ cycloalkyl group" as used herein may be a monovalent saturated hydrocarbon cyclic group having 3 to 10 carbon atoms, and examples thereof may include a cyclopropyl group, a cyclobutyl group, a cyclopentyl group, a cyclohexyl group, a cycloheptyl group, a cyclooctyl group, an adamantanyl group, a norbornanyl group (or bicyclo[2.2.1]heptyl group), a bicyclo[1.1.1]pentyl group, a bicyclo[2.1.1]hexyl group, and a bicyclo[2.2.2]octyl group. The term "$C_3$-$C_{10}$ cycloalkylene group" as used herein may be a divalent group having a same structure as the $C_3$-$C_{10}$ cycloalkyl group.

The term "$C_1$-$C_{10}$ heterocycloalkyl group" as used herein may be a monovalent cyclic group that further includes, in addition to a carbon atom, at least one heteroatom as a ring-forming atom and has 1 to 10 carbon atoms, and examples thereof may include a 1,2,3,4-oxatriazolidinyl group, a tetrahydrofuranyl group, and a tetrahydrothiophenyl group. The term "$C_1$-$C_{10}$ heterocycloalkylene group" as used herein may be a divalent group having a same structure as the $C_1$-$C_{10}$ heterocycloalkyl group.

The term "$C_3$-$C_{10}$ cycloalkenyl group" as used herein may be a monovalent cyclic group that has three to ten carbon atoms and at least one carbon-carbon double bond in the ring thereof and no aromaticity, and examples thereof may include a cyclopentenyl group, a cyclohexenyl group, and a cycloheptenyl group. The term "$C_3$-$C_{10}$ cycloalkenylene group" as used herein may be a divalent group having a same structure as the $C_3$-$C_{10}$ cycloalkenyl group.

The term "$C_1$-$C_{10}$ heterocycloalkenyl group" as used herein may be a monovalent cyclic group that has, in addition to a carbon atom, at least one heteroatom as a ring-forming atom, 1 to 10 carbon atoms, and at least one carbon-carbon double bond in the cyclic structure thereof. Examples of the $C_1$-$C_{10}$ heterocycloalkenyl group may include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein may be a divalent group having a same structure as the $C_1$-$C_{10}$ heterocycloalkenyl group.

The term "$C_6$-$C_{60}$ aryl group" as used herein may be a monovalent group having a carbocyclic aromatic system having six to sixty carbon atoms, and the term "$C_6$-$C_{60}$ arylene group" as used herein may be a divalent group having a carbocyclic aromatic system having six to sixty carbon atoms. Examples of the $C_6$-$C_{60}$ aryl group may include a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, and an ovalenyl group. When the $C_6$-$C_{60}$ aryl group and the $C_6$-$C_{60}$ arylene group each include two or more rings, the rings may be condensed with each other.

The term "$C_1$-$C_{60}$ heteroaryl group" as used herein may be a monovalent group having a heterocyclic aromatic system that has, in addition to a carbon atom, at least one heteroatom as a ring-forming atom, and 1 to 60 carbon atoms. The term "$C_1$-$C_{60}$ heteroarylene group" as used herein may be a divalent group having a heterocyclic aromatic system that has, in addition to a carbon atom, at least one heteroatom as a ring-forming atom, and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, and a naphthyridinyl group. When the $C_1$-$C_{60}$ heteroaryl group and the $C_1$-$C_{60}$ heteroarylene group each include two or more rings, the rings may be condensed with each other.

The term "monovalent non-aromatic condensed polycyclic group" as used herein may be a monovalent group having two or more rings condensed to each other, only carbon atoms (for example, having 8 to 60 carbon atoms) as ring-forming atoms, and no aromaticity in its molecular structure when considered as a whole. Examples of the monovalent non-aromatic condensed polycyclic group may include an indenyl group, a fluorenyl group, a spiro-bifluorenyl group, a benzofluorenyl group, an indenophenanthrenyl group, and an indeno anthracenyl group. The term "divalent non-aromatic condensed polycyclic group" as used herein may be a divalent group having a same structure as a monovalent non-aromatic condensed polycyclic group.

The term "monovalent non-aromatic condensed heteropolycyclic group" as used herein may be a monovalent group having two or more rings condensed to each other, at least one heteroatom other than carbon atoms (for example, having 1 to 60 carbon atoms), as a ring-forming atom, and no aromaticity in its molecular structure when considered as a whole. Examples of the monovalent non-aromatic condensed heteropolycyclic group may include a pyrrolyl group, a thiophenyl group, a furanyl group, an indolyl group, a benzoindolyl group, a naphtho indolyl group, an isoindolyl group, a benzoisoindolyl group, a naphthoisoindolyl group, a benzosilolyl group, a benzothiophenyl group, a benzofuranyl group, a carbazolyl group, a dibenzosilolyl group, a dibenzothiophenyl group, a dibenzofuranyl group, an azacarbazolyl group, an azafluorenyl group, an azadibenzosilolyl group, an azadibenzothiophenyl group, an azadibenzofuranyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a benzopyrazolyl group, a benzimidazolyl group, a benzoxazolyl group, a benzothiazolyl group, a benzoxadiazolyl group, a benzothiadiazolyl group, an imidazopyridinyl group, an imidazopyrimidinyl group, an imidazotriazinyl group, an imidazopyrazinyl group, an imidazopyridazinyl group, an indenocarbazolyl group, an indolocarbazolyl group, a benzofurocarbazolyl group, a benzothienocarbazolyl group, a benzosilolocarbazolyl group, a benzoindolocarbazolyl group, a benzocarbazolyl group, a benzonaphthofuranyl group, a benzonaphthothiophenyl group, a benzonaphthosilolyl group, a benzofurodibenzofuranyl group, a benzofurodibenzothiophenyl group, and a benzothienodibenzothiophenyl group. The term "divalent non-aromatic condensed heteropolycyclic group" as used herein may be a divalent group having a same structure as a monovalent non-aromatic condensed heteropolycyclic group.

The term "$C_6$-$C_{60}$ aryloxy group" as used herein may be represented by —$OA_{102}$ (wherein $A_{102}$ is a $C_6$-$C_{60}$ aryl group), and the term "$C_6$-$C_{60}$ arylthio group" as used herein may be represented by —$SA_{103}$ (wherein $A_{103}$ is a $C_6$-$C_{60}$ aryl group).

The term "$C_7$-$C_{60}$ aryl alkyl group" as used herein may be represented by -$(A_{104})(A_{105})$ (where $A_{104}$ may be a $C_1$-$C_{54}$ alkylene group, and $A_{105}$ may be a $C_6$-$C_{59}$ aryl group), and the term "$C_2$-$C_{60}$ heteroaryl alkyl group" as used herein may be represented by -$(A_{106})(A_{107})$ (where $A_{106}$ may be a $C_1$-$C_{59}$ alkylene group, and $A_{107}$ may be a $C_1$-$C_{59}$ heteroaryl group).

The term "$R_{10a}$" as used herein may be:
deuterium (-D), —F, —Cl, —Br, —I, a hydroxyl group, a cyano group, or a nitro group;
a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof, or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$, $Q_1$ to $Q_3$, $Q_{11}$ to $Q_{13}$, $Q_{21}$ to $Q_{23}$ and $Q_{31}$ to $Q_{33}$ used herein may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, a $C_7$-$C_{60}$ aryl alkyl group; or a $C_2$-$C_{60}$ heteroaryl alkyl group.

The term "heteroatom" as used herein may be any atom other than a carbon atom or a hydrogen atom. Examples of the heteroatom may include O, S, N, P, Si, B, Ge, Se, and any combination thereof.

The term "the third-row transition metal" as used herein may include hafnium (Hf), tantalum (Ta), tungsten(W), rhenium (Re), osmium (Os), iridium (Ir), platinum (Pt), gold (Au), etc.

The term "Ph" as used herein refers to a phenyl group, the term "Me" as used herein refers to a methyl group, the term "Et" as used herein refers to an ethyl group, the term "ter-Bu" or "Bu$^t$" as used herein refers to a tert-butyl group, and the term "OMe" as used herein refers to a methoxy group.

The term "biphenyl group" as used herein may be "a phenyl group substituted with a phenyl group." For example, the "biphenyl group" may be a substituted phenyl group having a $C_6$-$C_{60}$ aryl group as a substituent.

The term "terphenyl group" as used herein may be "a phenyl group substituted with a biphenyl group". For example, the "terphenyl group" may be a substituted phenyl group having, as a substituent, a $C_6$-$C_{60}$ aryl group substituted with a $C_6$-$C_{60}$ aryl group.

In the specification, * and *' as used herein, unless defined otherwise, each represent a binding site to a neighboring atom in a corresponding formula or moiety.

Hereinafter, a compound according to embodiments and a light-emitting device according to embodiments will be described in detail with reference to Synthesis Examples and Examples. The wording "B was used instead of A" used in describing Synthesis Examples refers to that an identical molar equivalent of B was used in place of A.

EXAMPLES

Synthesis Example 1: Synthesis of Compound 1

Synthesis Example 2: Synthesis of Compound 5

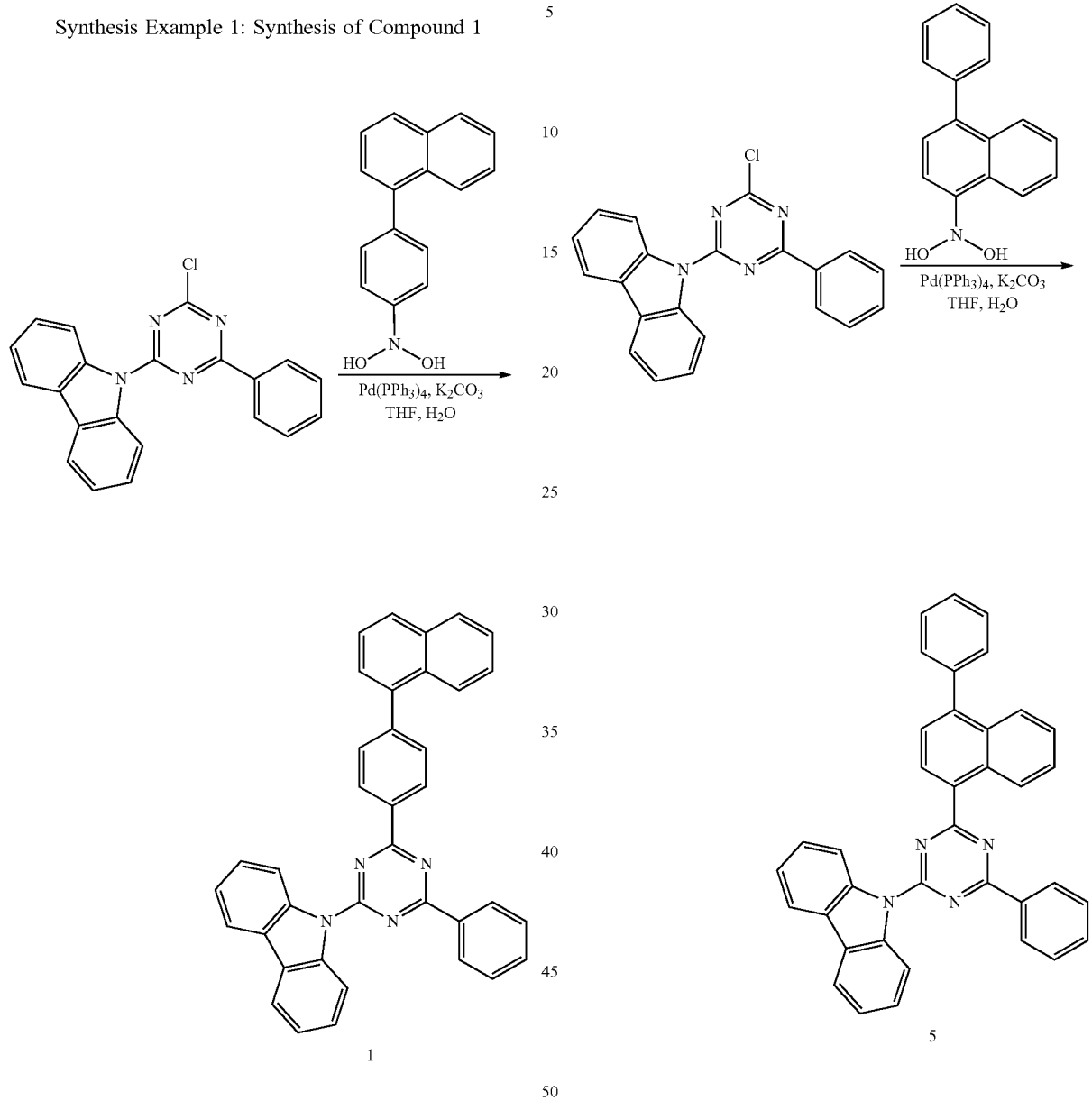

In a nitrogen atmosphere, 9-(4-chloro-6-phenyl-1,3,5-triazin-2-yl)-9H-carbazole (5.00 g, 0.0140 mol), and (4-(naphthalen-1-yl)phenyl)boronic acid (5.50 g, 0.0154 mol) were completely dissolved in THF (200 ml) in a 500 ml round-bottom flask. 2M $K_2CO_3$ aqueous solution (100 ml) was added to the solution, $Pd(PPh_3)_4$ (0.50 g, 3 mol %) was added thereto, and the solution was refluxed for 8 hours. The reaction of the reaction product was completed using $H_2O$, $CH_2Cl_2$ was extracted therefrom, and was dried using anhydrous $MgSO_4$. The dried product was subjected to column chromatography using a solvent of a mixture of $CH_2Cl_2$ and n-hexane (volume ratio 1:10), thereby preparing Compound 1 (5.88 g, 80%).

H-NMR ($CdCl_3$): 8.95 (1H, d), 8.55-8.50 (2H, m), 8.36 (2H, m), 8.20 (2H, m), 8.10 (1H, d), 7.96-7.93 (3H, m), 7.75 (1H, t), 7.54-7.52 (6H, m), 7.39-7.35 (2H, m), 7.25-7.16 (4H, m) $C_{37}H_{24}N_4$ m/z: 524.20

Compound 5 (5.00 g, 68%) was prepared in the same manner as in Synthesis Example 1, except that (4-phenylnaphthalen-1-yl)boronic acid (5.50 g, 0.0154 mol) was used instead of (4-(naphthalen-1-yl)phenyl)boronic acid (5.50 g, 0.0154 mol).

H-NMR ($CdCl_3$): 9.02-8.95 (2H, d), 8.55 (1H, d), 8.36 (2H, m), 8.20 (1H, m), 8.06 (1H, d), 7.94 (1H, d), 7.84-7.77 (3H, m), 7.54-7.35 (11H, m), 7.20-7.16 (2H, m) $C_{37}H_{24}N_4$ m/z: 524.20

Synthesis Example 3: Synthesis of Compound 7

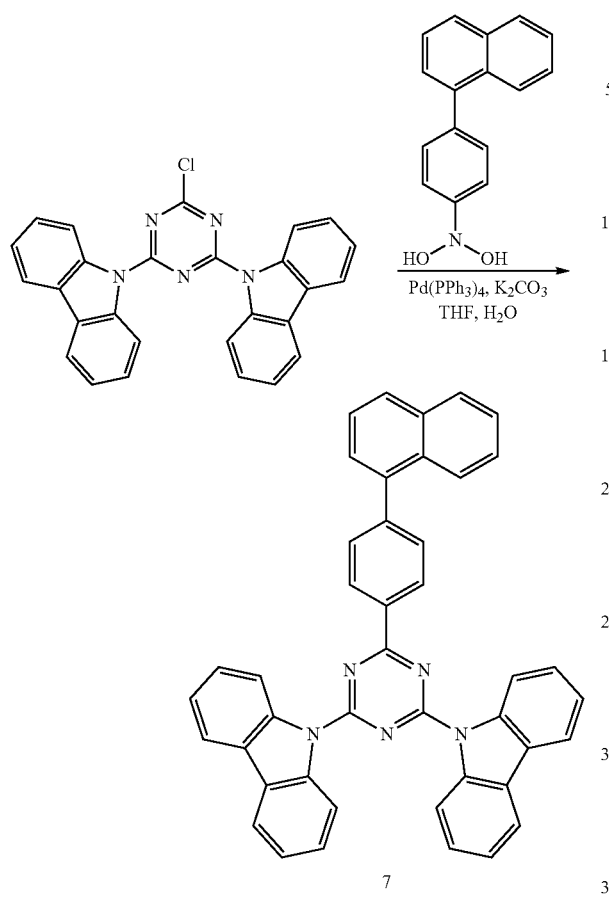

Compound 7 (5.15 g, 75%) was prepared in the same manner as in Synthesis Example 1, except that 9,9'-(6-chloro-1,3,5-triazine-2,4-diyl)bis(9H-carbazole) (5.00 g, 0.0112 mol) and (4-(naphthalen-1-yl)phenyl)boronic acid (3.05 g, 0.0123 mol) were used instead of 9-(4-chloro-6-phenyl-1,3,5-triazin-2-yl)-9H-carbazole (5.00 g, 0.0140 mol) and (4-(naphthalen-1-yl)phenyl)boronic acid (5.50 g, 0.0154 mol).

H-NMR (CdCl$_3$): 8.95 (1H, d), 8.55-8.50 (3H, m), 8.20-8.18 (3H, m), 8.10 (1H, d), 7.96-7.93 (4H, m), 7.77 (1H, t), 7.52-7.50 (5H, m), 7.39-7.20 (9H, m) C$_{43}$H$_{27}$N$_5$ m/z: 613.23

Synthesis Example 4: Synthesis of Compound 11

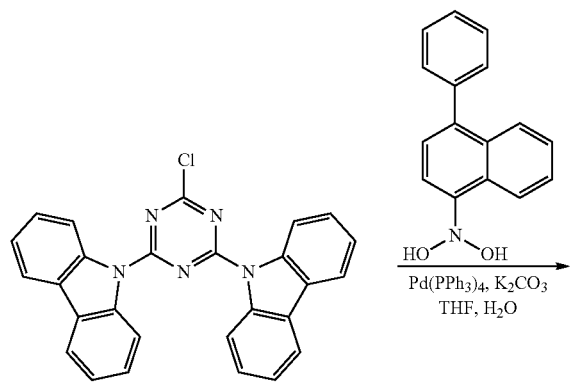

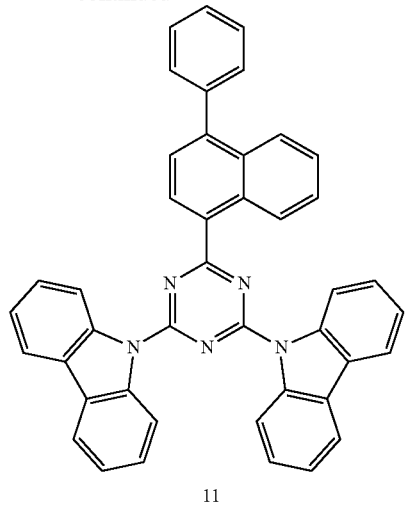

Compound 11 (3.78 g, 55%) was prepared in the same manner as in Synthesis Example 1, except that 9,9'-(6-chloro-1,3,5-triazine-2,4-diyl)bis(9H-carbazole) (5.00 g, 0.0112 mol), and (4-phenylnaphthalen-1-yl)boronic acid (3.05 g, 0.0123 mol) were used instead of 9-(4-chloro-6-phenyl-1,3,5-triazin-2-yl)-9H-carbazole (5.00 g, 0.0140 mol) and (4-(naphthalen-1-yl)phenyl)boronic acid (5.50 g, 0.0154 mol).

H-NMR (CdCl$_3$): 9.02-8.95 (2H, d), 8.55 (2H, d), 8.19 (2H, d), 8.06 (1H, d), 7.94 (2H, d), 7.82-7.79 (3H, m), 7.58-7.35 (11H, m), 7.20-7.15 (4H, m) C$_{43}$H$_{27}$N$_5$ m/z: 613.23

Synthesis methods for compounds other than the compounds shown in Synthesis Examples 1 to 4 may be easily recognized by those skilled in the technical field by referring to the synthesis paths and source materials described above.

Evaluation Example 1

The HOMO energy level, LUMO energy level, singlet (Si) energy level, and triplet (T$_1$) energy level of the compounds used in Synthesis Example 1 to 4, Examples 1 to 24, and Comparative Examples 1 to 5 were each measured using structure optimization at the level of B3LYP, 6-31G(d,p) using the DFT method of the Gaussian program.

TABLE 1

| Host | HOMO (eV) | LUMO (eV) | S$_1$ (eV) | T$_1$ (eV) |
| --- | --- | --- | --- | --- |
| Compound 1 | −5.7 | −2.7 | 3.0 | 2.5 |
| Compound 2 | −5.7 | −2.7 | 3.0 | 2.5 |
| Compound 3 | −5.7 | −2.7 | 3.0 | 2.5 |
| Compound 4 | −5.7 | −2.7 | 3.0 | 2.5 |
| Compound 5 | −5.8 | −2.6 | 3.1 | 2.6 |
| Compound 6 | −5.8 | −2.6 | 3.1 | 2.6 |
| Compound 7 | −5.6 | −2.8 | 3.0 | 2.4 |
| Compound 8 | −5.6 | −2.8 | 3.0 | 2.4 |
| Compound 9 | −5.6 | −2.8 | 3.0 | 2.4 |
| Compound 10 | −5.6 | −2.8 | 3.0 | 2.4 |
| Compound 11 | −5.7 | −2.7 | 3.1 | 2.5 |
| Compound 12 | −5.7 | −2.7 | 3.1 | 2.5 |
| PD13 | −5.1 | −2.5 | 2.4 | 2.4 |
| DF10 | −5.1 | −2.1 | 2.9 | 2.3 |
| H125 | −5.5 | −1.9 | 3.1 | 2.9 |
| CPCBPTz | −5.5 | −2.7 | 3.0 | 2.7 |
| mCBP | −5.6 | −2.3 | 3.0 | 2.8 |

TABLE 1-continued
| Host | HOMO (eV) | LUMO (eV) | $S_1$ (eV) | $T_1$ (eV) |
|---|---|---|---|---|
| Compound A1 | −5.3 | −2.3 | 2.9 | 2.8 |
| Compound A2 | −5.2 | −2.3 | 2.8 | 2.6 |
| Compound B1 | −5.5 | −2.6 | 2.8 | 2.6 |
| PD8 | −5.2 | −2.5 | 2.5 | 2.4 |
| Compound B2 | −5.1 | −2.2 | 2.8 | 2.6 |
| H126 | −5.5 | −1.9 | 3.0 | 2.7 |
| Compound C1 | −5.5 | −1.8 | 3.0 | 2.6 |
| Compound C2 | −5.5 | −2.6 | 2.9 | 2.5 |
| Compound C3 | −5.2 | −2.3 | 2.6 | 2.5 |
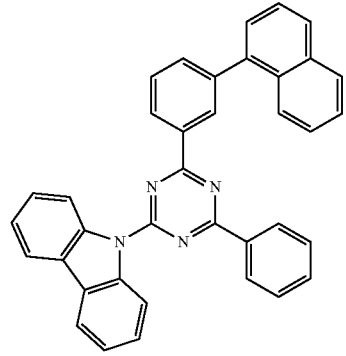
1
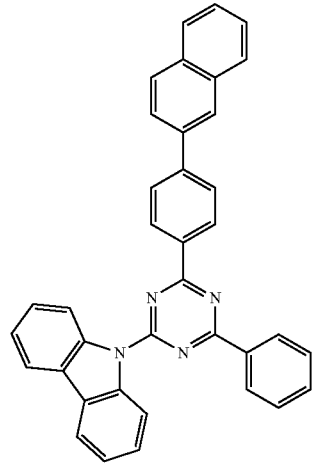
2
3
TABLE 1-continued
| Host | HOMO (eV) | LUMO (eV) | $S_1$ (eV) | $T_1$ (eV) |
|---|---|---|---|---|
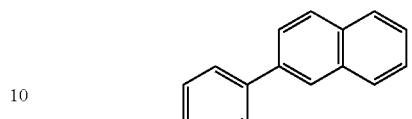
4
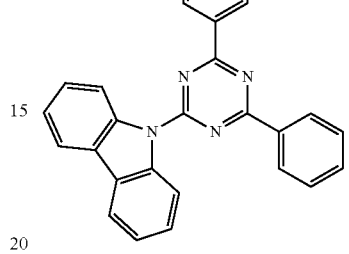
5
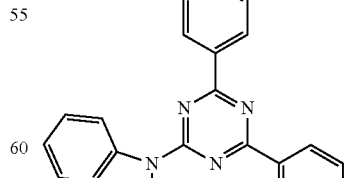
6

TABLE 1-continued
| Host | HOMO (eV) | LUMO (eV) | S₁ (eV) | T₁ (eV) |
|------|-----------|-----------|---------|---------|
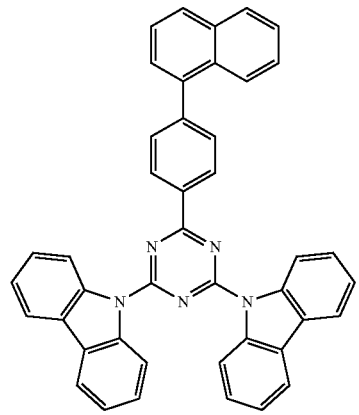
7
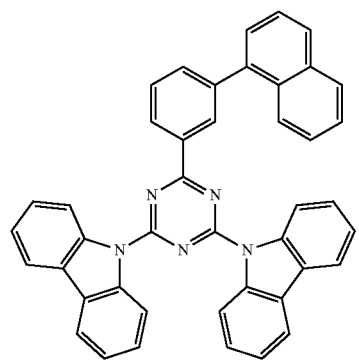
8
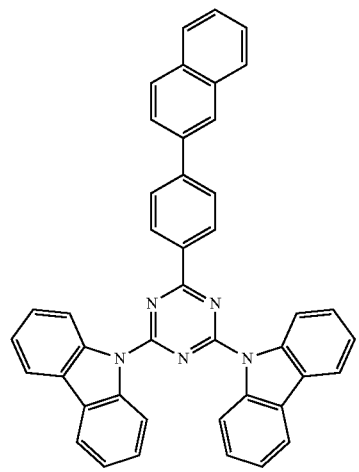
9
TABLE 1-continued
| Host | HOMO (eV) | LUMO (eV) | S₁ (eV) | T₁ (eV) |
|------|-----------|-----------|---------|---------|
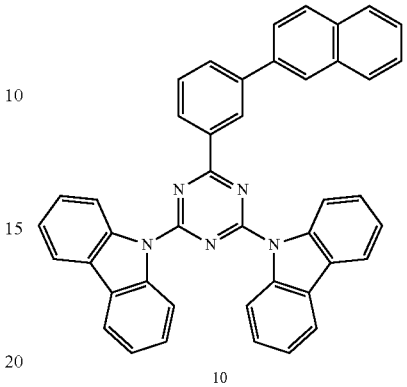
10
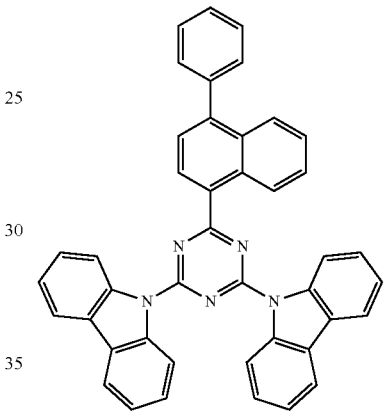
11
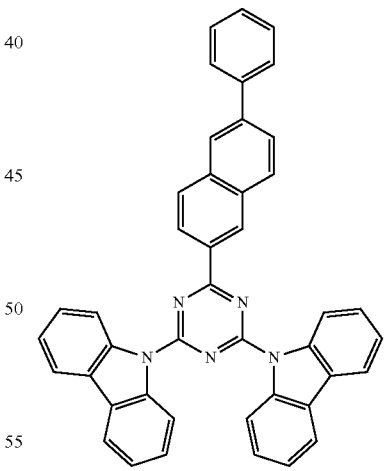
12
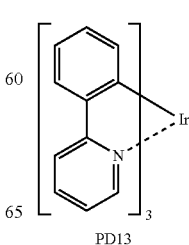
PD13

TABLE 1-continued
| Host | HOMO (eV) | LUMO (eV) | S₁ (eV) | T₁ (eV) |
|---|---|---|---|---|
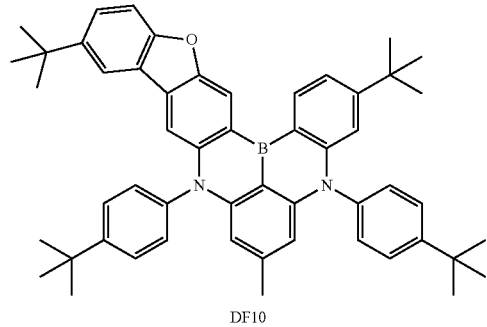
DF10
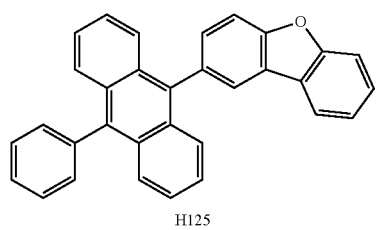
H125
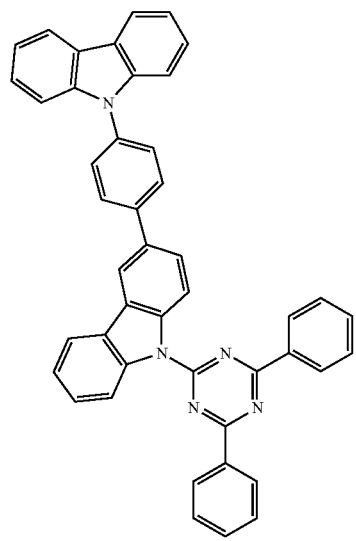
CPCBPTz
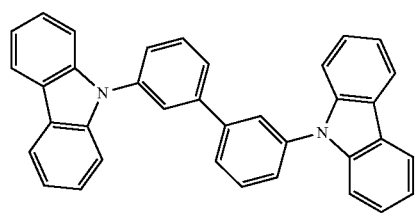
mCBP
TABLE 1-continued
| Host | HOMO (eV) | LUMO (eV) | S₁ (eV) | T₁ (eV) |
|---|---|---|---|---|
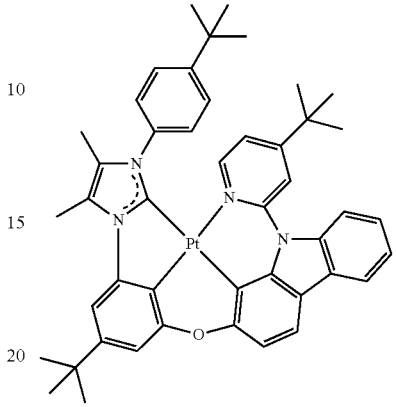
A1
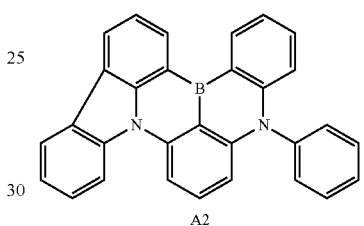
A2
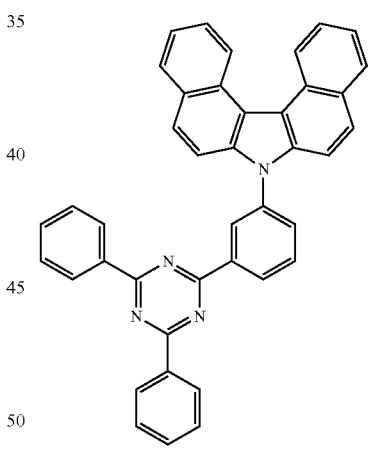
B1
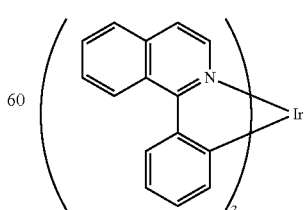
PD8

TABLE 1-continued

| Host | HOMO (eV) | LUMO (eV) | $S_1$ (eV) | $T_1$ (eV) |
|---|---|---|---|---|

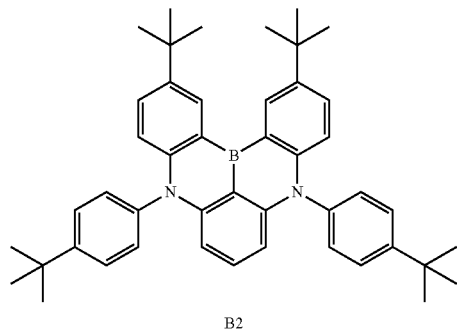 [SMILES: CC(C)(C)c1ccc(N2c3ccc(C(C)(C)C)cc3B3c4cc(C(C)(C)C)ccc4N(c4ccc(C(C)(C)C)cc4)c4cccc2c43)cc1 ; "B2"]

B2

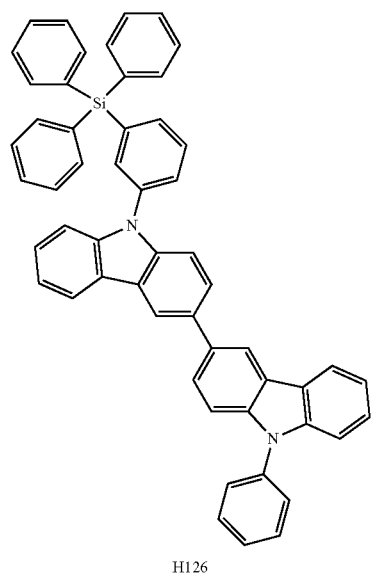 [SMILES: c1ccc(-n2c3ccccc3c3cc(-c4ccc5c(c4)c4ccccc4n5-c4cccc([Si](c5ccccc5)(c5ccccc5)c5ccccc5)c4)ccc32)cc1 ; "H126"]

H126

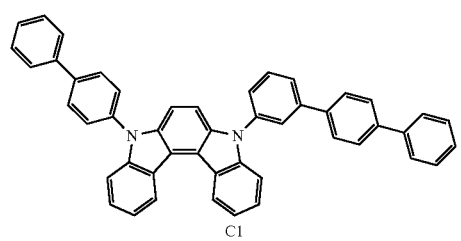

C1

TABLE 1-continued

| Host | HOMO (eV) | LUMO (eV) | $S_1$ (eV) | $T_1$ (eV) |
|---|---|---|---|---|

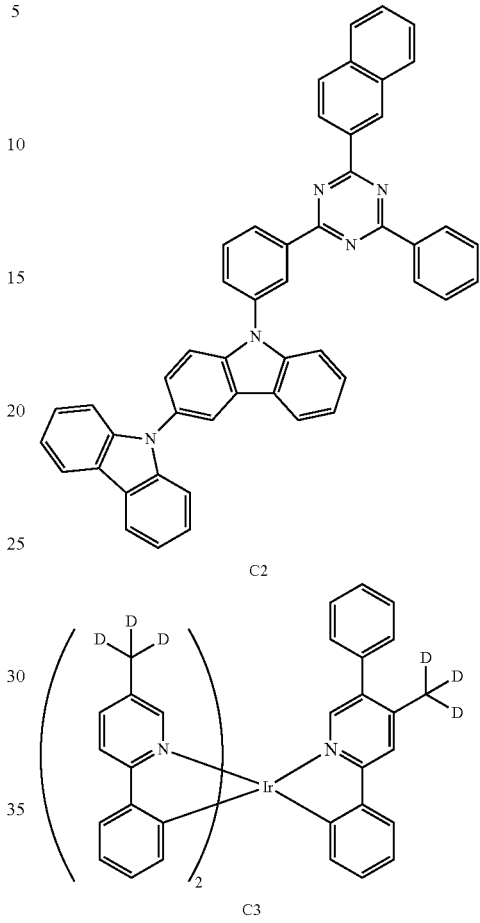

C2

C3

Example 1

As a substrate and an anode, a glass substrate with 30 Ω/cm² (300 Å) ITO thereon, which was manufactured by Corning Inc., was cut to a size of 50 mm×50 mm×0.7 mm, and the glass substrate was sonicated using isopropyl alcohol and pure water for 5 minutes each, and cleaned by irradiation of ultraviolet rays and exposure of ozone thereto for 30 minutes. The resultant glass substrate was loaded onto a vacuum deposition apparatus.

HAT-CN was vacuum-deposited on the ITO anode formed on the glass substrate to form a hole injection layer having a thickness of 100 Å, and NPB was vacuum-deposited on the hole injection layer to form a hole transport layer having a thickness of 1,800 Å.

mCBP was vacuum deposited on the hole transport layer to form an electron blocking layer having a thickness of 50 Å.

Compound 1:PD13:DF10 were co-deposited on the electron blocking layer to a weight ratio of 89:10:1 to form an emission layer having a thickness of 300 Å.

ET46 was deposited on the emission layer to form a hole blocking layer having a thickness of 50 Å, ET47:Liq was deposited on the hole blocking layer to form an electron transport layer having a thickness of 300 Å, Yb was deposited on the electron transport layer to form an electron injection layer having a thickness of 10 Å, and Ag:Mg were co-deposited on the electron injection layer to a weight ratio of 90:10 to form a cathode having a thickness of 1,000 Å, thereby completing the manufacture of an organic light-emitting device.
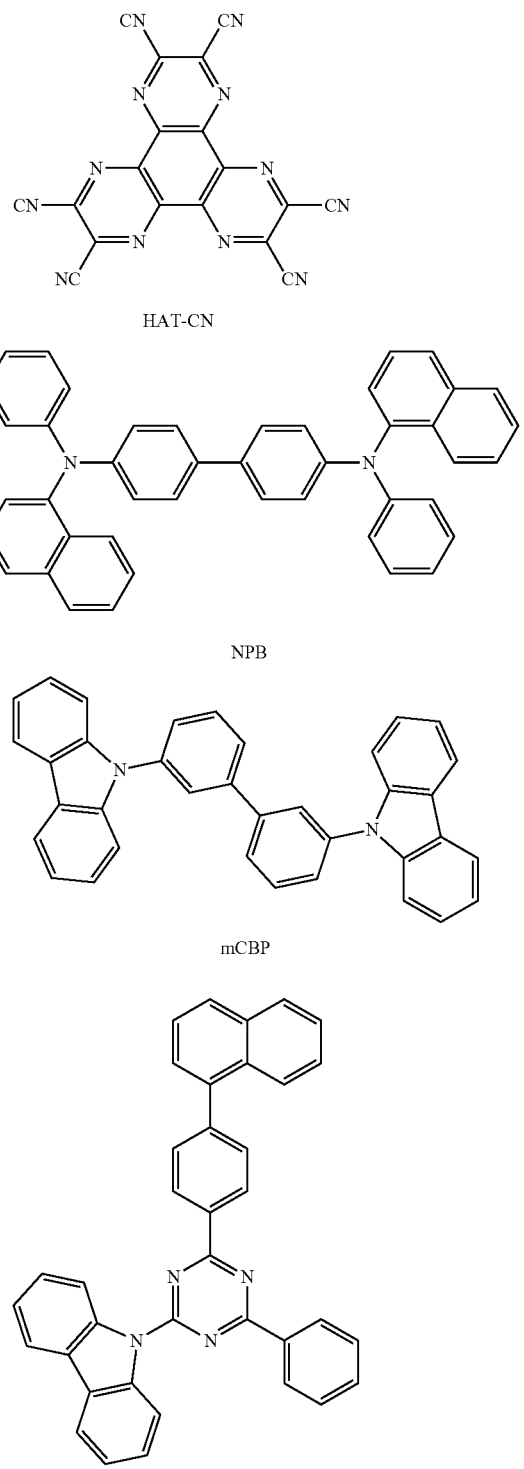
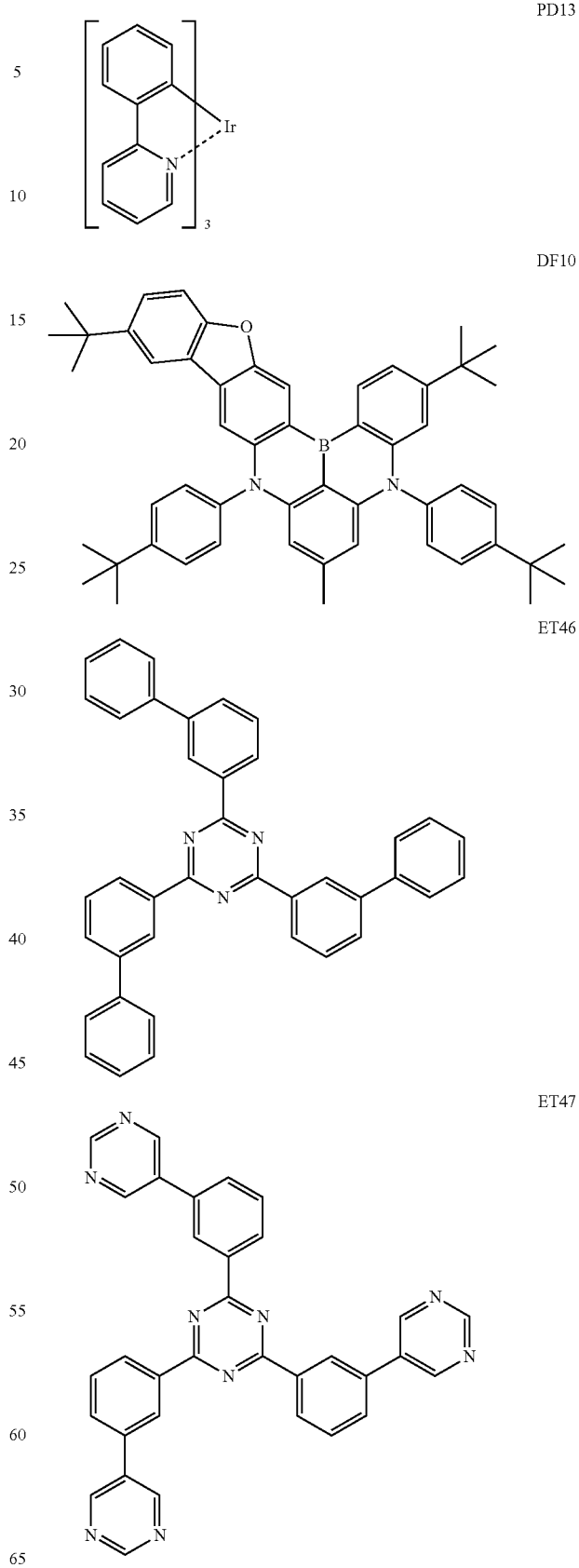

Examples 2 to 12

Light-emitting devices were manufactured in the same manner as in Example 1, except that, in forming emission layers, the compounds of Table 2 were used instead of Compound 1.

Comparative Example 1

Light-emitting devices were manufactured in the same manner as in Example 1, except that, in forming emission layers, H125:DF10 were co-deposited to a weight ratio of 99:1 instead of co-depositing Compound 1:PD13:DF10 to a weight ratio of 89:10:1.

Comparative Example 2

Light-emitting devices were manufactured in the same manner as in Example 1, except that, in forming emission layers, mCBP:Compound A1:Compound A2 were co-deposited to a weight ratio of 89:10:1 instead of co-depositing Compound 1:PD13:DF10 to a weight ratio of 89:10:1.

Comparative Example 3

Light-emitting devices were manufactured in the same manner as in Example 1, except that, in forming emission layers, Compound B1:PD8: Compound B2 were co-deposited to a weight ratio of 89:10:1 instead of co-depositing Compound 1:PD13:DF10 to a weight ratio of 89:10:1.

Evaluation Example 2

To evaluate characteristics of the light-emitting devices manufactured according to Examples 1 to 12 and Comparative Examples 1 to 3, the driving voltage (V) at 1,000 cd/m2, maximum external quantum efficiency (EQE) (%), and lifespan (hr) thereof were each measured by using Keithley SMU 236, external quantum efficiency measurement device C9920-2-12 of Hamamatsu Photonics Inc., and luminance meter PR650, and results thereof are shown in Table 2. In evaluating the maximum external quantum efficiency, the luminance/current density was measured using a luminance meter that was calibrated for wavelength sensitivity, and the maximum external quantum efficiency was converted by assuming an angular luminance distribution (Lambertian) which introduced a perfect reflecting diffuser. The lifespan indicates an amount of time (hr) that lapsed for the luminance to reach 97% of initial luminance.

TABLE 2

|  | Emission layer (weight ratio) | Driving voltage (V) | Maximum external quantum efficiency (%) | Lifespan ($T_{97}$, hr) |
| --- | --- | --- | --- | --- |
| Example 1 | Compound 1:PD13:DF10 (89:10:1) | 4.2 | 25 | 320 |
| Example 2 | Compound 2:PD13:DF10 (89:10:1) | 4.4 | 25 | 330 |
| Example 3 | Compound 3:PD13:DF10 (89:10:1) | 4.3 | 26 | 320 |
| Example 4 | Compound 4:PD13:DF10 (89:10:1) | 4.0 | 25 | 300 |
| Example 5 | Compound 5:PD13:DF10 (89:10:1) | 4.2 | 28 | 280 |
| Example 6 | Compound 6:PD13:DF10 (89:10:1) | 4.2 | 26 | 300 |
| Example 7 | Compound 7:PD13:DF10 (89:10:1) | 4.3 | 24 | 310 |
| Example 8 | Compound 8:PD13:DF10 (89:10:1) | 4.2 | 27 | 320 |
| Example 9 | Compound 9:PD13:DF10 (89:10:1) | 4.1 | 26 | 300 |
| Example 10 | Compound 10:PD13:DF10 (89:10:1) | 4.2 | 28 | 305 |
| Example 11 | Compound 11:PD13:DF10 (89:10:1) | 4.0 | 30 | 315 |
| Example 12 | Compound 12:PD13:DF10 (89:10:1) | 4.0 | 30 | 320 |
| Comparative Example 1 | H125:DF10 (99:1) | 3.8 | 11 | 150 |
| Comparative Example 2 | mCBP:Compound A1:Compound A2 (89:10:1) | 4.5 | 17 | 20 |
| Comparative Example 3 | Compound B1:PD8:Compound B2 (89:10:1) | 4.2 | 19 | 55 |

Table 2 shows that the organic light-emitting devices of Examples 1 to 12 have equivalent or lower driving voltage, excellent maximum external quantum efficiency, and better lifespan characteristics compared to the organic light-emitting devices of Comparative Examples 1 to 3.

Example 13

Light-emitting devices were manufactured in the same manner as in Example 1, except that, in forming emission layers, as co-hosts, H126 and Compound 1 at a weight ratio of 5:5 were used instead of Compound 1.

Examples 14 to 24

Light-emitting devices were manufactured in the same manner as in Example 13, except that, in forming emission layers, the compounds of Table 3 were used instead of Compound 1.

Comparative Example 4

Light-emitting devices were manufactured in the same manner as in Example 13, except that, in forming emission layers, H126:CPCBPTz:PD13 were co-deposited to a weight ratio of 45:45:10 instead of co-depositing H126:Compound 1:PD13:DF10 to a weight ratio of 44.5:44.5:10:1.

Comparative Example 5

Light-emitting devices were manufactured in the same manner as in Example 13, except that, in forming emission layers, Compound C1:Compound C2:Compound C3 were co-deposited to a weight ratio of 45:45:10 instead of co-depositing H126:Compound 1:PD13:DF10 to a weight ratio of 44.5:44.5:10:1.

Evaluation Example 3

To evaluate characteristics of the light-emitting devices manufactured according to Examples 13 to 24 and Comparative Examples 4 and 5, the driving voltage (V) at 1,000 cd/m2, maximum external quantum efficiency (EQE) (%), and lifespan (hr) thereof were each measured by using Keithley SMU 236, external quantum efficiency measurement device C9920-2-12 of Hamamatsu Photonics Inc., and luminance meter PR650, and results thereof are shown in Table 3. In evaluating the maximum external quantum efficiency, the luminance/current density was measured using a luminance meter that was calibrated for wavelength sensitivity, and the maximum external quantum efficiency was converted by assuming an angular luminance distribution (Lambertian) which introduced a perfect reflecting diffuser. The lifespan indicates an amount of time (hr) that lapsed for the luminance to reach 97% of initial luminance.

TABLE 3

| | Emission layer (weight ratio) | Driving voltage (V) | Maximum external quantum efficiency (%) | Lifespan ($T_{97}$, hr) |
|---|---|---|---|---|
| Example 13 | H126:Compound 1:PD13:DF10 (44.5:44.5:10:1) | 3.9 | 28 | 420 |
| Example 14 | H126:Compound 2:PD13:DF10 (44.5:44.5:10:1) | 3.9 | 28 | 430 |
| Example 15 | H126:Compound 3:PD13:DF10 (44.5:44.5:10:1) | 3.9 | 29 | 445 |
| Example 16 | H126:Compound 4:PD13:DF10 (44.5:44.5:10:1) | 4.0 | 30 | 460 |
| Example 17 | H126:Compound 5:PD13:DF10 (44.5:44.5:10:1) | 4.0 | 28 | 415 |
| Example 18 | H126:Compound 6:PD13:DF10 (44.5:44.5:10:1) | 3.9 | 28 | 450 |
| Example 19 | H126:Compound 7:PD13:DF10 (44.5:44.5:10:1) | 3.9 | 31 | 425 |
| Example 20 | H126:Compound 8:PD13:DF10 (44.5:44.5:10:1) | 4.1 | 30 | 385 |
| Example 21 | H126:Compound 9:PD13:DF10 (44.5:44.5:10:1) | 4.0 | 29 | 390 |
| Example 22 | H126:Compound 10:PD13:DF10 (44.5:44.5:10:1) | 3.9 | 29 | 360 |
| Example 23 | H126:Compound 11:PD13:DF10 (44.5:44.5:10:1) | 3.8 | 32 | 370 |
| Example 24 | H126:Compound 12:PD13:DF10 (44.5:44.5:10:1) | 3.9 | 30 | 355 |
| Comparative Example 4 | H126:CPCBPTz:PD13 (45:45:10) | 4.0 | 27 | 250 |
| Comparative Example 5 | Compound C1:Compound C2:Compound C3 (45:45:10) | 4.2 | 27 | 240 |

Table 3 shows that the organic light-emitting devices of Examples 13 to 24 have equivalent or lower driving voltage, excellent maximum external quantum efficiency, and better lifespan characteristics compared to the organic light-emitting devices of Comparative Examples 4 and 5.

Because the light-emitting device has high emission efficiency and a long lifespan, the light-emitting device may be used in manufacturing high-quality electronic apparatuses.

Embodiments have been disclosed herein, and although terms are employed, they are used and are to be interpreted in a generic and descriptive sense only and not for purpose of limitation. In some instances, as would be apparent by one of ordinary skill in the art, features, characteristics, and/or elements described in connection with an embodiment may be used singly or in combination with features, characteristics, and/or elements described in connection with other embodiments unless otherwise specifically indicated. Accordingly, it will be understood by those of ordinary skill in the art that various changes in form and details may be made without departing from the spirit and scope of the disclosure as set forth in the following claims.

What is claimed is:
1. A light-emitting device comprising:
a first electrode;
a second electrode facing the first electrode; and
an interlayer disposed between the first electrode and the second electrode, wherein
the interlayer includes an emission layer,
the emission layer includes a host, a first dopant, and a second dopant,
the host, the first dopant, and the second dopant are different from each other,
the host includes a compound represented by Formula 1,
the light-emitting device satisfies Relationship Equation 1, and
the light-emitting device satisfies at least one of Relationship Equation 2-1 and Relationship Equation 2-2:

[Formula 1]

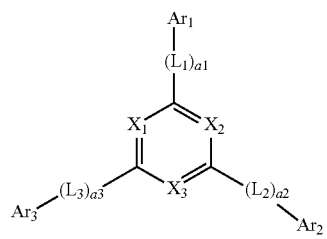

-continued

2

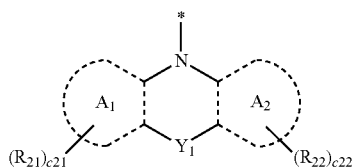

wherein in Formula 1, $X_1$, $X_2$, and $X_3$ are each independently $C(R_1)$ or N, at least one of $X_1$ to $X_3$ is N, $Ar_1$ and $Ar_2$ are each independently a group represented by Formula 2 or a π electron-rich $C_3$-$C_{60}$ cyclic group unsubstituted or substituted with at least one $R_{10a}$, $Ar_3$ is a group represented by Formula 2, $L_1$ to $L_3$ are each independently a single bond, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, and a1 to a3 are each independently an integer from 0 to 5, wherein in Formula 2, $Y_1$ is a single bond, O, S, $N(Z_{11})$, $C(Z_{11})(Z_{12})$, or $Si(Z_{11})(Z_{12})$, $A_1$ and $A_2$ are each independently a π electron-rich $C_3$-$C_{60}$ cyclic group unsubstituted or substituted with at least one $R_{10a}$, $R_1$, $R_{21}$, $R_{22}$, $Z_{11}$, and $Z_{12}$ are each independently hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$), and c21 and c22 are each independently an integer from 0 to 10, $R_{10a}$ is:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or a combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or a combination thereof; or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ are each independently: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or a combination thereof, two groups of $Q_1$ to $Q_3$ are optionally linked to each other to form a $C_4$-$C_{60}$ carbocyclic group unsubstituted or substituted with at least one $R_{10a}$ or a $C_1$-$C_{60}$ heterocyclic group unsubstituted or substituted with at least one $R_{10a}$, two groups of $Q_{11}$ to $Q_{13}$ are optionally linked to each other to form a $C_4$-$C_{60}$ carbocyclic group unsubstituted or substituted with at least one $R_{10a}$ or a $C_1$-$C_{60}$ heterocyclic group unsubstituted or substituted with at least one $R_{10a}$, two groups of $Q_{31}$ to $Q_{33}$ are optionally linked to each other to form a $C_4$-$C_{60}$ carbocyclic group unsubstituted or substituted with at least one $R_{10a}$ or a $C_1$-$C_{60}$ heterocyclic group unsubstituted or substituted with at least one $R_{10a}$, and

* indicates a binding site to a neighboring atom:

$$S_1(H) \geq S_1(D2) \geq T_1(H) \geq T_1(D1) \geq T_1(D2) \quad \text{[Relationship Equation 1]}$$

wherein in Relationship Equation 1, $S_1(H)$ is:

a singlet energy level (eV) of the compound represented by Formula 1 when the host includes only a compound represented by Formula 1, or a singlet energy level (eV) of an exciplex when the host includes as a first host the compound represented by Formula 1 and further includes a second host different from the first host, and when the first host and the second host form an exciplex, or a lower value among the singlet energy level (eV) of the first host and the singlet energy level (eV) of the second host when the host includes as a first host the compound represented by Formula 1 and further includes a second host different from the first host, and when the first host and the second host do not form an exciplex, $S_1(D2)$ is a singlet energy level (eV) of the second dopant, $T_1(H)$ is:

a triplet energy level (eV) of the compound represented by Formula 1 when the host includes only a compound represented by Formula 1, or a triplet energy level (eV) of an exciplex when the host includes as a first host the compound represented by Formula 1 and further includes a second host different from the first host, and when the first host and the second host form an exciplex, or a lower value among the triplet energy level (eV) of the first host and the triplet energy level (eV) of the second host when the host includes as a first host the compound represented by Formula 1 and further includes a second host different from the first host, and when the first host and the second host do not form an exciplex, $T_1(D1)$ is a triplet energy level (eV) of the first dopant, and $T_1(D2)$ is a triplet energy level (eV) of the second dopant;

LUMO(H)+0.1 eV≤LUMO(D1)  [Relationship Equation 2-1]

LUMO(H)+0.1 eV≤LUMO(D2)  [Relationship Equation 2-2]

wherein in Relationship Equations 2-1 and 2-2, LUMO(H) is:
- a lowest unoccupied molecular orbital (LUMO) energy level (eV) of the compound represented by Formula 1 when the host includes only a compound represented by Formula 1, or
- a LUMO energy level (eV) of an exciplex when the host includes as a first host the compound represented by Formula 1 and further includes a second host different from the first host, and when the first host and the second host form an exciplex, or
- a lower value among the LUMO energy level (eV) of the first host and the LUMO energy level (eV) of the second host when the host includes as a first host the compound represented by Formula 1 and further includes a second host different from the first host, and when the first host and the second host do not form an exciplex, LUMO(D1) is a LUMO energy level (eV) of the first dopant, and LUMO(D2) is a LUMO energy level (eV/) of the second dopant.

2. The light-emitting device of claim 1, wherein $X_1$ to $X_3$ in Formula 1 is each N.

3. The light-emitting device of claim 1, wherein
the π electron-rich $C_3$-$C_{60}$ cyclic group is a first ring, or a condensed ring in which two or more first rings are condensed with each other, and
the first ring is a benzene group, a naphthalene group, a cyclopentadiene group, a pyrrole group, a furan group, a thiophene group, or a silole group.

4. The light-emitting device of claim 1, wherein $Ar_1$ in Formula 1 is a group represented by one of Formulae 3-1 to 3-20:

3-1

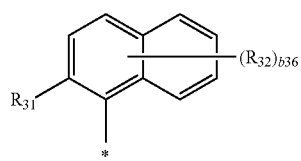

3-2

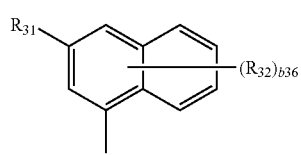

3-3

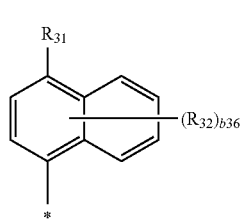

3-4

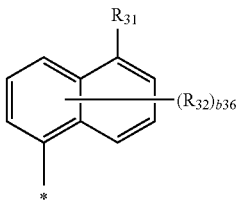

3-5

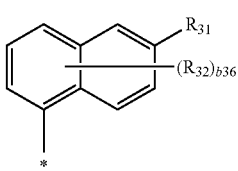

3-6

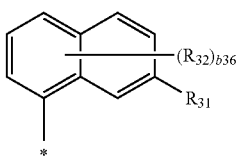

3-7

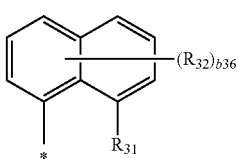

3-8

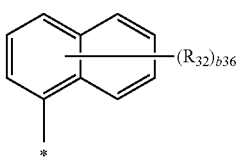

3-9

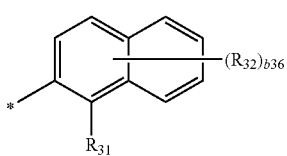

3-10

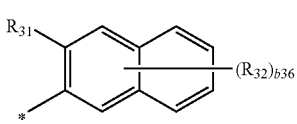

3-11

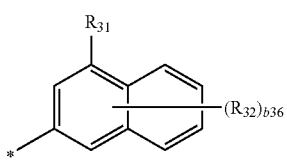

3-12

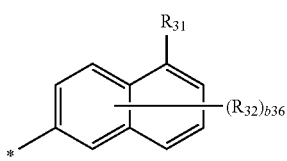

-continued

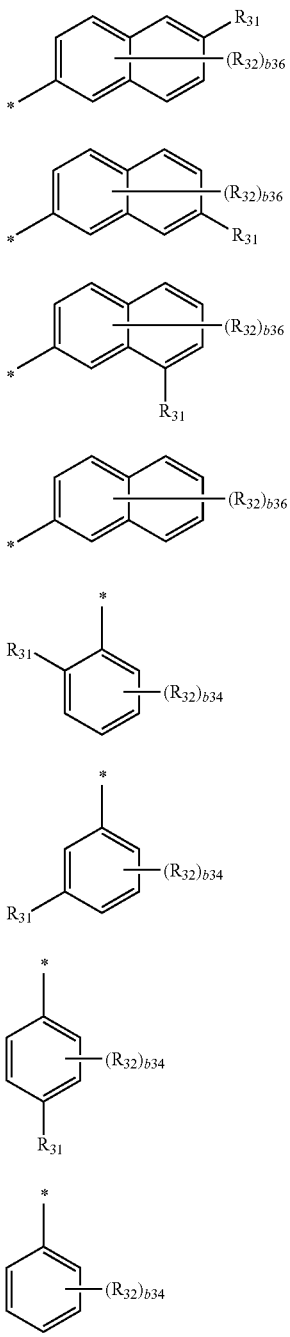

wherein in Formulae 3-1 to 3-20,
R$_{31}$ and R$_{32}$ are each independently the same as described in connection with R$_1$, wherein R$_{31}$ is not hydrogen,
b36 is an integer from 0 to 6,
b34 is an integer from 0 to 4, and
* indicates a binding site to a neighboring atom.

5. The light-emitting device of claim 1, wherein Ar$_2$ in Formula 1 is a group represented by Formula 2, a benzene group, a heptalene group, an indene group, a naphthalene group, an azulene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, a furan group, a thiophene group, an isoindole group, an indole group, a benzofuran group, a benzothiophene group, a benzosilole group, a naphthopyrrole group, a naphthofuran group, a naphthothiophene group, a naphthosilole group, a benzocarbazole group, a dibenzocarbazole group, a dibenzofuran group, a dibenzothiophene group, a carbazole group, a dibenzosilole group, an indenocarbazole group, an indolocarbazole group, a benzofurocarbazole group, a benzothienocarbazole group, a benzosilolocarbazole group, a triindolobenzene group, a pyrrolophenanthrene group, a furanophenanthrene group, a thienophenanthrene group, a benzonaphthofuran group, a benzonaphthothiophene group, an indolophenanthrene group, a benzofuranophenanthrene group, or a benzothienophenanthrene group.

6. The light-emitting device of claim 1, wherein L$_1$ in Formula 1 is a single bond or a group represented by one of Formulae 4-1 to 4-17:

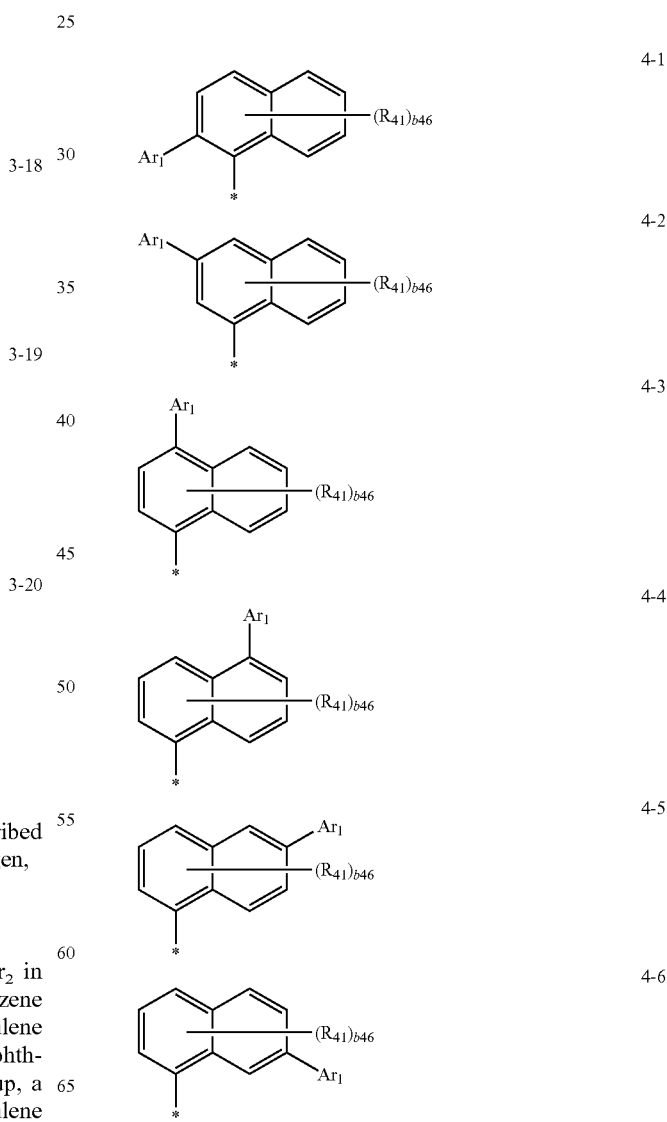

-continued

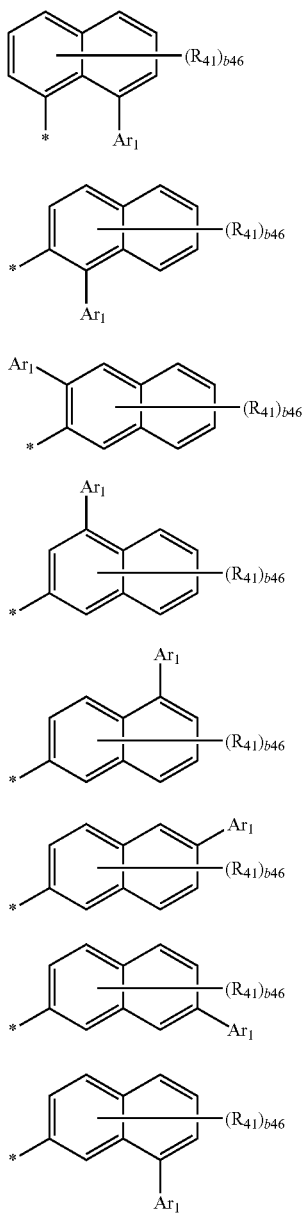

-continued

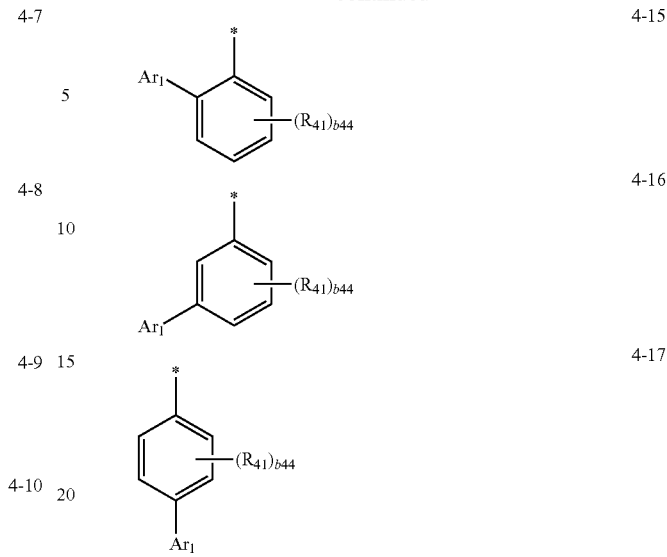

wherein in Formulae 4-1 to 4-17,
$Ar_1$ is the same as defined in connection with Formula 1,
$R_{41}$ is the same as described in connection with $R_1$ in Formula 1,
b46 is an integer from 0 to 6,
b44 is an integer from 0 to 4, and
* indicates a binding site to a neighboring atom.

7. The light-emitting device of claim 1, wherein $L_3$ in Formula 1 is a single bond.

8. The light-emitting device of claim 1, wherein
$Ar_1$ and $Ar_2$ in Formula 1 are each independently a benzene group unsubstituted or substituted with at least one $R_{10a}$ or a naphthalene group unsubstituted or substituted with at least one $R_{10a}$, and
$L_1$ to $L_3$ in Formula 1 are each independently a single bond, a benzene group unsubstituted or substituted with at least one $R_{10a}$, or a naphthalene group unsubstituted or substituted with at least one $R_{10a}$.

9. The light-emitting device of claim 1, wherein
the host includes a first host and a second host,
the first host is a compound represented by Formula 1, and
the first dopant and second dopant are different from each other.

10. The light-emitting device of claim 9, wherein the second host is a compound represented by Formula 301-1 or a compound represented by Formula 301-2:

[Formula 301-1]

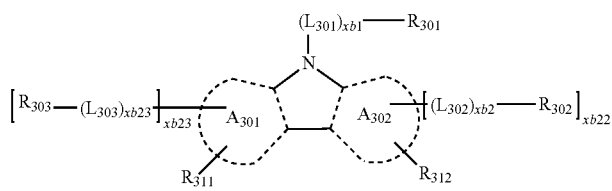

[Formula 301-2]

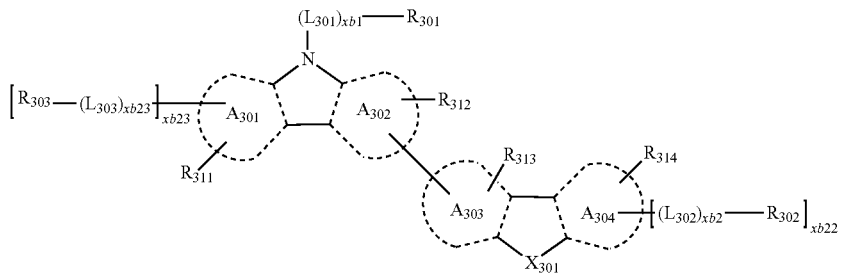

wherein in Formulae 301-1 and 301-2,
ring $A_{301}$ to ring $A_{304}$ and $L_{301}$ to $L_{304}$ are each independently a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xb1 to xb4 are each independently an integer from 0 to 5, $X_{301}$ is O, S, N-[$(L_{304})_{xb4}$-$R_{304}$], $C(R_{304})(R_{305})$, or $Si(R_{304})(R_{305})$, $R_{301}$ to $R_{305}$ and $R_{311}$ to $R_{314}$ are each independently hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si$(Q_{301})(Q_{302})(Q_{303})$, —N$(Q_{301})(Q_{302})$, —B$(Q_{301})(Q_{302})$, —C(=O)$(Q_{301})$, —S(=O)$_2$$(Q_{301})$, or —P(=O)$(Q_{301})(Q_{302})$, xb22 and xb23 are each independently 0, 1, or 2, $Q_{301}$ to $Q_{303}$ are each independently the same as described in connection with $Q_1$ in Formula 1, and $R_{10a}$ is the same as described in connection with $R_{10a}$ in Formula 1.

11. The light-emitting device of claim 9, wherein the first host and the second host form an exciplex.

12. The light-emitting device of claim 1, wherein the second dopant is a boron-containing compound.

13. The light-emitting device of claim 1, wherein the first dopant and the second dopant are each an emitter.

14. The light-emitting device of claim 1, wherein
the first dopant is a phosphorescence emitter,
the second dopant is a fluorescence emitter, and
the emission layer simultaneously emits phosphorescence emitted from the first dopant and fluorescence emitted from the second dopant.

15. The light-emitting device of claim 1, wherein
the first dopant is a green emitter or a red emitter, and
the second dopant is a blue emitter, a green emitter, or a red emitter.

16. The light-emitting device of claim 1, wherein, in the emission layer, an amount of the first dopant is greater than an amount of the second dopant.

17. An electronic apparatus comprising the light-emitting device of claim 1.

18. The electronic apparatus of claim 17, further comprising a thin-film transistor, wherein the thin-film transistor includes a source electrode and a drain electrode, and
the first electrode of the light-emitting device is electrically connected to at least one of the source electrode and the drain electrode of the thin-film transistor.

19. The electronic apparatus of claim 17, wherein the electronic apparatus further comprises a color filter, a color conversion layer, a touch screen layer, a polarizing layer, or a combination thereof.

20. A light-emitting device comprising:
a first electrode;
a second electrode facing the first electrode; and
an interlayer disposed between the first electrode and the second electrode, wherein
the interlayer includes an emission layer,
the emission layer includes a host, a first dopant, and a second dopant,
the host, the first dopant, and the second dopant are different from each other,
the host includes a compound represented by Formula 1, and
the light-emitting device satisfies at least one of Relationship Equation 2-1 and Relationship Equation 2-2:

[Formula 1]

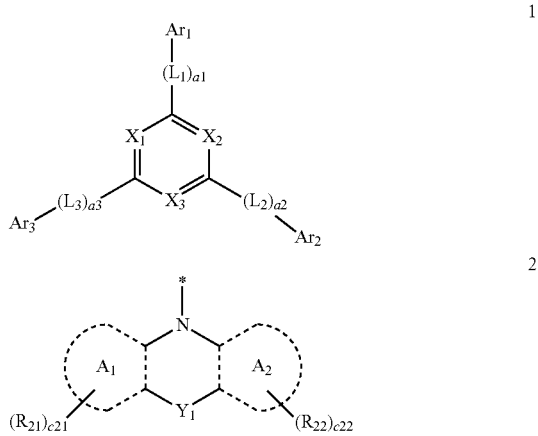

wherein in Formula 1,
$X_1$, $X_2$, and $X_3$ are each independently $C(R_1)$ or N,
at least one of $X_1$ to $X_3$ is N,
$Ar_1$ and $Ar_2$ are each independently a group represented by Formula 2 or a π electron-rich $C_3$-$C_{60}$ cyclic group unsubstituted or substituted with at least one $R_{10a}$, Ar$_3$ is a group represented by Formula 2, L$_1$ to L$_3$ are each independently a single bond, a C$_3$-C$_{60}$ carbocyclic group unsubstituted or substituted with at least one R$_{10a}$, or a C$_1$-C$_{60}$ heterocyclic group unsubstituted or substituted with at least one R$_{10a}$, and a1 to a3 are each independently an integer from 0 to 5, wherein in Formula 2, Y$_1$ is a single bond, O, S, N(Z$_{11}$), C(Z$_{11}$)(Z$_{12}$), or Si(Z$_{11}$)(Z$_{12}$), A$_1$ and A$_2$ are each independently a π electron-rich C$_3$-C$_{60}$ cyclic group unsubstituted or substituted with at least one R$_{10a}$, R$_1$, R$_{21}$, R$_{22}$, Z$_{11}$, and Z$_{12}$ are each independently hydrogen, deuterium, —F, —Cl, —Br, —I, a hydroxyl group, a cyano group, a nitro group, a C$_1$-C$_{60}$ alkyl group unsubstituted or substituted with at least one R$_{10a}$, a C$_2$-C$_{60}$ alkenyl group unsubstituted or substituted with at least one R$_{10a}$, a C$_2$-C$_{60}$ alkynyl group unsubstituted or substituted with at least one R$_{10a}$, a C$_1$-C$_{60}$ alkoxy group unsubstituted or substituted with at least one R$_{10a}$, a C$_3$-C$_{60}$ carbocyclic group unsubstituted or substituted with at least one R$_{10a}$, a C$_1$-C$_{60}$ heterocyclic group unsubstituted or substituted with at least one R$_{10a}$, a C$_6$-C$_{60}$ aryloxy group unsubstituted or substituted with at least one R$_{10a}$, a C$_6$-C$_{60}$ arylthio group unsubstituted or substituted with at least one R$_{10a}$, —Si(Q$_1$)(Q$_2$)(Q$_3$), —N(Q$_1$)(Q$_2$), —B(Q$_1$)(Q$_2$), —C(=O)(Q$_1$), —S(=O)$_2$(Q$_1$), or —P(=O)(Q$_1$)(Q$_2$), and c21 and c22 are each independently an integer from 0 to 10, R$_{10a}$ is:

deuterium (-D), —F, —Cl, —Br, —I, a hydroxyl group, a cyano group, or a nitro group;

a C$_1$-C$_{60}$ alkyl group, a C$_2$-C$_{60}$ alkenyl group, a C$_2$-C$_{60}$ alkynyl group, or a C$_1$-C$_{60}$ alkoxy group, each unsubstituted or substituted with deuterium, —F, —Cl, —Br, —I, a hydroxyl group, a cyano group, a nitro group, a C$_3$-C$_{60}$ carbocyclic group, a C$_1$-C$_{60}$ heterocyclic group, a C$_6$-C$_{60}$ aryloxy group, a C$_6$-C$_{60}$ arylthio group, —Si(Q$_{11}$)(Q$_{12}$)(Q$_{13}$), —N(Q$_{11}$)(Q$_{12}$), —B(Q$_{11}$)(Q$_{12}$), —C(=O)(Q$_{11}$), —S(=O)$_2$(Q$_{11}$), —P(=O)(Q$_{11}$)(Q$_{12}$), or a combination thereof;

a C$_3$-C$_{60}$ carbocyclic group, a C$_1$-C$_{60}$ heterocyclic group, a C$_6$-C$_{60}$ aryloxy group, or a C$_6$-C$_{60}$ arylthio group, each unsubstituted or substituted with deuterium, —F, —Cl, —Br, —I, a hydroxyl group, a cyano group, a nitro group, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{60}$ carbocyclic group, a C$_1$-C$_{60}$ heterocyclic group, a C$_6$-C$_{60}$ aryloxy group, a C$_6$-C$_{60}$ arylthio group, —Si(Q$_{21}$)(Q$_{22}$)(Q$_{23}$), —N(Q$_{21}$)(Q$_{22}$), —B(Q$_{21}$)(Q$_{22}$), —C(=O)(Q$_{21}$), —S(=O)$_2$(Q$_{21}$), —P(=O)(Q$_{21}$)(Q$_{22}$), or a combination thereof; or —Si(Q$_{31}$)(Q$_{32}$)(Q$_{33}$), —N(Q$_{31}$)(Q$_{32}$), —B(Q$_{31}$)(Q$_{32}$), —C(=O)(Q$_{31}$), —S(=O)$_2$(Q$_{31}$), or —P(=O)(Q$_{31}$)(Q$_{32}$), wherein Q$_1$ to Q$_3$, Q$_{11}$ to Q$_{13}$, Q$_{21}$ to Q$_{23}$, and Q$_{31}$ to Q$_{33}$ are each independently: hydrogen; deuterium; —F; —Cl; —Br; —I; a hydroxyl group; a cyano group; a nitro group; a C$_1$-C$_{60}$ alkyl group; a C$_2$-C$_{60}$ alkenyl group; a C$_2$-C$_{60}$ alkynyl group; a C$_1$-C$_{60}$ alkoxy group; or a C$_3$-C$_{60}$ carbocyclic group or a C$_1$-C$_{60}$ heterocyclic group, each unsubstituted or substituted with deuterium, —F, a cyano group, a C$_1$-C$_{60}$ alkyl group, a C$_1$-C$_{60}$ alkoxy group, a phenyl group, a biphenyl group, or a combination thereof, two groups of Q$_1$ to Q$_3$ are optionally linked to each other to form a C$_4$-C$_{60}$ carbocyclic group unsubstituted or substituted with at least one R$_{10a}$ or a C$_1$-C$_{60}$ heterocyclic group unsubstituted or substituted with at least one R$_{10a}$, two groups of Q$_{11}$ to Q$_{13}$ are optionally linked to each other to form a C$_4$-C$_{60}$ carbocyclic group unsubstituted or substituted with at least one R$_{10a}$ or a C$_1$-C$_{60}$ heterocyclic group unsubstituted or substituted with at least one R$_{10a}$, two groups of Q$_{31}$ to Q$_{33}$ are optionally linked to each other to form a C$_4$-C$_{60}$ carbocyclic group unsubstituted or substituted with at least one R$_{10a}$ or a C$_1$-C$_{60}$ heterocyclic group unsubstituted or substituted with at least one R$_{10a}$, and

* indicates a binding site to a neighboring atom:

$$\text{LUMO}(H)+0.1 \text{ eV} \leq \text{LUMO}(D1) \qquad \text{[Relationship Equation 2-1]}$$

$$\text{LUMO}(H)+0.1 \text{ eV} \leq \text{LUMO}(D2) \qquad \text{[Relationship Equation 2-2]}$$

wherein in Relationship Equations 2-1 and 2-2,

LUMO(H) is:
- a lowest unoccupied molecular orbital (LUMO) energy level (eV) of the compound represented by Formula 1 when the host includes only a compound represented by Formula 1, or
- a LUMO energy level (eV) of an exciplex when the host includes as a first host the compound represented by Formula 1 and further includes a second host different from the first host, and when the first host and the second host form an exciplex, or
- a lower value among the LUMO energy level (eV) of the first host and the LUMO energy level (eV) of the second host when the host includes as a first host the compound represented by Formula 1 and further includes a second host different from the first host, and when the first host and the second host do not form an exciplex, LUMO(D1) is a LUMO energy level (eV) of the first dopant, and LUMO(D2) is a LUMO energy level (eV) of the second dopant.

* * * * *